US006664260B2

(12) United States Patent
Charles et al.

(10) Patent No.: US 6,664,260 B2
(45) Date of Patent: Dec. 16, 2003

(54) HETEROCYCLIC ETHER SUBSTITUTED IMIDAZOQUINOLINES

(75) Inventors: Leslie J. Charles, Hudson, WI (US); Joseph F. Dellaria, Woodbury, MN (US); George W. Griesgraber, Eagan, MN (US); Philip D. Heppner, Woodbury, MN (US); Karl J. Manske, Minneapolis, MN (US); John W. Mickelson, Mattawan, MI (US); Michael J. Rice, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/011,921

(22) Filed: Dec. 6, 2001

(65) Prior Publication Data

US 2003/0065005 A1 Apr. 3, 2003

Related U.S. Application Data

(60) Provisional application No. 60/254,218, filed on Dec. 8, 2000.

(51) Int. Cl.[7] .................. A61K 31/4745; A61K 31/506; C07D 471/04; A61P 37/02; A61P 31/12
(52) U.S. Cl. ........................ 514/256; 514/293; 544/333; 544/242; 546/82; 546/64
(58) Field of Search ...................... 546/82, 64; 514/293, 514/256; 544/333, 242

(56) References Cited

U.S. PATENT DOCUMENTS

| | | | |
|---|---|---|---|
| 3,314,941 A | | 4/1967 | Littell et al. |
| 3,692,907 A | * | 9/1972 | Fleming et al. ........... 514/231.8 |
| 4,689,338 A | | 8/1987 | Gerster |
| 4,698,348 A | | 10/1987 | Gerster |
| 4,929,624 A | | 5/1990 | Gerster et al. |
| 5,037,986 A | | 8/1991 | Gerster |
| 5,238,944 A | | 8/1993 | Wick et al. |
| 5,266,575 A | * | 11/1993 | Gerster et al. ............... 514/293 |
| 5,268,376 A | | 12/1993 | Gester |
| 5,346,905 A | * | 9/1994 | Gerster ....................... 514/293 |
| 5,352,784 A | | 10/1994 | Nikolaides et al. |
| 5,389,640 A | | 2/1995 | Gerster et al. |
| 5,444,065 A | | 8/1995 | Nikolaides et al. |
| 5,446,153 A | | 8/1995 | Lindstrom et al. |
| 5,482,936 A | | 1/1996 | Lindstrom |
| 5,494,916 A | | 2/1996 | Lindstrom et al. |
| 5,525,612 A | * | 6/1996 | Gerster ....................... 514/293 |
| 5,605,899 A | | 2/1997 | Gerster et al. |
| 5,627,281 A | | 5/1997 | Nikolaides et al. |
| 5,644,063 A | | 7/1997 | Lindstrom et al. |
| 5,648,516 A | | 7/1997 | Nikolaides et al. |
| 5,714,608 A | | 2/1998 | Gerster |
| 5,741,909 A | | 4/1998 | Gerster et al. |
| 5,756,747 A | | 5/1998 | Gerster et al. |
| 5,886,006 A | | 3/1999 | Nikolaides et al. |
| 5,939,090 A | | 8/1999 | Beaurline et al. |
| 5,977,366 A | | 11/1999 | Gerster et al. |
| 6,039,969 A | | 3/2000 | Tomai et al. |
| 6,069,149 A | | 5/2000 | Nanba et al. |
| 6,083,505 A | | 7/2000 | Miller et al. |
| 6,110,929 A | | 8/2000 | Gerster et al. |
| 6,194,425 B1 | * | 2/2001 | Gerster et al. ............... 514/293 |
| 6,323,200 B1 | | 11/2001 | Gerster et al. |
| 6,331,539 B1 | | 12/2001 | Crooks et al. |
| 6,348,462 B1 | | 2/2002 | Gerster et al. |
| 6,365,166 B2 | | 4/2002 | Beaurline et al. |

FOREIGN PATENT DOCUMENTS

| | | |
|---|---|---|
| JP | 9-208584 | 8/1997 |
| JP | 9-255926 | 3/1999 |
| WO | WO 93/09119 | 5/1993 |
| WO | WO 00/09506 | 2/2000 |
| WO | WO 00/76505 | 12/2000 |
| WO | WO 00/76518 | 12/2000 |

OTHER PUBLICATIONS

Testerman TL et al. Journal of Leukocyte Biology, 58, 365–372 (1995).*
Delgado JN and Remers WA. Wilson and Gisvold's Textbook of Organic Medicinal and Pharmaceutical Chemistry. Ninth Edition. (1991). pp. 30–31.*
Hart, E.P. "Napthyridines. Hydroxynaphthyridines", *Journal of Chemical Society*, Part III, pp 212–214, (1956).
Wozniak, et al, "The Amination of 3–nitro–1, 5–naphthyridines by Liquid Ammonia/Potassium Permanganate[1,2]. A New and Convenient Amination Method.", *Journal of the Royal Netherlands Chemical Society, 102*, pp 511–513, Dec. 12, 1983.
Brennan, et al, "Automated Bioassay of Interferons in Micro–test Plates", *Biotechniques*, Jun./Jul., 78, 1983.
Testerman, et al, "Cytokine Induction by the Immunomodulators Imiquimod and S–27609", *Journal of Leukocyte Biology*, vol. 58, pp. 365–372, Sep. 1995.
Bachman, et al, "Synthesis of Substituted Quinolylamines. Derivatives of 4–Amino–7–Chloroquinoline", *J. Org. Chem*, 18, pp 1278–1284 (1950).
Jain, et al, "Chemical and Pharmacological Investigations of Some ω–Substituted Alkylamino–3–aminopyridines", *J. Med. Chem.*, 11, pp 87–92 (1968).
Baranov, et al., *Chem. Abs.* 85, 94371, (1976).
Berényi, et al, "Ring Transformation of Condensed Dihydro–as–triazines", *J. Heterocyclic Chem.*, 18, pp 1537–1540 (1981).

* cited by examiner

*Primary Examiner*—Evelyn Mei Huang
(74) *Attorney, Agent, or Firm*—Dean A. Ersfeld

(57) ABSTRACT

Imidazoquinoline and tetrahydroimidazoquinoline compounds that contain ether and heterocyclyl or heteroaryl functionality at the 1-position are useful as immune response modifiers. The compounds and compositions of the invention can induce the biosynthesis of various cytokines and are useful in the treatment of a variety of conditions including viral diseases and neoplastic diseases.

57 Claims, No Drawings

HETEROCYCLIC ETHER SUBSTITUTED IMIDAZOQUINOLINES

This application claims the benefit of previously filed Provisional Application Ser. No. 60/254,218, filed on Dec. 8, 2000.

FIELD OF THE INVENTION

This invention relates to imidazoquinoline compounds that have ether and heterocycle or heteroaryl functionality at the 1-position, and to pharmaceutical compositions containing such compounds. A further aspect of this invention relates to the use of these compounds as immunomodulators, for inducing cytokine biosynthesis in animals, and in the treatment of diseases, including viral and neoplastic diseases.

BACKGROUND OF THE INVENTION

The first reliable report on the 1H-imidazo[4,5-c]quinoline ring system. Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.* 11, pp. 87–92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo[4,5-c]quinolines, and Berenyi et al., *J. Heterocyclic Chem.* 18, 1537–1540 (1981), have reported certain 2-oxoimidazo[4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

There continues to be interest in the imidazoquinoline ring system. Certain 1H-imidazo[4,5-c]naphthyridine-4-amines, 1H-imidazo[4,5-c]pyridin-4-amines, and 1H-imidazo[4,5-c]quinolin-4-amines having an ether containing substituent at the 1 position are known. These are described in U.S. Pat. Nos. 5,268,376; 5,389,640; 5,494,916; and WO 99/29693.

There is a continuing need for compounds that have the ability to modulate the immune response, by induction of cytokine biosynthesis or other mechanisms.

SUMMARY OF THE INVENTION

We have found a new class of compounds that are useful in inducing cytokine biosynthesis in animals. Accordingly, this invention provides imidazo[4,5-c]quinoline-4-amine and tetrahydroimidazo[4,5-c]quinoline-4-amine compounds that have an ether containing substituent at the 1-position. The compounds are described by Formulas (I), (II), (III) and (IV), which are defined in more detail infra. These compounds share the general structural formula

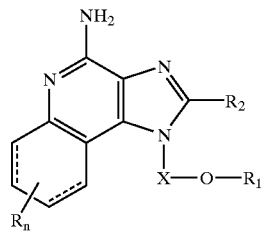

wherein X, $R_1$, $R_2$, and R are as defined herein for each class of compounds having Formulas (I), (II), (III) and (IV).

The compounds of Formulas (I), (II), (III), and (IV) are useful as immune response modifiers due to their ability to induce cytokine biosynthesis and otherwise modulate the immune response when administered to animals. This makes the compounds useful in the treatment of a variety of conditions such as viral diseases and tumors that are responsive to such changes in the immune response.

The invention further provides pharmaceutical compositions containing the immune response modifying compounds, and methods of inducing cytokine biosynthesis in an animal, treating a viral infection in an animal, and/or treating a neoplastic disease in an animal by administering a compound of Formula (I), (II), (III), or (IV) to the animal.

In addition, the invention provides methods of synthesizing the compounds of the invention and intermediates useful in the synthesis of these compounds.

DETAILED DESCRIPTION OF THE INVENTION

As mentioned earlier, we have found certain compounds that induce cytokine biosynthesis and modify the immune response in animals. Such compounds are represented by Formulas (I), (II), (III), and (IV), as shown below.

Imidazoquinoline compounds of the invention, which have ether and heterocyclyl or heteroaryl functionality at the 1-position are represented by Formula (I):

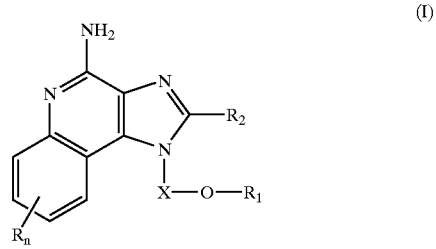

(I)

wherein:

X is —$CHR_3$—, —$CHR_3$-alkyl-, or —$CHR_3$-alkenyl-;

$R_1$ is selected from the group consisting of:
- -heteroaryl;
- -heterocyclyl;
- —$R_4$-heteroaryl; and
- —$R_4$-heterocyclyl;

$R_2$ is selected from the group consisting of:
- -hydrogen;
- -alkyl;
- -alkenyl;
- -aryl;
- -heteroaryl;
- -heterocyclyl;
- -alkyl-Y-alkyl;

-alkyl-Y-alkenyl;
-alkyl-Y-aryl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

$R_4$ is alkyl or alkenyl, which may be interrupted by one or more —O— groups;

each $R_3$ is independently H or $C_{1-10}$ alkyl;

each Y is independently —O— or —S(O)$O_{0-2}$—;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

The invention also provides imidazoquinoline compounds that contain ether functionality at the 1-position, where the ether containing substituent also contains an alkynyl group and a heterocyclyl or heteroaryl group. These compounds are represented by Formula (II):

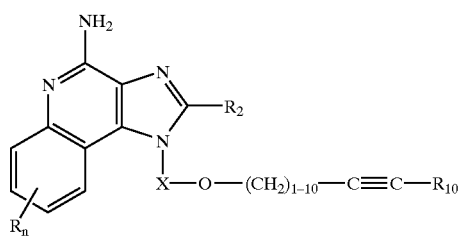

(II)

wherein:
X is —CHR$_3$—, —CHR$_3$-alkyl-, or —CHR$_3$-alkenyl-;
$R_{10}$ is selected from the group consisting of heteroaryl and heterocyclyl;
$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

n is 0 to 4;
each $R_3$ is independently H or $C_{1-10}$ alkyl;
each Y is independently —O— or —S(O)$_{0-2}$—; and
each R present is independently selected from the group consisting of $C_{1-10}$ alkyl, $C_{1-10}$ alkoxy, hydroxy, halogen and trifluoromethyl;
or a pharmaceutically acceptable salt thereof.

The invention also includes tetrahydroimidazoquinoline compounds that bear an ether and heterocyclyl or heteroaryl containing substituent at the 1-position. Such tetrahydroimidazoquinoline compounds are represented by Formula (III):

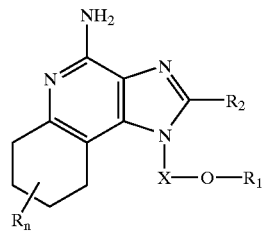

(III)

wherein:
X is —CHR$_3$—, —CHR$_3$-alkyl-, or —CHR$_3$-alkenyl-;
$R_1$ is selected from the group consisting of:
-heteroaryl;
-heterocyclyl;
—$R_4$-heteroaryl; and
—$R_4$-heterocyclyl;
$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

$R_4$ is alkyl or alkenyl, which may be interrupted by one or more —O— groups;
each $R_3$ is independently H or $C_{1-10}$ alkyl;
each Y is independently —O— or —S(O)$_{0-2}$—;
n is 0 to 4; and
each R present is independently selected from the group consisting of $C_{1-10}$ alkyl, $C_{1-10}$ alkoxy, hydroxy, halogen and trifluoromethyl;
or a pharmaceutically acceptable salt thereof.

An additional class of immune response modifying compounds of the invention are tetrahydroimidazoquinoline compounds that have an ether containing substituent at the 1-position, where the ether containing substituent also contains an alkynyl group and a heterocyclyl or heteroaryl group. These compounds are represented by Formula (IV):

(IV)

[Structure of Formula IV: tetrahydroimidazoquinoline with NH$_2$, $R_2$, and X—O—(CH$_2$)$_{1-10}$—C≡CR$_{10}$ substituent, and $R_n$]

wherein:

X is —CHR$_3$—, —CHR$_3$-alkyl-, or —CHR$_3$-alkenyl-;

R$_{10}$ is selected from the group consisting of heteroaryl and heterocyclyl;

R$_2$ is selected from the group consisting of:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from the group, consisting of:
  - —OH;
  - -halogen;
  - —N(R$_3$)$_2$;
  - —CO—N(R$_3$)$_2$;
  - —CO—C$_{1-10}$ alkyl;
  - —CO—O—C$_{1-10}$ alkyl;
  - —N$_3$;
  - -aryl;
  - -heteroaryl;
  - -heterocyclyl;
  - —CO-aryl; and
  - —CO-heteroaryl;

each R$_3$ is independently H or C$_{1-10}$ alkyl;

each Y is independently —O— or —S(O)$_{0-2}$—;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

Preparation of the Compounds

Compounds of the invention can be prepared according to Reaction Scheme I where R, R$_2$, X and n are as defined above and R$_{11}$ is alkyl substituted by a heteroaryl group wherein the heteroaryl group may be unsubstituted or may be substituted as defined infra or R$_{11}$ is substituted heteroaryl as defined infra with the proviso that if R$_{11}$ is substituted heteroaryl at least one substituent is a strong electron withdrawing group located ortho or para to the ether bond.

In Reaction Scheme I a 4-amino-1H-imidazo[4,5-c]quinolin-1-yl alcohol of Formula X is alkylated with a halide of Formula XI to provide a 1H-imidazo[4,5-c]quinolin-4-amine of Formula XII which is a subgenus of Formula I. The alcohol of Formula X is reacted with sodium hydride in a suitable solvent such as N,N-dimethylformamide to form an alkoxide. The halide is then added to the reaction mixture. The reaction can be carried out at ambient temperature or with gentle heating (~50° C.) if desired. The product or a pharmaceutically acceptable salt thereof can be isolated using conventional methods.

Many compounds of Formula X are known, see for example Gerster, U.S. Pat. No. 4,689,338 and Gerster et. al., U.S. Pat. No. 5,605,899, the disclosures of which are incorporated by reference herein; others can readily be prepared using known synthetic routes, see for example, Andre et. al, U.S. Pat. No. 5,578,727; Gerster, U.S. Pat. No. 5,175,296; Nikolaides et al., U.S. Pat. No. 5,395,937; and Gerster et. al., U.S. Pat. No. 5,741,908, the disclosures of which are incorporated by reference herein. Many halides of Formula XI are commercially available; others can be readily prepared using known synthetic methods.

Reaction Scheme I

[Reaction scheme showing compound X reacting with Hal—R$_{11}$ to produce compound XII]

Compounds of the invention can also be prepared according to Reaction Scheme II where R, R$_2$, R$_{11}$, X and n are as defined above.

In step (1) of Reaction Scheme II the hydroxy group of a 1H-imidazo[4,5-c]quinolin-1-yl alcohol of Formula XIII is protected with a benzyl group. The alcohol of Formula XIII is reacted with sodium hydride in a suitable solvent such as N,N-dimethylformamide to form an alkoxide. The alkoxide is then alkylated with benzyl bromide to provide a compound of Formula XIV. The reaction can be carried out at ambient temperature. Many compounds of Formula XIII are known, see for example, Gerster, U.S. Pat. No. 4,689,338; others can readily be prepared using known synthetic routes, see for example, Gerster et al., U.S. Pat. No. 5,605,899 and Gerster, U.S. Pat. No. 5,175,296.

In step (2) of Reaction Scheme II a compound of Formula XIV is oxidized to provide a 1H-imidazo[4,5-c]quinoline-5N-oxide of Formula XV using a conventional oxidizing agent capable of forming N-oxides. Preferably a solution of a compound of Formula XIV in a suitable solvent such as chloroform or dichloromethane is oxidized using 3-chloroperoxybenzoic acid at ambient temperature.

In step (3) of Reaction Scheme II a 1H-imidazo[4,5-c]quinoline-5N-oxide of Formula XV is chlorinated to provide a 4-chloro-1H-imidazo[4,5-c]quinoline of Formula XVI. Preferably a solution of a compound of Formula XV in a suitable solvent such as toluene is treated with phosphorous oxychloride at ambient temperature.

In step (4) of Reaction Scheme II a 4-chloro-1H-imidazo[4,5-c]quinoline of Formula XVI is reacted with phenol to provide a 4-phenoxy-1H-imidazo[4,5-c]quinoline of Formula XVII. The phenol is reacted with sodium hydride in a suitable solvent such as diglyme to form a phenoxide. The phenoxide is then reacted at an elevated temperature with a compound of Formula XVI.

In step (5) of Reaction Scheme II the benzyl protecting group is removed from a compound of Formula XVII to provide a 4-phenoxy-1H-imidazo[4,5-c]quinolin-1-yl alcohol of Formula XVIII. The reaction is preferably carried out by adding triflic acid in a controlled fashion to a solution of a compound of Formula XVII in a suitable solvent such as dichloromethane at ambient temperature.

In step (6) of Reaction Scheme II a 4-phenoxy-1H-imidazo[4,5-c]quinolin-1-yl alcohol of Formula XVIII is alkylated with halide Hal-$R_{11}$ to provide a 4-phenoxy-1H-imidazo[4,5-c]quinolin-1-yl ether of Formula XIX. The alkoxide of a compound of Formula XVIII is formed by adding the alcohol to a biphasic mixture of aqueous 50% sodium hydroxide and an inert solvent such as dichloromethane in the presence of a phase transfer catalyst such as benzyltrimethlammonium chloride. The alkoxide is then alkylated. The reaction can be carried out at ambient temperature.

In step (7) of Reaction Scheme II a 4-phenoxy-1H-imidazo[4,5-c]quinolin-1-yl ether of Formula XIX is aminated to provide a 1H-imidazo[4,5-c]quinolin-4-amine of Formula XII which is a subgenus of Formula I. The reaction can be carried out by combining a compound of Formula XIX with ammonium acetate and heating the resulting mixture at ~150° C. The product or a pharmaceutically acceptable salt thereof can be isolated using conventional methods.

Reaction Scheme II

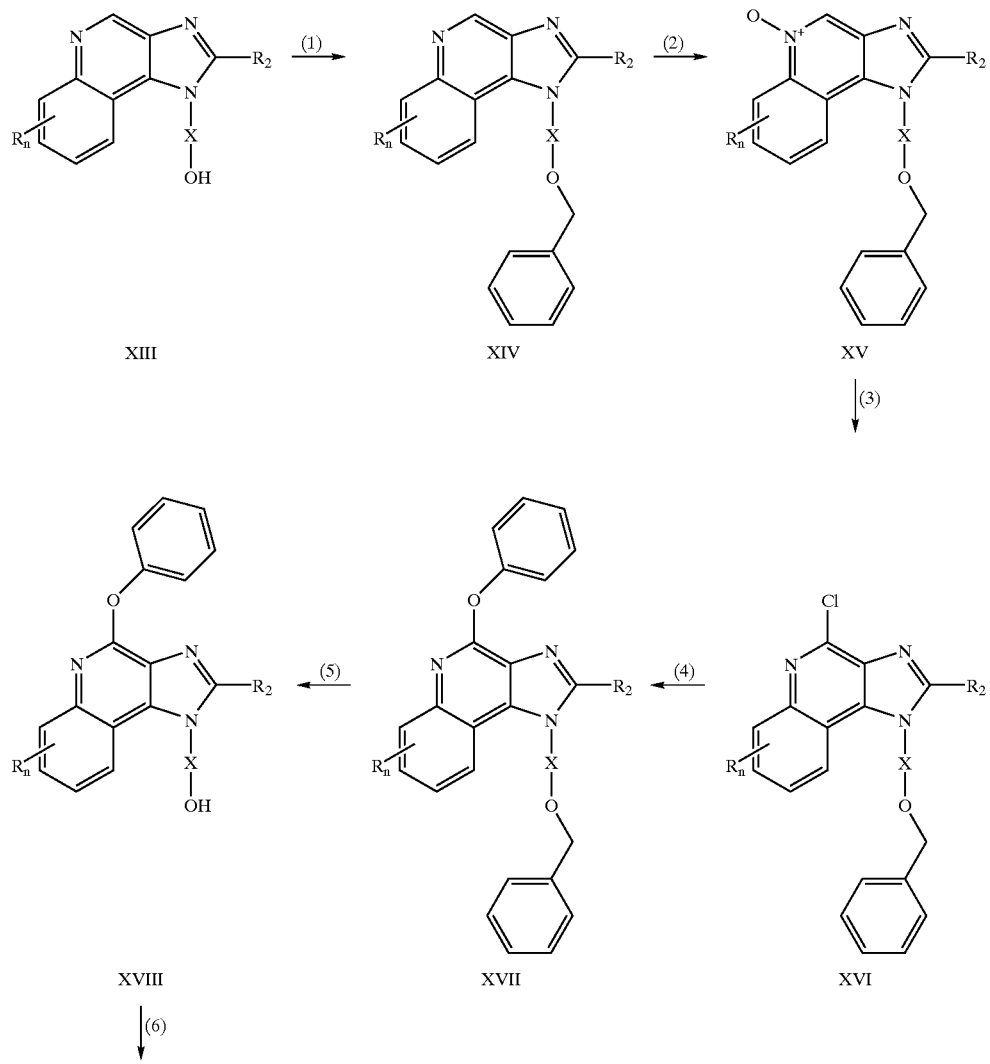

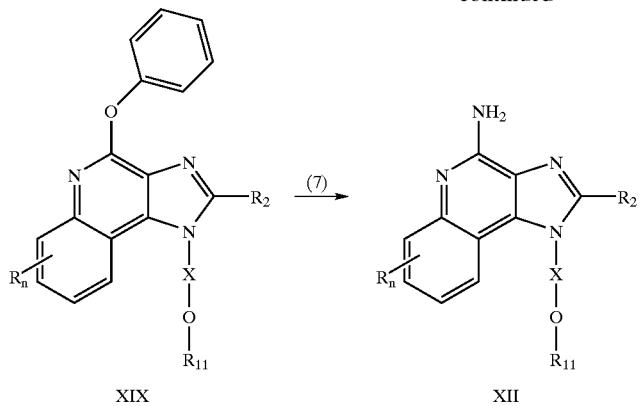

XIX            XII

Tetrahydroimidazoquinolines of the invention can be prepared according to Reaction Scheme III where R, $R_2$, $R_{11}$, X and n are as defined above.

In Reaction Scheme III a 4-amino-6,7,8,9-tetrahydro-1H-imidazo[4,5-c]quinolin-1-yl alcohol of Formula XX is alkylated with a halide of Formula XI to provide a 6,7,8,9-tetrahydro-1H-imidazo[4,5-c]quinolin-4-amine of Formula XXI which is a subgenus of Formula III. The alcohol of Formula XX is reacted with sodium hydride in a suitable solvent such as N,N-dimethylformamide to form an alkoxide. The alkoxide is then combined with the halide. The reaction can be carried out at ambient temperature. The product or a pharmaceutically acceptable salt thereof can be isolated using conventional methods.

Many tetrahydro-1H-imidazo[4,5-c]quinolines of Formula XX are known, see for example, Nikolaides et al., U.S. Pat. No. 5,352,784; others can be prepared using known synthetic methods, see for example, Lindstrom, U.S. Pat. No. 5,693,811; the disclosures of which are incorporated by reference herein.

Reaction Scheme III

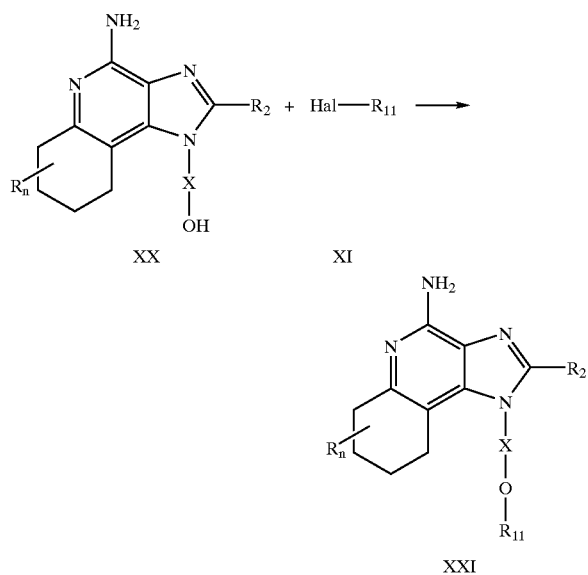

Compounds of the invention can be prepared according to Reaction Scheme IV where R, $R_2$, X and n are as defined above and $R_{12}$ is a heteroaryl group which may be unsubstituted or substituted as defined infra.

In step (1) of Reaction Scheme IV a 1H-imidazo[4,5-c]quinolin-1-yl alcohol of Formula XIII is alkylated with a halide of Formula XXII to provide a 1H-imidazo[4,5-c]quinolin-1-yl ether of Formula XXIII. The compound of Formula XIII and the halide of Formula XXII are combined in a biphasic mixture of 50% aqueous sodium hydroxide and a suitable solvent such as dichloromethane in the presence of a phase transfer catalyst such as benzyltrimethylammonium chloride. The reaction can be run at ambient temperature.

In step (2) of Reaction Scheme IV a 1H-imidazo[4,5-c]quinoline of Formula XXIII is oxidized using the method of step (2) of Reaction Scheme II to provide a 1H-imidazo[4,5-c]quinoline-5N-oxide of Formula XXIV.

In step (3) of Reaction Scheme IV a 1H-imidazo[4,5-c]quinoline-5N-oxide of Formula XXIV is reacted with trichloroacetyl isocyanate to provide a 1H-imidazo[4,5-c]quinolin-4-yl acetamide of Formula XXV. Preferably the isocyanate is added in a controlled fashion at ambient temperature to a solution of the 5N-oxide in a suitable solvent such as dichloromethane.

In step (4) of Reaction Scheme IV a 1H-imidazo[4,5-c]quinolin-4-yl acetamide of Formula XXV is hydrolyzed to provide a 1H-imidazo[4,5-c]quinolin-4-amine of Formula XXVI. The hydrolysis can be carried out by conventional methods preferably by treating a solution of a compound of Formula XXV in methanol with sodium methoxide.

In step (5) of Reaction Scheme IV 1H-imidazo[4,5-c]quinolin-4-amine of Formula XXVI is coupled with a halide of formula Hal-$R_{12}$ using a transition metal catalyst to provide a 1H-imidazo[4,5-c]quinolin-4-amine of Formula XXVII which is a subgenus of Formula II. Preferably a compound of Formula XXVI is combined with the halide in the presence of copper (I) iodide, dichlorobis(triphenylphosphine)palladium(II), and excess triethylamine in a suitable solvent such as N,N-dimethylformamide or acetonitrile. The reaction is preferably carried out at an elevated temperature (60–80° C.). The product or a pharmaceutically acceptable salt thereof can be isolated using conventional methods.

Reaction Scheme IV

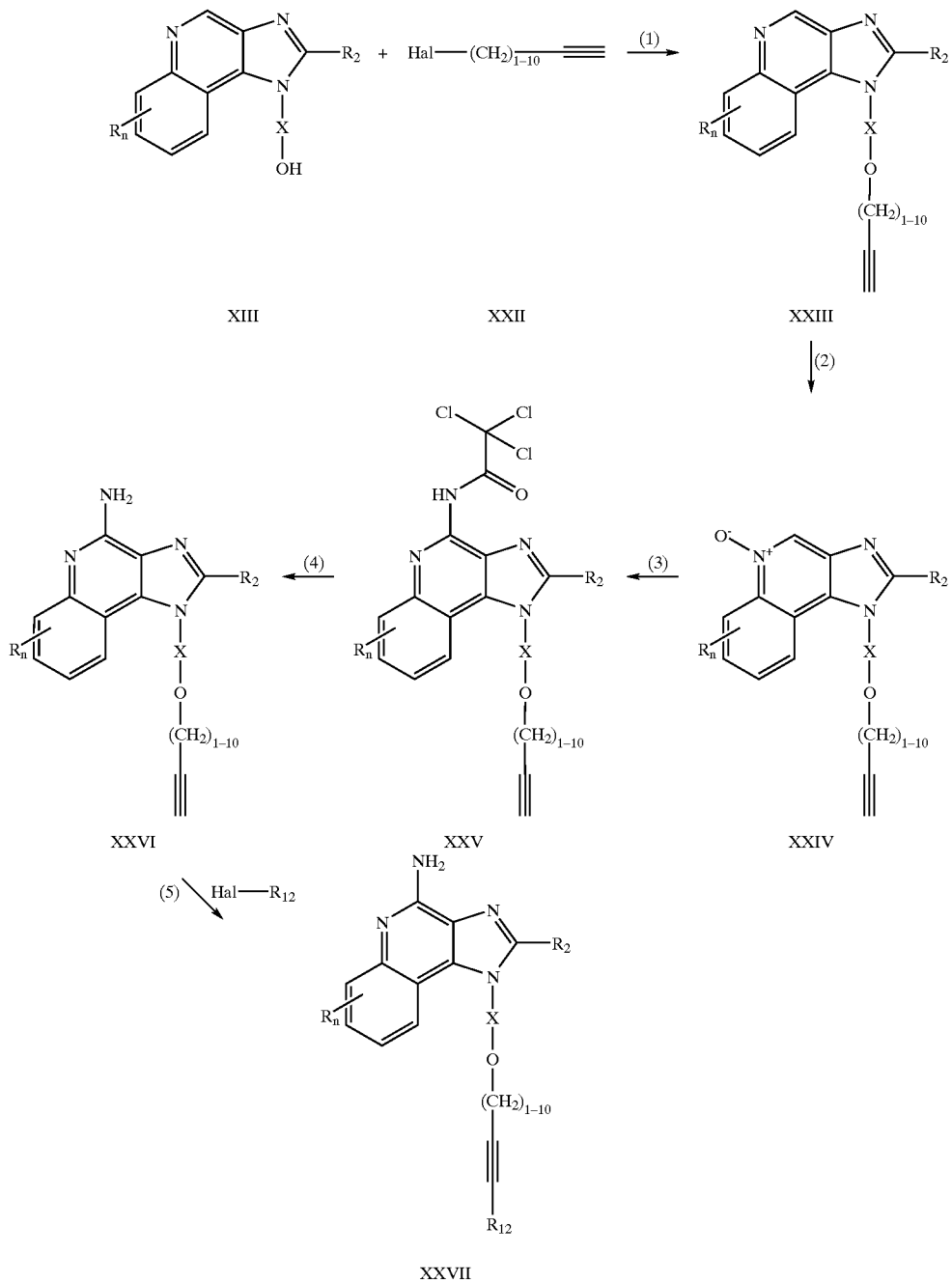

Compounds of the invention can be prepared according to Reaction Scheme V where R, $R_2$, $R_{12}$, X and n are as defined above and BOC is tert-butoxycarbonyl.

In step (1) of Reaction Scheme V the amino group of a 1H-imidazo[4,5-c]quinolin-4-amine of Formula XXVI is protected with tert-butoxycarbonyl groups. A compound of Formula XXVI is combined with di-tert-butyl dicarbonate in a suitable solvent such as N,N-dimethylformamide in the presence of 4-(dimethylamino)pyridine and triethylamine. The reaction is carried out at an elevated temperature (80–85° C.).

In step (2) of Reaction Scheme V a protected 1H-imidazo[4,5-c]quinolin-4-amine of Formula XXVIII is coupled with a halide of formula Hal-$R_{12}$ using a transition metal catalyst to provide a protected 1H-imidazo[4,5-c]quinolin-4-amine of Formula XXIX. Preferably a compound of Formula XXVIII is combined with the halide in the presence of copper (I) iodide, dichlorobis(triphenylphosphine)palladium (II), and excess triethylamine in a suitable solvent such as N,N-dimethylformamide or acetonitrile. The reaction can be carried out at ambient temperature or at an elevated temperature (40–80° C.).

In step (3) of Reaction Scheme V the protecting groups are removed by hydrolysis under acidic conditions to provide a 1H-imidazo[4,5-c]quinolin-4-amine of Formula XXVII which is a subgenus of Formula II. Preferably a compound of Formula XXIX is treated with trifluoroacetic acid in a suitable solvent such as dichloromethane. The reaction can be run at ambient temperature or at a reduced temperature (0° C.). The product or a pharmaceutically acceptable salt thereof can be isolated using conventional methods.

In step (4) of Reaction Scheme V the alkyne bond of a protected 1H-imidazo[4,5-c]quinolin-4-amine of Formula XXIX is reduced to provide a protected 1H-imidazo[4,5-c]quinolin-4-amine of Formula XXX. Preferably, the reduction is carried out using a conventional heterogeneous hydrogentation catalyst such as platinum oxide, platinum on carbon or palladium on carbon. The reaction can conveniently be carried out on a Parr apparatus in a suitable solvent such as methanol.

In step (5) of Reaction Scheme V the protecting groups of a compound of Formula XXX are removed in the same manner as in step (3) to provide a 1H-imidazo[4,5-c]quinolin-4-amine of Formula XXXI which is a subgenus of Formula I. The product or a pharmaceutically acceptable salt thereof can be isolated using conventional methods.

In step (1) of Reaction Scheme VI the amino group of a 1H-imidazo[4,5-c]quinolin-4-amine of Formula XXVI is protected with benzyloxycarbonyl groups. A compound of Formula XXVI is combined with dibenzyl dicarbonate in a suitable solvent such as N,N-dimethylformamide. The reaction can be carried out at ambient temperature or with mild heating (40° C.).

In step (2) of Reaction Scheme VI a protected 1H-imidazo[4,5-c]quinolin-4-amine of Formula XXXII is coupled with a halide of formula Hal-$R_{12}$ using a transition metal catalyst to provide a protected 1H-imidazo[4,5-c]quinolin-4-amine of Formula XXXIII. Preferably a compound of Formula XXXII is combined with the halide in the presence of copper (I) iodide, dichlorobis(triphenylphosphine)palladium(II), and excess triethylamine in a suitable solvent such as N,N-dimethylformamide or acetonitrile. The reaction can be carried out at ambient temperature or at an elevated temperature (40–80° C.).

In step (3) of Reaction Scheme VI the protecting groups are removed by hydrolysis to provide a 1H-imidazo[4,5-c]quinolin-4-amine of Formula XXVII which is a subgenus of

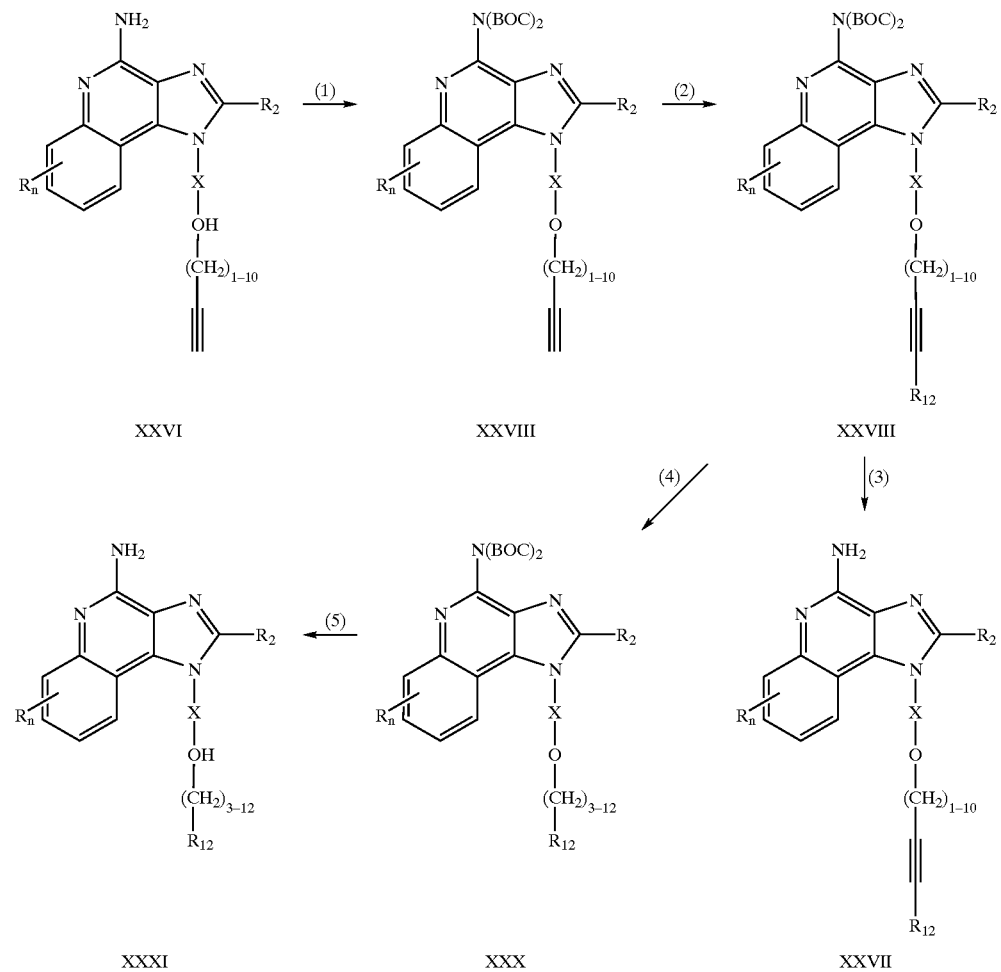

Reaction Scheme V

Compounds of the invention can be prepared according to Reaction Scheme VI where R, $R_2$, $R_{12}$, X and n are as defined above and CBZ is benzyloxycarbonyl.

Formula II. Preferably a compound of Formula XXXIII is treated with sodium methoxide in a suitable solvent such as methanol. The reaction can be run at ambient temperature.

The product or a pharmaceutically acceptable salt thereof can be isolated using conventional methods.

In step (4) of Reaction Scheme VI the protecting groups of a compound of Formula XXXIII are removed by hydrogenolysis and the alkyne bond is reduced to provide a 1H-imidazo[4,5-c]quinolin-4-amine of Formula XXXI which is a subgenus of Formula I. Preferably, the hydrogenolysis/reduction is carried out using palladium hydroxide on carbon. The reaction can conveniently be carried out on a Parr apparatus in a suitable solvent such as methanol. The product or a pharmaceutically acceptable salt thereof can be isolated using conventional methods.

In step (2) of Reaction Scheme VII a 2-chloro-3-nitroquinolin-4-amine of Formula XXXV is reduced to provide a 2-chloroquinoline-3,4-diamine of Formula XXXVI. Preferably, the reduction is carried out using a conventional heterogeneous hydrogenation catalyst such as platinum on carbon or palladium on carbon. The reaction can conveniently be carried out on a Parr apparatus in a suitable solvent such as isopropyl alcohol or toluene.

In step (3) of Reaction Scheme VII a 2-chloroquinoline-3,4-diamine of Formula XXXVI is is reacted with a carboxylic acid or an equivalent thereof to provide a 4-chloro-1H-imidazo[4,5-c]quinoline of Formula XXXVII. Suitable

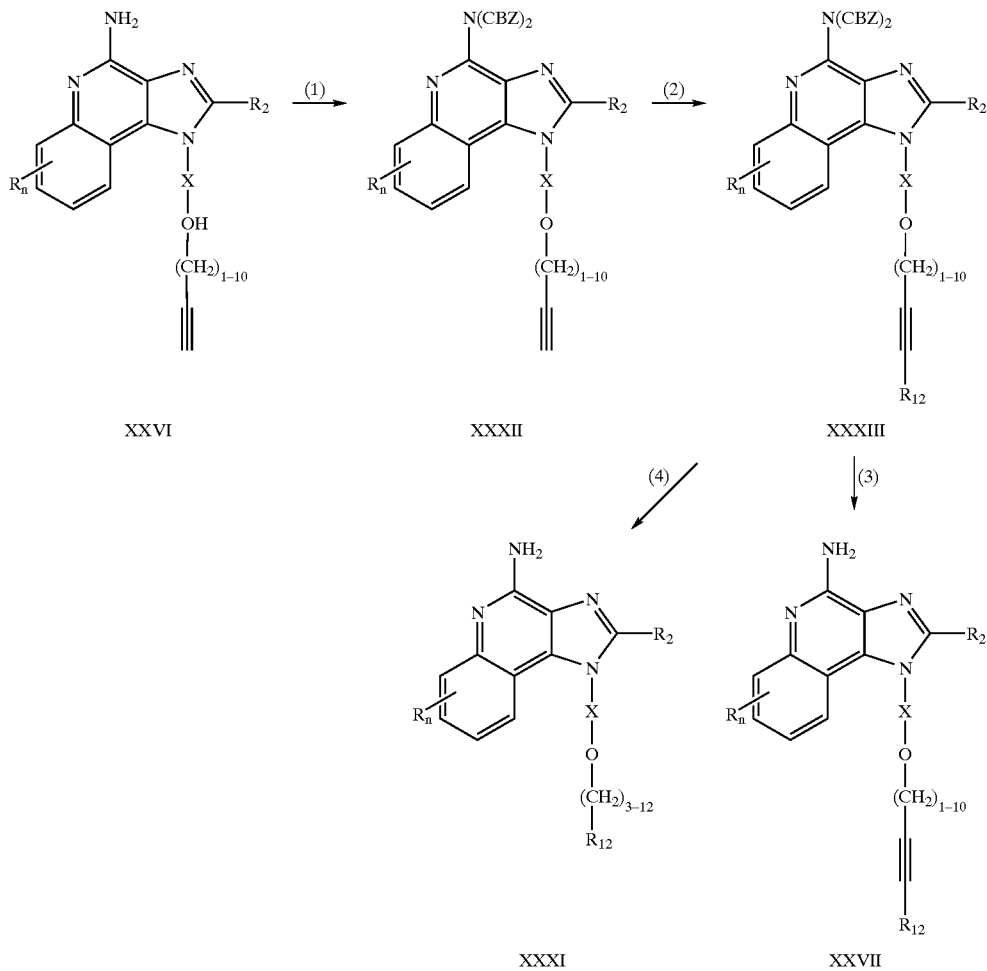

Reaction Scheme VI

Compounds of the invention can be prepared according to Reaction Scheme VII where R, $R_1$, $R_2$, X and n are as defined above.

In step (1) of Reaction Scheme VII a 2,4-dichloro-3-nitroquinoline of Formula XXXIV is reacted with an amine of Formula $R_1$—O—X—$NH_2$ to provide a 2-chloro-3-nitroquinolin-4-amine of Formula XXXV. The reaction can be carried out by adding the amine to a solution of a compound of Formula XXXIV in a suitable solvent such as chloroform or dichloromethane and optionally heating. Many quinolines of Formula XXXIV are known or can be prepared using known synthetic methods (see for example, Andre et al., U.S. Pat. No. 4,988,815 and references cited therein).

equivalents to carboxylic acid include orthoesters, and 1,1-dialkoxyalkyl alkanoates. The carboxylic acid or equivalent is selected such that it will provide the desired $R_2$ substituent in a compound of Formula XXXVII. For example, triethyl orthoformate will provide a compound where $R_2$ is hydrogen and triethyl orthoacetate will provide a compound where $R_2$ is methyl. The reaction can be run in the absence of solvent or in an inert solvent such as toluene. The reaction is run with sufficient heating to drive off any alcohol or water formed as a byproduct of the reaction. Optionally a catalyst such as pyridine hydrochloride can be included.

Alternatively, step (3) can be carried out by (i) reacting the diamine of Formula XXXVI with an acyl halide of Formula $R_2C(O)Cl$ and then (ii) cyclizing. In part (i) the acyl halide is added to a solution of the diamine in an inert solvent such as acetonitrile, pyridine or dichloromethane. The reaction can be carried out at ambient temperature. In part (ii) the product of part (i) is heated in an alcoholic solvent in the presence of a base. Preferably the product of part (i) is refluxed in ethanol in the presence of an excess of triethylamine or heated with methanolic ammonia. Alternatively, if step (i) has been run in pyridine, step (ii) can be carried out by heating the reaction mixture after analysis indicates that step (i) is complete.

In step (4) of Reaction Scheme VII a 4-chloro-1H-imidazo[4,5-c]quinoline of Formula XXXVII is aminated to provide a 1H-imidazo[4,5-c]quinolin4-amine of Formula I. The reaction is carried out by heating (e.g.,125–175° C.) a compound of Formula XXXVII under pressure in a sealed reactor in the presence of a solution of ammonia in an alkanol. The product or a pharmaceutically acceptable salt thereof can be isolated using conventional methods.

Many 1H-imidazo[4,5-c]quinolin-4-amines of Formula XXXVIII are known; others may be prepared using known synthetic methods, see for example, Gerster, U.S. Pat. No. 5,756,747 and the references cited therein.

Reaction Scheme VIII

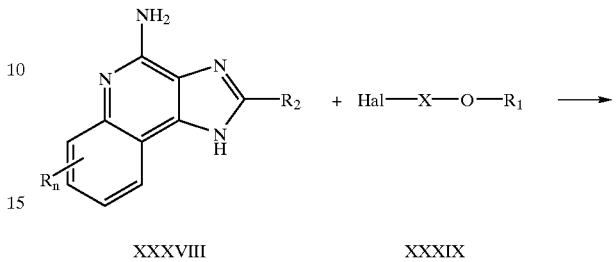

Reaction Scheme VII

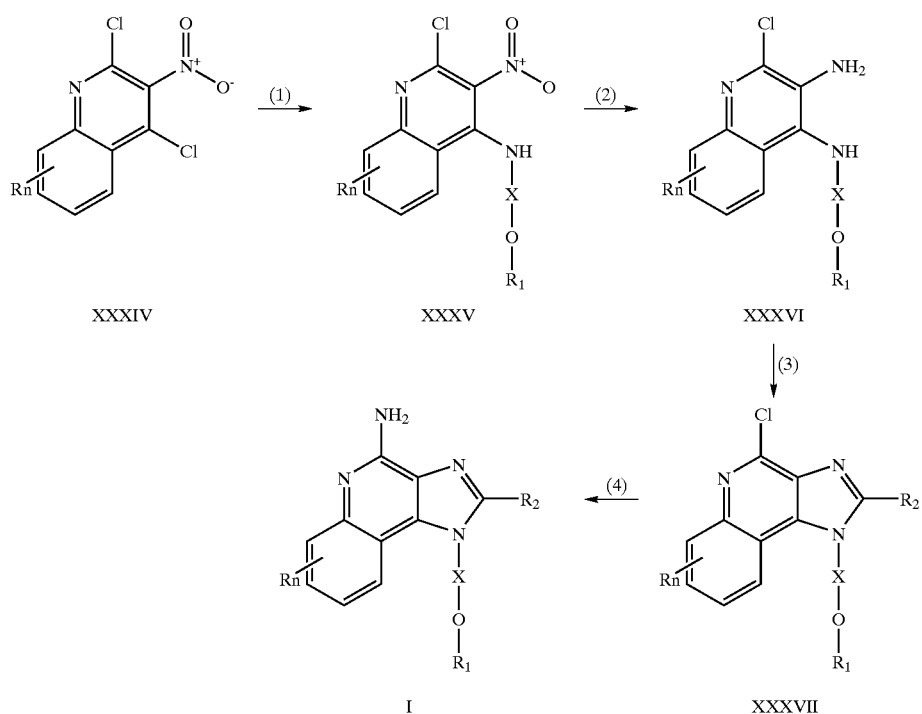

Compounds of the invention can be prepared according to Reaction Scheme VIII where R, $R_1$, $R_2$, X and n are as defined above.

In Reaction Scheme VIII a 1H-imidazo[4,5-c]quinolin-4-amine of Formula XXXVIII is alkylated with a halide of Formula XXXIX to provide a 1H-imidazo[4,5-c]quinolin-4-amine of Formula I. The compound of Formula XXXVIII is reacted with sodium hydride in a suitable solvent such as N,N-dimethylformamide. The halide is then added to the reaction mixture. The reaction can be carried out at an elevated temperature (~100° C.). Alkylation occurs at both the $N^1$ and the $N^3$ nitrogens; however, the desired 1-isomer can be readily separated from the 3-isomer using conventional techniques such as column chromatography and recrystallization.

-continued

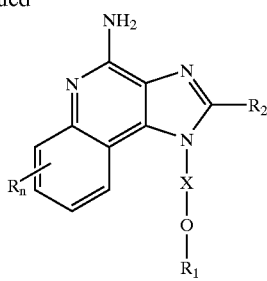

Compounds of the invention can be prepared according to Reaction Scheme IX where R, $R_1$ $R_2$, X and n are as defined above.

In step (1) of Reaction Scheme IX a 4-nitrotetrazolo[1,5-a]quinolin-5-ol of Formula XL is chlorinated to provide a 5-chloro-4-nitrotetrazolo[1,5-a]quinoline of Formula XLI. Conventional chlorinating agents can be used. Preferably the reaction is carried out using phosphorus oxychloride in a suitable solvent such as N,N-dimethylformamide. 4-Nitrotetrazolo[1,5-a]quinolin-5-ols of Formula XL are known or can be prepared using known synthetic methods (see for example, Gerster, et al., U.S. Pat. No. 5,741,908 and references cited therein).

In step (2) of Reaction Scheme IX a 5-chloro-4-nitrotetrazolo[1,5-a]quinoline of Formula XLI is reacted with an amine of Formula $R_1$—O—X—$NH_2$ to provide a 4-nitrotetrazolo[1,5-a]quinolin-5-amine of Formula XLII. The reaction can be carried out by adding the amine to a solution of a compound of Formula XLI in a suitable solvent such as dichloromethane in the presence of triethylamine.

In step (3) of Reaction Scheme IX a 4-nitrotetrazolo[1,5-a]quinolin-5-amine of Formula XLII is reduced using the method of step (2) in Reaction Scheme VII to provide a tetrazolo[1,5-a]quinolin-4,5-diamine of Formula XLIII.

In step (4) of Reaction Scheme IX a tetrazolo[1,5-a]quinolin-4,5-diamine of Formula XLIII is cyclized using the method of step (3) in Reaction Scheme VII to provide a 6H-imidazo[4,5-c]tetrazolo[1,5-a]quinoline of Formula XLIV.

In step (5) of Reaction Scheme IX a 6H-imidazo[4,5-c]tetrazolo[1,5-a]quinoline of Formula XLIV is reduced to provide a 1H-imidazo[4,5-c]quinolin-4-amine of Formula I.

Step (5) involves (i) reacting a compound of Formula XLIV with triphenylphosphine and then (ii) hydrolyzing. Part (i) can be carried out by combining a compound of Formula XLIV with triphenylphosphine in a suitable solvent such as 1,2-dichlorobenzene and heating. Part (ii) involves hydrolysis of the product from part (i). The hydrolysis can be carried out by conventional methods such as heating in the presence of water or a lower alkanol optionally in the presence of a catalyst such as an alkali metal hydroxide or lower alkoxide. The product or a pharmaceutically acceptable salt thereof can be isolated using conventional methods.

Reaction Scheme IX

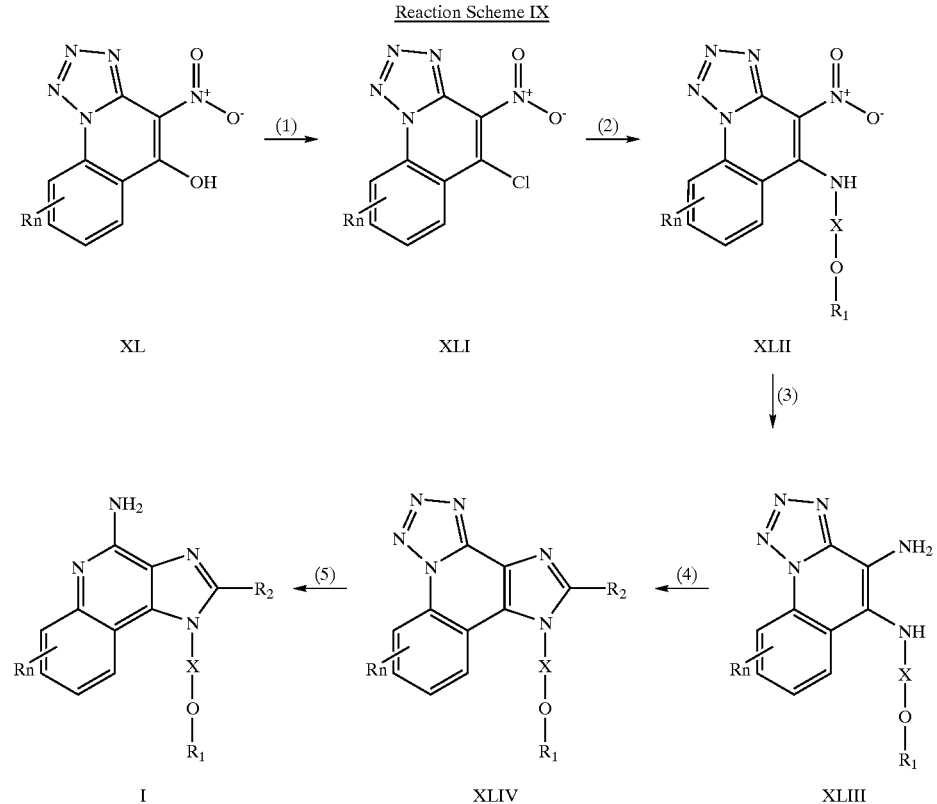

Tetrahydroimidazoquinolines of the invention can be prepared according to Reaction Scheme X where R, $R_2$, $R_{12}$, X and n are as defined above.

In step (1) of Reaction Scheme X a 4-amino-6,7,8,9-tetrahydro-1H-imidazo[4,5-c]quinolin-1-yl alcohol of Formula XX is alkylated using the method of Reaction Scheme III with a halide of formula Hal-$(CH_2)_{1-10}$—CH≡CH to provide a 6,7,8,9-tetrahydro-1H-imidazo[4,5-c]quinolin-4-amine of Formula XLV.

In step (2) of Reaction Scheme X a 6,7,8,9-tetrahydro-1H-imidazo[4,5-c]quinolin-4-amine of Formula XLV is coupled using the method of step (5) of Reaction Scheme IV with a halide of Formula Hal-$R_{12}$ to provide a 6,7,8,9-tetrahydro-1H-imidazo[4,5-c]quinolin-4-amine of Formula XLIV which is a subgenus of Formula IV. The product or a pharmaceutically acceptable salt thereof can be isolated using conventional methods.

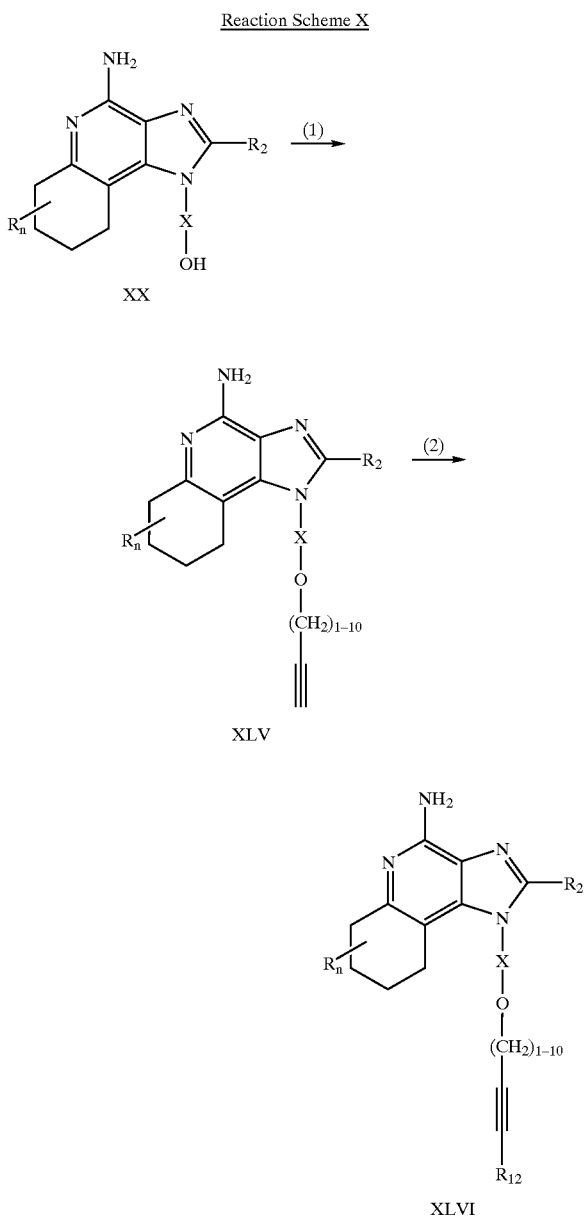

Compounds of the invention can be prepared according to Reaction Scheme XI where R, $R_1$, $R_2$, X and n are as defined above.

In step (1) of Reaction Scheme XI a 2,4-dihydroxy-3-nitro-6,7,8,9-tetrahydroquinoline of Formula XLVII is chlorinated to provide a 2,4-dichloro-3-nitro-6,7,8,9-tetrahydroquinoline of Formula XLVIII. Conventional chlorinating agents can be used. Preferably the reaction is carried out by combining a compound of Formula XLVII with phosphorous oxychloride and then heating (55–65° C.). Compounds of Formula XLVII are known or can be prepared using known synthetic methods (see for example Nikolaides et al,. U.S. Pat. No. 5,352,784 and references cited therein).

In step (2) of Reaction Scheme XI a 2,4-dichloro-3-nitro-6,7,8,9-tetrahydroquinoline of Formula XLVIII is reacted with an amine of Formula $R_1$—O—X—$NH_2$ to provide a 2-chloro-3-nitro-6,7,8,9-tetrahydroquinolin-4-amine of Formula XLIX. The reaction can be carried out by adding the amine to a solution of a compound of Formula XLVIII in a suitable solvent such as N,N-dimethylformamide and heating (55–65° C.).

In step (3) of Reaction Scheme XI a 2-chloro-3-nitro-6,7,8,9-tetrahydroquinolin-4-amine of Formula XLIX is reacted with phenol using the method of step (4) of Reaction Scheme II to provide a 2-phenoxy-3-nitro-6,7,8,9-tetrahydroquinolin-4-amine of Formula L.

In step (4) of Reaction Scheme XI a 2-phenoxy-3-nitro-6,7,8,9-tetrahydroquinolin-4-amine of Formula L is reduced using the method of step (2) of Reaction Scheme VII to provide a 2-phenoxy-6,7,8,9-tetrahydroquinolin-3,4-diamine of Formula LI.

In step (5) of Reaction Scheme XI a 2-phenoxy-6,7,8,9-tetrahydroquinolin-3,4-diamine of Formula LI is cyclized using the method of step (3) of Reaction Scheme VII to provide a 4-phenoxy-6,7,8,9-tetrahydro-1H-imidazo[4,5-c] quinoline of Formula LII.

In step (6) of Reaction Scheme XI a 4-phenoxy-6,7,8,9-tetrahydro-1H-imidazo[4,5-c]quinoline of Formula LII is aminated using the method of step (7) of Reaction Scheme II to provide a 6,7,8,9-tetrahydro-1H-imidazo[4,5-c] quinolin-4-amine of Formula III.

Reaction Scheme XI

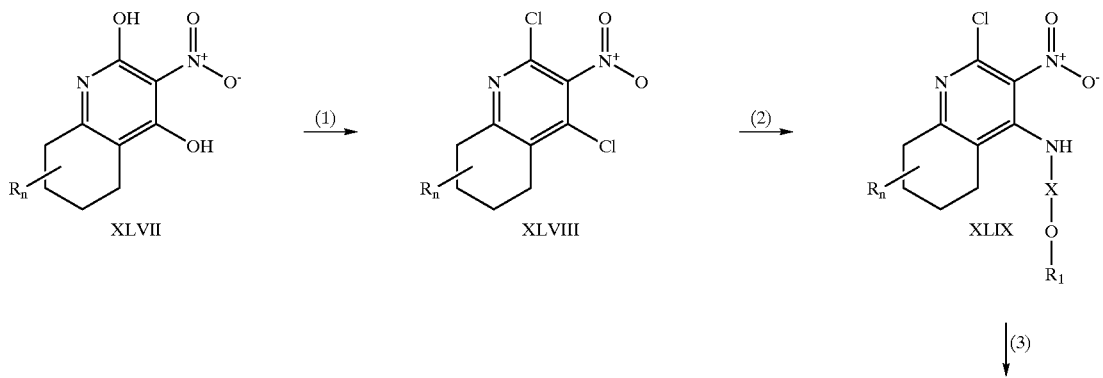

The invention also provides novel compounds useful as intermediates in the synthesis of the compounds of Formulas (I), (II), (III), and (IV). These intermediate compounds have the structural Formulas (V)–(IX) and (XLIV) described in more detail below.

One class of intermediate compounds has Formula (V):

(V)

wherein:

X is —CHR$_3$—, —CHR$_3$-alkyl-, or —CHR$_3$-alkenyl-;

R$_1$ is selected from the group consisting of:
- -heteroaryl;
- -heterocyclyl;
- —R$_4$-heteroaryl;
- —R$_4$-heterocyclyl; and
- —(CH$_2$)$_{1-10}$—C≡C—R$_{10}$;

R$_2$ is selected from the group consisting of:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from the group consisting of:
  - —OH;
  - -halogen;
  - —N(R$_3$)$_2$;
  - —CO—N(R$_3$)$_2$;
  - —CO—C$_{1-10}$ alkyl;
  - —CO—O—C$_{1-10}$ alkyl;
  - —N$_3$;
  - -aryl;
  - -heteroaryl;
  - -heterocyclyl;
  - —CO-aryl; and
  - —CO-heteroaryl;

R$_4$ is alkyl or alkenyl, which may be interrupted by one or more —O— groups;

each R$_3$ is independently H or C$_{1-10}$ alkyl;

R$_{10}$ is heteroaryl or heterocyclyl;

each Y is independently —O— or —S(O)$_{0-2}$—;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

Another class of intermediates are imidazoquinoline-4-phenoxy compounds of Formula (VI):

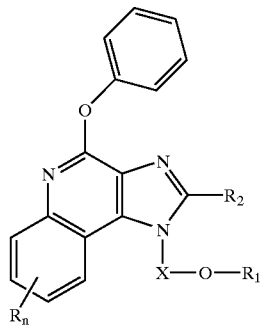

(VI)

wherein:

X is —CHR$_3$—, —CHR$_3$-alkyl-, or —CHR$_3$-alkenyl-;

R$_1$ is selected from the group consisting of:
-heteroaryl;
-heterocyclyl;
—R$_4$-heteroaryl;
—R$_4$-heterocyclyl; and
—(CH$_2$)$_{1-10}$—C≡C—R$_{10}$, R$_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;

R$_4$ is alkyl or alkenyl, which may be interrupted by one or more —O— groups;

each R$_3$ is independently H or C$_{1-10}$ alkyl;

R$_{10}$ is heteroaryl or heterocyclyl;

each Y is independently —O— or —S(O)$_{0-2}$—;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

Another class of intermediate compounds is represented by Formula (VII):

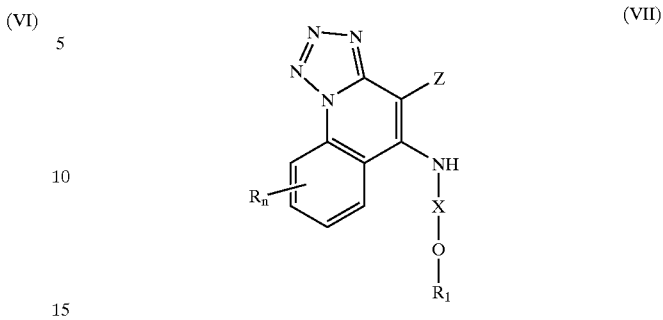

(VII)

wherein:
Z is NH$_2$ or NO$_2$;
X is —CHR$_3$—, —CHR$_3$-alkyl-, or CHR$_3$-alkenyl-;
R$_1$ is selected from the group consisting of:
-heteroaryl;
-heterocyclyl;
—R$_4$-heteroaryl; and
—R$_4$-heterocyclyl;
R$_4$ is alkyl or alkenyl, which may be interrupted by one or more —O— groups;
each R$_3$ is independently H or C$_{1-10}$ alkyl;
n is 0 to 4; and
each R present is independently selected from the group consisting of C$_{1-10}$ alkyl, C$_{1-10}$ alkoxy, hydroxy, halogen and trifluoromethyl;
or a pharmaceutically acceptable salt thereof.

Another class of intermediate compounds has the Formula (XLIV):

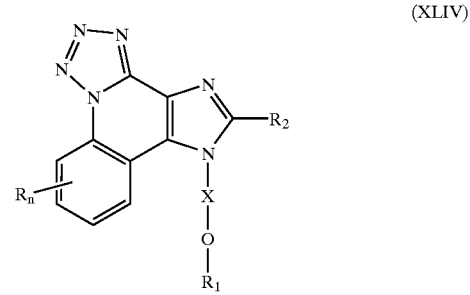

(XLIV)

wherein:
X is —CHR$_3$—, —CHR$_3$-alkyl-, or —CHR$_3$-alkenyl-;
R$_1$ is selected from the group consisting of:
-heteroaryl;
-heterocyclyl;
—R$_4$-heteroaryl; and
—R$_4$-heterocyclyl;
R$_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N(R$_3$)$_2$;
—CO—N(R$_3$)$_2$;

—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

$R_4$ is alkyl or alkenyl, which may be interrupted by one or more —O— groups;

each $R_3$ is independently H or $C_{1-10}$ alkyl;

each Y is independently —O— or —S(O)$_{0-2}$—;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

An additional class of intermediate compounds has the Formula (VIII):

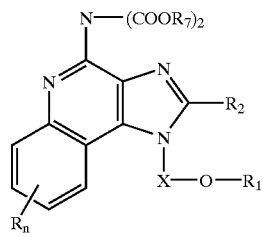

(VIII)

wherein:

X is —$CHR_3$—, —$CHR_3$-alkyl-, or —$CHR_3$-alkenyl-;

$R_1$ is selected from the group consisting of:
-heteroaryl;
-heterocyclyl;
—$R_4$-heteroaryl; and
—$R_4$-heterocyclyl;

$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—$N(R_3)_2$;
—CO—$N(R_3)_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

$R_4$ is alkyl or alkenyl, which may be interrupted by one or more —O— groups;

each $R_3$ is independently H or $C_{1-10}$ alkyl;

each Y is independently —O— or —S(O)$_{0-2}$—;

n is 0 to 4;

each R present is independently selected from the group consisting of $C_{1-10}$ alkyl, $C_{1-10}$ alkoxy, hydroxy, halogen and trifluoromethyl; and $R_7$ is tert-butyl or benzyl;

or a pharmaceutically acceptable salt thereof.

A further class of intermediates are imidazoquinoline-4-chloro compounds of the Formula (IX)

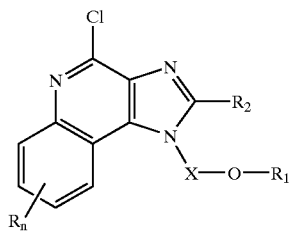

(IX)

wherein:

X is —$CHR_3$—, —$CHR_3$-alkyl-, or —$CHR_3$-alkenyl-;

$R_1$ is selected from the group consisting of:
-heteroaryl;
-heterocyclyl;
—$R_4$-heteroaryl; and
—$R_4$-heterocyclyl;

$R_2$ is selected from the group consisting of:
-hydrogen;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—$N(R_3)_2$;
—CO—$N(R_3)_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

$R_4$ is alkyl or alkenyl, which may be interrupted by one or more —O— groups;

each $R_3$ is independently H or $C_{1-10}$ alkyl;

each Y is independently —O— or —S(O)$_{0-2}$—;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

As used herein, the terms "alkyl", "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, and adamantyl.

In addition, the alkyl and alkenyl portions of —X— groups can be unsubstituted or substituted by one or more substituents, which substituents are selected from the group consisting of alkyl, alkenyl, aryl, heteroaryl, heterocyclyl, arylalkyl, heteroarylalkyl, and heterocyclylalkyl.

The term "haloalkyl" is inclusive of groups that are substituted by one or more halogen atoms, including perfluorinated groups. This is also true of groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, quinoxalinyl, benzimidazolyl, benzothiazolyl, naphthyridinyl, isoxazolyl, isothiazolyl, quinazolinyl, purinyl, and so on.

"Heterocyclyl" includes non-aromatic rings or ring systems that contain at least one ring hetero atom (e.g., O, S, N) and includes the fully saturated and partially unsaturated derivatives of any of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, and the like.

The aryl, heteroaryl, and heterocyclyl groups can be unsubstituted or substituted by one or more substituents independently selected from the group consisting of alkyl, alkoxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, aroyloxy, aroylthio, aroylamino, alkylaminosulfonyl, alkylsulfonyl, arylsulfonyl, heteroarylsulfonyl, aryldiazinyl, alkylsulfonylamino, alkylenesulfonylamino, arylsulfonylamino, arylalkylsulfonylamino,heteroarylsulfonylamino, heteroalkylsulfonylamino, alkylcarbonylamino, alkenylcarbonylamino, arylcarbonylamino, arylalkylcarbonylamino, heteroarylcarbonylamino, heteroarylalkylcarbonylamino, alkylaminocarbonylamino, alkenylaminocarbonylamino, arylaminocarbonylamino, arylalkylaminocarbonylamino, heteroarylaminocarbonylamino, herteroarylalkylaminocarbonylamino, but, in the case of heterocyclyl, alkylcarbonyl, alkenylcarbonyl, haloalkylcarbonyl, arylcarbonyl, heteroarylcarbonyl, alkylthiocarbonyl, arylthiocarbonyl, heteroarylcarbonyl, alkylaminosulfonyl, alkylsulfonyl, arylsulfonyl, and heteroarylsulfonyl are not permitted. If any other groups are identified as being "substituted" or "optionally substituted", then those groups can also be substituted by one or more of the above enumerated substituents.

Certain substituents are generally preferred. For example, preferred heteroaryl groups include 2-pyridine, 3-pyridine, 4-pyridine, 2-pyrimidine, and 5-pyrimidine. Preferably no R substituents are present (i.e., n is 0). Preferred $R_2$ groups include hydrogen, alkyl groups having 1 to 4 carbon atoms (i.e., methyl, ethyl, propyl, isopropyl, n-butyl, sec-butyl, isobutyl, and cyclopropylmethyl), methoxyethyl, and ethoxymethyl. One or more of these preferred substituents, if present, can be present in the compounds of the invention in any combination.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers.

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" means an amount of the compound sufficient to induce a therapeutic effect, such as cytokine induction, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 ng/kg to about 50 mg/kg, preferably about 10 μg/kg to about 5 mg/kg, of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and tumors. Accordingly, the invention provides a method of inducing cytokine biosynthesis in an animal comprising administering an effective amount of a compound or composition of the invention to the animal.

Certain compounds of the invention have been found to preferentially induce the expression of IFN-α in a population of hematopoietic cells such as PBMCs (peripheral blood mononuclear cells) containing pDC2 cells (precursor dendritic cell-type 2) without concomitant production of significant levels of inflammatory cytokines.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the Th1 response and/or downregulation of the Th2 response is desired. In view of the ability of compounds of the invention to inhibit the Th2 immune response, the compounds are expected to be useful in the treatment of atopic diseases, e.g., atopic dermatitis, asthma, allergy, allergic rhinitis; systemic lupus erythematosis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Virus Type I and Type II; molluscum contagiosum; variola, particularly variola major; rhinovirus; adenovirus; influenza; para-influenza; HIV; CMV; VZV; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, and leishmaniasis; and bacterial infections, e.g., tuberculosis, and mycobacterium avium. Additional diseases or conditions that can be treated using the compounds of the invention include actinic keratosis; eczema; eosinophilia; essential thrombocythaemia; leprosy; multiple sclerosis; Ommen's syndrome; discoid lupus; Bowen's disease; Bowenoid papulosis; alopecia areata; the inhibition of keloid formation after surgery and other types of post-surgical scars. In addition, these compounds could enhance or stimulate the healing of wounds, including chronic wounds. The compounds may be useful for treating the opportunistic infections and tumors that occur after suppression of cell mediated immunity in, for example, transplant patients, cancer patients and HIV patients.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of about 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

The invention is further described by the following examples, which are provided for illustration only and are not intended to be limiting in any way.

In the examples below some of the compounds were purified using semi-preparative HPLC. Two different methods were used and they are described below. Both methods used a A-100 Gilson-6 equipped with 900 Series Intelligent Interface. The semi-prep HPLC fractions were analyzed by LC-APCI/MS and the appropriate fractions were combined and lyophilized to provide the trifluoroacetate salt of the desired compound.

Method A

Column: column Microsorb C18, 21.4×250 mm, 8 micron particle size, 60 Å pore; flow rate: 10 mL/min.; gradient elution from 2–95% B in 25 min., hold at 95% B for 5 min., where A=0.1% trifluoroacetic acid/water and B=0.1% trifluoroacetic acid/acetonitrile; peak detection at 254 nm for triggering fraction collection.

Method B

Column: Phenomenex Capcell PakC18, 35×20 mm, 5 micron particle size; flow rate: 20 mL/min.; gradient elution from 5–95% B in 10 min., hold at 95% B for 2 min., where A=0.1% trifluoroacetic acid/water and B=0.1% trifluoroacetic acid/acetonitrile; peak detection at 254 nm for triggering fraction collection.

EXAMPLE 1

1-(2-{[3-(Isoquinolin-4-yl)-2-propynyl]oxy}ethyl)-1H-imidazo[4,5-c]quinolin-4-amine

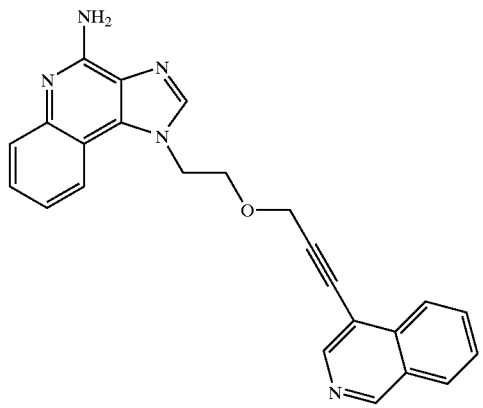

Part A 2-(1H-Imidazo[4,5-c]quinolin-1-yl)-1-ethanol (28.5 g, 0.133 mol) was added in portions over a period of 1 hour to a mixture of sodium hydroxide (240 mL of 50%), dichloromethane (240 mL), propargyl bromide (39.6 g of 80%, 0.266 mol) and benzyltrimethylammonium chloride (2.46 g, 0.013 mmol). The resulting reaction mixture was allowed to stir at ambient temperature for 16 hours at which time the reaction mixture was homogeneous. The layers were separated. The aqueous fraction was extracted with additional dichloromethane. The organic fractions were combined, washed with water, dried over magnesium sulfate and then concentrated under reduced pressure. The resulting residue was combined with diethyl ether and the mixture was allowed to stir. An orange solid was isolated by filtration. This material was recrystallized from ethyl acetate to provide 19.8 g of 2-(1H-imidazo[4,5-c]quinolin-1-yl)ethyl (2-propynyl) ether as a yellow crystalline solid, m.p. 124–126° C.

Analysis. Calculated for $C_{15}H_{13}N_3O$: %C, 71.70; %H, 5.21; %N, 16.72. Found: %C, 71.85; %H, 5.25; %N, 16.90

$^1$H NMR (300 MHz, DMSO) δ 9.21 (s, 1 H), 8.44 (m, 1 H), 8.36 (s, 1H), 8.18 (m, 1 H), 7.71 (m, 2 H), 4.93 (t, J=5.1 Hz, 2 H), 4.14 (d, J=2.4 Hz, 2 H), 3.98 (t, J=5.1 Hz, 2 H), 3.35 (t, J=2.2 Hz, 1 H)

HRMS(ESI) calcd for $C_{15}H_{14}N_3O$ (MH$^+$) 252.1137, found 252.1141

Part B 2-(1H-Imidazo[4,5-c]quinolin-1-yl)ethyl (2-propynyl) ether (19.7 g, 78.4 mmol) and chloroform were combined and then cooled to 0° C. 3-Chloroperoxybenzoic acid (15.7 g of 57–86%) was added and the mixture was allowed to stir for 0.5 hour. The mixture was allowed to warm to ambient temperature by which time all material was in solution. Analysis by thin layer chromatography (TLC) indicated that some starting material was still present so more 3-chloroperoxybenzoic acid (two separate 4 g portions) was added. About 0.5 hour after the second portion was added, TLC showed no starting material. The reaction solution was extracted with 10% sodium hydroxide. The aqueous fraction was then extracted multiple times with dichloromethane. The organic fractions were combined, dried over magnesium sulfate, filtered and then concentrated under reduced pressure to provide 18.5 g of 1-[2-(2-propynyloxy)ethyl]-1H-imidazo[4,5-c]quinoline-5N-oxide as a yellow oil.

HRMS(ESI) calcd for $C_{15}H_{14}N_3O_2$ (MH$^+$) 268.1086, found 268.1098

Part C

Under a nitrogen atmosphere trichloroacetyl isocyanate (15.5 g, 82.2 mmol) was added dropwise to a mixture of 1-[2-(2-propynyloxy)ethyl]-1H-imidazo[4,5-c]quinoline-5N-oxide (18.3 g, 68.5 mmol) and dichloromethane (300 mL). Vigorous carbon dioxide evolution was observed. After about 0.5 hour all of the material was in solution. The reaction solution was allowed to stir for about 1 hour at which time analysis by TLC indicated the presence of a small amount of starting material. More trichloroacetyl isocyanate (4.5 g) was added. After 1 hour, TLC analysis indicated that the reaction was complete. The volatiles were removed under reduced pressure to provide N-{1-[2-(2-propynyloxy)ethyl]-1H-imidazo[4,5-c]quinolin-4-yl}-2,2,2-trichloroacetamide as a pale yellow solid.

Part D

Dichloromethane (150 mL) was added to a mixture of the solid from Part C and methanol (200 mL) and all of the material went into solution. Sodium methoxide (50 g of 25% in methanol) was added and the solution was allowed to stir at ambient temperature overnight. The resulting precipitate was isolated by filtration. The filtrate was concentrated to a volume of approximately 100 mL and a second crop of precipitate was isolated by filtration. The two crops were combined and dried in a vacuum oven at 60° C. for 16 hours to provide 16.4 g of 1-[2-(2-propynyloxy)ethyl]-1H-imidazo[4,5-c]quinolin-4-amine as an off-white solid, m.p. 225–227° C.

Analysis. Calculated for $C_{15}H_{14}N_4O$ $(H_2O)_{1/4}$: %C, 66.53; %H, 5.40; %N, 20.69. Found: %C, 66.33; %H, 5.18; %N, 21.12

$^1$H NMR (300 MHz, DMSO) δ 8.13 (s, 1 H), 8.08 (br d, J=7.8 Hz, 1 H), 7.62 (br d, J=8.3 Hz, 1 H), 7.44 (br t, J=7.6 Hz, 1 H), 7.24 (br t, J=7.5 Hz, 1 H), 6.54 (s, 2 H), 4.81 (t, J=5.4Hz, 2 H), 4.14 (d, J=2.4Hz, 2 H), 3.93 (t, J=5.1 Hz, 2 H), 3.38 (t, J=2.4 Hz, 1 H)

HRMS(ESI) calcd for $C_{15}H_{15}N_4O$ (MH$^+$) 267.1246, found 267.1253

Part E

Under a nitrogen atmosphere 1-[2-(2-propynyloxy)ethyl]-1H-imidazo[4,5-c]quinolin-4-amine (16 g, 60.1 mmol), di-tert-butyl dicarbonate (32.7 g, 150 mmol), triethylamine (21 mL, 150 mol), N,N-dimethylformamide (150 mL) and 4-(dimethylamino)pyridine (0.1 g) were combined and heated to 80–85° C. After about 1 hour the mixture became homogeneous and TLC analysis indicated that very little starting material remained. The solution was heated for an additional hour. The solution was diluted with ethyl acetate and water. The layers were separated and the aqueous fraction was extracted with ethyl acetate. The organic fractions were combined, washed with water and then with brine, dried over magnesium sulfate, filtered and then concentrated under reduced pressure to provide a pale orange-yellow solid. This material was triturated with diethyl ether to provide 22.6 g of N,N-(bis tert-butoxycarbonyl)-1-[2-(2-propynyloxy)ethyl]-1H-imidazo[4,5-c]quinolin-4-amine as an off-white solid, m.p. 139–142° C.

Analysis. Calculated for $C_{25}H_{30}N_4O_5$: %C, 64.36; %H, 6.48; %N, 12.01. Found: %C, 64.40; %H, 6.43; %N, 12.06

$^1$H NMR (300 MHz, DMSO) δ 8.44 (m, 1 H), 8.35 (s, 1 H), 8.08 (m, 1 H), 7.73 (m, 2 H), 4.94 (t, J=4.9 Hz, 2 H), 4.12 (d, J=2.4 Hz, 2 H), 3.98 (t, J=5.1 Hz, 2 H), 3.31 (t, J=2.4 Hz, 1 H), 1.34 (s, 18 H)

HRMS(ESI) calcd for $C_{25}H_{31}N_4O_5$ (MH$^+$) 467.2294, found 467.2307

Part F

Under a nitrogen atmosphere N,N-(bis tert-butoxycarbonyl)-1-[2-(2-propynyloxy)ethyl]-1H-imidazo[4,5-c]quinolin-4-amine (1.0 g, 2.14 mmol), triethylamine (0.8 mL, 5.56 mmol) and N,N-dimethylformamide (25 mL) were combined and the resulting solution was heated to 80–85° C. Dichlorobis(triphenylphosphine)palladium(II) (0.08 g, 0.11 mol), copper(I) iodide (0.04 g, 0.21 mmol) and 4-bromoisoquinoline (0.49 g, 2.35 mmol) were added. After 3 hours analysis by high performance liquid chromatography (reverse phase with an acetonitrile/water gradient) indicated that the reaction was complete. The reaction solution was slowly poured into water with vigorous stirring. A cream colored precipitate was isolated by filtration, washed with water and then dried in a vacuum oven (<40° C.) for 16 hours to provide 1.21 g of N,N-(bis tert-butoxycarbonyl)-1-(2-{[3-(isoquinolin-4-yl)-2-propynyl]oxy}ethyl)-1H-imidazo[4,5-c]quinolin-4-amine.

HRMS(EI) calcd for $C_{34}H_{35}N_5O_5$ (M$^+$) 594.2716, found 594.2732

Part G

Under a nitrogen atmosphere, the material from Part F was added in portions to a mixture of dichloromethane (5 mL) and trifluoroacetic acid (5 mL). The resulting solution was allowed to stir at ambient temperature for 2 hours at which time TLC indicated the reaction was complete. The solvents were removed under reduced pressure. The residue was diluted with dichloromethane/methanol (~4/1) and 20% sodium hydroxide. The layers were separated. The aqueous fraction was extracted with dichloromethane/methanol (~4/1). The organic fractions were combined, dried over magnesium sulfate, filtered and then concentrated under reduced pressure. The residue was purified by flash chromatography to provide 0.15 g of 1-(2-{[3-(isoquinolin-4-yl)-2-propynyl]oxy}ethyl)-1H-imidazo[4,5-c]quinolin-4-amine as an off-white solid, m.p. dec >205°.

$^1$H NMR (300 MHz, DMSO) δ 9.30 (s, 1 H), 8.43 (s, 1 H), 8.35 (s, 1 H), 8.19 (m, 2 H), 7.88 (br d, J=8.0 Hz, 1 H), 7.65–7.80 (m, 4 H), 7.60 (d, J=8.3 Hz, 1 H), 7.49 (t, J=7.8 Hz, 1 H), 7.34 (t, J=7.8 Hz, 1 H), 4.93 (t, J=4.9 Hz, 2 H), 4.57 (s, 2 H), 4.14 (t, J=5.1 Hz, 2 H)

HRMS(ESI) calcd for $C_{24}H_{19}N_5O$ (MH$^+$) 394.1668, found 394.1669

EXAMPLE 2

1-(2-{[3-(1,3-Thiazol-2-yl)-2-propynyl]oxy}ethyl)-1H-imidazo[4,5-c]quinolin-4-amine

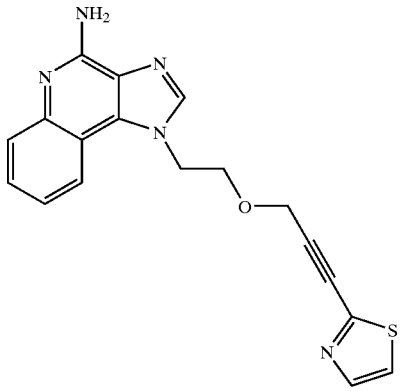

Part A

Using the general method of Example 1 Part F, N,N-(bis tert-butoxycarbonyl)-1-[2-(2-propynyloxy)ethyl]-1H-imidazo[4,5-c]quinolin-4-amine (1.0 g, 2.14 mmol) was reacted with 2-bromothiazole to provide 0.97 g of N,N-(1,is tert-butoxycarbonyl)-1-(2-{[3-(1,3-thiazol-2-yl)-2-propynyl]oxy}ethyl)-1H-imidazo[4,5-c]quinolin-4-amine as a glassy yellow solid.

MS(C) 550, 450, 350

Part B

Using the general method of Example 1 Part G, the material from Part B was hydrolyzed to provide 0.97 g of 1-(2-{[3-(1,3-thiazol-2-yl)-2-propynyl]oxy}ethyl)-1H-imidazo[4,5-c]quinolin-4-amine as a white solid, m.p. 157–159° C.

Analysis. Calculated for $C_{18}H_{15}N_5OS\cdot(H_2O)_{1/4}$: %C, 61.09; %H, 4.42; %N, 19.79. Found: %C, 61.06; %H, 4.37; %N, 19.53

$^1$H NMR (500 MHz, DMSO) δ 8.18 (s, 1 H), 8.11 (d, J=7.9 Hz, 1 H), 7.89 (dd, J=17.7, 2.9 Hz, 1 H), 7.62 (d, J=7.9 Hz, 1 H), 7.43 (t, J=7.5 Hz, 1 H), 7.23 (t, J=7.5 Hz, 1 H), 6.64 (s, 2 H), 4.83 (m, 2 H), 4.50 (s, 2 H), 4.01 (m, 2 H)

HRMS(EI) calcd for $C_{18}H_{15}N_5OS$ (M$^+$) 349.0997, found 349.0988

EXAMPLE 3

1-{2-[3-(1H-Pyrazol-4-yl)propoxy]ethyl}-1H-imidazo[4,5-c]quinolin-4-amine

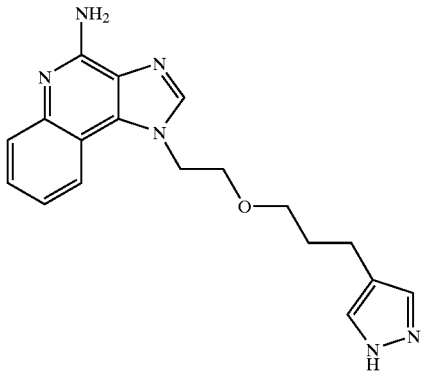

Part A

N,N-(bis tert-butoxycarbonyl)-1-[2-(2-propynyloxy)ethyl]-1H-imidazo[4,5-c]quinolin-4-amine (2.25 g, 4.82 mmol), triethylamine (1.34 mL, 9.64 mmol), 4-iodopyrazole (1.02 g, 5.30 mmol) and anhydrous acetonitrile (40 mL) were combined. Nitrogen was bubbled through the resulting solution for 10 minutes. Dicblorobis(triphenylphosphine)palladium(II) (68 mg, 0.096 mol) and copper(I) iodide (37 mg, 0.192 mmol) were added and the solution was heated to 40° C. After 1 hour analysis by HPLC (reverse phase) indicated that no reaction had taken place. The reaction solution was heated to about 90° C. After 4 hours analysis by HPLC indicated that the reaction was complete. The volatiles were removed under reduced pressure. The residue was purified by flash chromatography (9/1 dichloromethane/methanol) to provide 1.2 g of N,N-(bis tert-butoxycarbonyl)-1-(2-{[3-(1H-pyrazol-4-yl)-2-propynyl]oxy}ethyl)-1H-imidazo[4,5-c]quinolin-4-amine as a white solid.

Part B

The material from Part A was combined with methanol (~20 mL) and catalyst (0.25 g of 10% palladium on carbon). The mixture was hydrogenated for 4 hours at which time analysis by reverse phase LC-MS indicated reduction to the alkene and the alkane. More catalyst (0.25 g) was added and the mixture was hydrogenated for 2 days at which time LC-MS indicated one product with no starting material or alkene. The mixture was filtered and the filtrate was washed with methanol. The solution was concentrated to give a solid. This material was purified by flash chromatography (9/1 dichloromethane/methanol) to provide 0.9 g of N,N-(bis tert-butoxycarbonyl)-1-{2-[3-(1H-pyrazol-4-yl)propoxy]ethyl}-1H-imidazo[4,5-c]quinolin-4-amine as a white solid.

$^1$H NMR (300 MHz, DMSO) δ 12.43 (br s, 1 H), 8.48 (br d, J=7.1 Hz, 1 H), 8.37 (s, 1H), 8.08 (br d, J=7.3 Hz, 1 H), 7.72 (m, 2 H), 7.30 (br s, 1 H), 7.14 (br s, 1 H), 4.92 (t, J=4.9 Hz, 2 H), 3.88 (t, J=4.9 Hz, 2 H), 2.22 (t, J=7.8 Hz, 2 H), 1.56 (m, 2 H), 1.31 (s, 18 H)

MS (EI) 537, 437, 337

Part C

Under a nitrogen atmosphere trifluoroacetic acid was added to a mixture of N,N-(bis tert-butoxycarbonyl)-1-{2-[3-(1H-pyrazol-4-yl)propoxy]ethyl}-1H-imidazo[4,5-c]quinolin-4-amine (0.5 g, 0.93 mmol) and dichloromethane (5 mL). The resulting solution was allowed to stir for 16 hours at which time analysis by LC-MS indicated that the reaction was complete. The solvents were removed under reduced pressure. The residue was dissolved in ethyl acetate (~10 mL) and triethylamine (2 mL) was added. A precipitate formed and the reaction mixture was allowed to stir for 2 hours. The solid was isolated by filtration and then it was purified by flash chromatography (9/1 to 8/2 dichloromethane/methanol) to provide 0.18 g of 1-{2-[3-(1H-pyrazo-4-1-yl)propoxy]ethyl}-1H-imidazo[4,5-c]quinolin-4-amine as a white solid, m.p. 163–169° C.

Analysis. Calculated for $C_{18}H_2N_6O\cdot(CF_3CO_2H)_{0.15}$ %C, 62.18; %H, 5.75; %F, 2.42; %N, 23.77. Found: %C, 61.86; %H, 5.70; %F, 2.52; %N, 23.44

$^1$H NMR (300 MHz, DMSO) δ 12.50 (br s, 1 H), 8.20 (s, 1 H), 8.15 (d, J=8.3 Hz, 1 H), 7.66 (d, J=8.3 Hz, 1 H), 7.49 (t, J=7.6 Hz, 1 H), 7.29 (t, J=7.6 Hz, 1 H), 7.15–7.40 (br s, 2 H), 7.00 (br s, 2 H), 4.81 (t, J=4.6 Hz, 2 H), 3.84 (t, J=4.6 Hz, 2 H), 3.34 (t, J=6.1 Hz, 2 H), 2.27 (t, J=7.6 Hz, 2 H), 1.60 (m, 2 H)

EXAMPLE 4

1-[2-(3-Pyrimidin-2-ylpropoxy)ethyl]-1H-imidazo[4,5-c]quinolin-4-amine

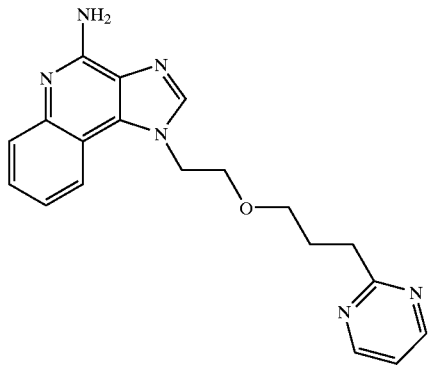

Part A

Under a nitrogen atmosphere dibenzyl dicarbonate (50 g, 174 mmol) was added to a mixture of 1-[2-(2-propynyloxy) ethyl]-1H-imidazo[4,5-c]quinolin-4-amine (16.4 g, 61.6 mmol) and anhydrous N,N-dimethylformamide (200 mL). The reaction mixture was allowed to stir at ambient temperature for 16 hours and the reaction mixture turned homogeneous. The reaction mixture was partitioned between ethyl acetate and water. The layers were separated. The aqueous layer was extracted with ethyl acetate. The organic fractions were combined, washed with water, washed with brine, dried over magnesium sulfate, filtered and then concentrated under reduced pressure to provide a semisolid. This material was triturated with diethyl ether to provide 27.4 g of N,N-(bis benzyloxycarbonyl)-1-[2-(2-propynyloxy)ethyl]-1H-imidazo[4,5-c]quinolin-4-amine as a white solid.

Part B

N,N-(Bis benzyloxycarbonyl)-1-[2-(2-propynyloxy) ethyl]-1H-imidazo[4,5-c]quinolin-4-amine (1.00 g, 1.87 mmol), anhydrous acetonitrile (10 mL), triethylamine (0.68 mL, 4.86 mmol), and 2-bromopyrimidine (0.327 g, 2.06 mmol) were combined. Under a nitrogen atmosphere copper (I) iodide (0.014 g) and dichlorobis(triphenylphosphine) palladium(II) (0.026 g) were added. The reaction mixture was maintained at ambient temperature for 15 minutes and then heated to 80° C. for 1.5 hours. The reaction mixture was diluted with ethyl acetate and water. The aqueous layer was separated and then extracted with ethyl acetate until no UV materials remained in the aqueous layer. The organic fractions were combined, washed with aqueous sodium bicarbonate and brine, dried over magnesium sulfate, filtered and then concentrated under reduced pressure. The residue was purified by column chromatography eluting with 98/2 ethyl acetate/methanol to provide 0.68 g of a mixture of the mono and di benzyloxycarbonyl protected 1-{2-[(3-pyrimidin-2-ylprop-2-ynyl)oxy]ethyl}-1H-imidazo[4,5-c]quinolin-4-amine.

$^1$H NMR (300 MHz, DMSO-d6) δ 8.78 (d, J=4.9 Hz, 2 H), 8.49 (m, 1 H), 8.45 (s, 1 H), 8.12 (m, 1 H), 7.73–7.78 (m, 2 H), 7.50 (t, J=4.9 Hz, 1 H), 7.23–7.28 (m, 6 H), 7.14–7.17 (m, 4 H), 5.20 (s, 4 H), 5.02 (t, J=5.0 Hz, 2 H), 4.51 (s, 2 H), 4.10 (t, J=5.0 Hz, 2 H),

MS (CI) for $C_{35}H_{28}N_5O_5$ m/z 613 (MH$^+$), 569, 461, 345

Part C

The material from Part B, palladium hydroxide (0.25 g of 20% on carbon) and methanol (25 mL) were combined and hydrogenated at 47 psi (3.3 Kg/cm$^2$) for 3 hours at ambient temperature. The reaction mixture was allowed to stand over the weekend at which time analysis indicated the presence of some product with protected amine groups. The reaction mixture was filtered to remove the catalyst and the filtrate was treated with sodium methoxide (1 mL of 25% in methanol) for about 16 hours to remove the protecting groups. The reaction mixture was concentrated under reduced pressure. The residue was purified by column chromatography eluting with 1/1/1 ethyl acetate/methanol/hexane to provide 0.235 g of a solid. This material was stirred with hot toluene and then filtered to remove insoluble materials. The filtrate was concentrated under reduced pressure. The residue was triturated with isopropanol and ethyl acetate to provide 61 mg of 1-[2-(3-pyrimidin-2-ylpropoxy) ethyl]-1H-imidazo[4,5-c]quinolin-4-amine as a solid, m.p. 126–127° C.

Analysis. Calculated for $C_{19}H_{20}N_6O$: %C, 65.5; %H, 5.79; %N, 24.12. Found: %C, 65.65; %H, 5.78; %N, 24.15

$^1$H NMR (300 MHz, DMSO-d6) δ 8.66 (d, J=4.7 Hz, 2 H), 8.14 (s, 1 H), 8.08 (d, J=8.0 Hz, 1 H), 7.62 (d, J=8.2 Hz, 1 H), 7.45 (t, J=7.0 Hz, 1 H), 7.24–7.31 (m, 2 H) 6.58 (s, 2 H), 4.77 (t, J=4.7 Hz, 2 H), 3.84 (t, J=4.5 Hz, 2 H), 3.42 (t, J=6.2 Hz, 2 H), 2.82 (t, J=7.5 Hz, 2 H), 1.89 (m, 2H)

IR (KBr) 3302, 3187, 2868, 1637, 1561, 1418, 1139 cm$^{-1}$

HRMS (EI) calcd for $C_{19}H_{20}N_6O$ (M$^+$) 348.1699, found 348.1700.

EXAMPLE 5

1-[2-(3-Pyridin-4-ylpropoxy)ethyl]-1H-imidazo[4,5-c]quinolin-4-amine

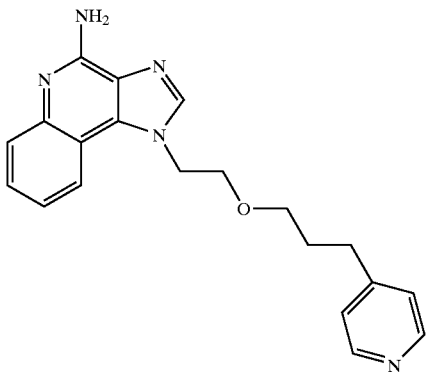

Part A

Using the general method of Example 4 Part B N,N-(bis benzyloxycarbonyl)-1-[2-(2-propynyloxy)ethyl]-1H- imidazo[4,5-c]quinolin-4-amine (2.00 g, 3.74 mmol) was reacted with 4-bromopyridine (0.8 g, 4.12 mmol) to provide 1.47 g of a mixture of mono and di benzyloxycarbonyl protected 1-{2-[(3-pyridin-4-ylprop-2-ynyl)oxy]ethyl}-1H-imidazo[4,5-c]quinolin-4-amine.

$^1$H NMR (300 MHz, DMSO-d6) δ 8.46 (m, 3 H), 8.43 (s, 1 H), 8.12 (m, 1 H), 7.72–7.76 (m, 2 H), 722–7.28 (m, 5 H), 7.14–7.17 (m, 6 H), 5.18 (s, 4 H), 5.00 (t, J=5.0 Hz, 2 H), 4.45 (s, 2 H), 4.12 (t, J=4.0 Hz, 2 H)

MS (CI) for $C_{36}H_{29}N_5O_5$ m/z 612 (MH$^+$), 568, 344

Part B

Palladium hydroxide (0.57 g of 20% on carbon) was added to a solution of the material from Part A in methanol (~10 mL). The mixture was hydrogenated at 50 psi (3.5 Kg/cm$^2$) for 5 hours. More catalyst (0.07 g) was added and the hydrogenation was continued for another hour. The reaction mixture was filtered to remove catalyst and the filter cake was thoroughly washed with methanol. The filtrate was concentrated under reduced pressure. The residue was purified by column chromatography eluting with 6/3/1 ethyl acetate/methanol/hexane and then triturated with diethyl ether to provide a solid. This material was further purified by column chromatography eluting with 9/1 dichloromethane/methanol with ammonium hydroxide to provide 0.20 g of 1-[2-(3-pyridin-4-ylpropoxy)ethyl]-1H-imidazo[4,5-c]quinolin-4-amine as a solid, m.p. 160–162° C.

Analysis. Calculated for $C_{20}H_{21}N_5O$: %C, 69.14; %H, 6.09; %N, 20.16. Found: %C, 69.17; %H, 6.09; %N, 19.79

$^1$H NMR (300 MHz, DMSO-d6) δ 8.29 (dd, J=2.6, 1.8 Hz, 2 H), 8.18 (s, 1 H), 8.11 (d, J=8.2 Hz, 1 H), 7.62 (dd, J=7.1, 1.4 Hz, 1 H), 7.45 (dt, J=6.9, 1.7 Hz, 1 H), 7.23 (dt, J=6.7, 1.3 Hz, 1 H), 6.91 (dd, J=4.4, 1.3 Hz, 2 H), 6.62 (s, 2 H), 4.81 (t, J=5.0 Hz, 2 H), 3.82 (t, J=5.0 Hz, 2 H), 2.38 (t, J=7.6 Hz, 2 H), 3.28 (t, J=6.1 Hz, 2 H), 1.64 (m, 2 H)

IR (KBr) 3418, 3100, 1698, 1595, 1531, 1094, 767 cm$^{-1}$

HRMS (EI) calcd for $C_{20}H_{21}N_5O$ (M$^+$) 347.1746, found 347.1747

EXAMPLE 6

1-[2-(3-Pyridin-2-ylpropoxy)ethyl]-1H-imidazo[4,5-c]quinolin-4-amine

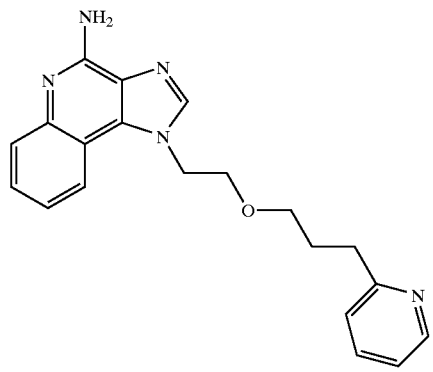

Part A

Under a nitrogen atmosphere N,N-(bisbenzyloxycarbonyl)-1-[2-(2-propynyloxy)ethyl]-1H-imidazo[4,5-c]quinolin-4-amine (2.5 g, 4.68 mmol), anhydrous acetonitrile (20 mL), triethylamine (1.7 mL, 12.2 mmol), and 2-bromopyridine (0.5 mL, 5.14 mmol) were combined and the resulting homogeneous mixture was heated to 40° C. Copper (I) iodide (0.036 g) and dichlorobis(triphenylphosphine)palladium(II) (0.066 g) were added. After 18.5 hours the reaction mixture was partitioned between ethyl acetate and aqueous sodium bicarbonate. The organic fraction was washed with brine, dried over magnesium sulfate and then concentrated under reduced pressure. The residue was purified by column chromatography eluting with 1/9 hexane/ethyl acetate to provide 0.9 g of a mixture of mono and di benzyloxycarbonyl protected 1-{2-[(3-pyridin-2-ylprop-2-ynyl)oxy]ethyl}-1H-imidazo[4,5-c]quinolin-4-amine.

$^1$H NMR (300 MHz, DMSO-d6) δ 8.50–8.54 (m, 2 H), 8.44 (s, 1H), 8.12 (m, 1 H), 7.71–7.77 (m, 3 H), 7.34–7.39 (m, 1 H), 7.23–7.29 (m, 7 H), 7.14–7.17 (m, 4 H), 5.19 (s, 4 H), 5.01 (t, J=4.6 Hz, 2 H), 4.46 (s, 2 H), 4.10 (t, J=4.8 Hz, 2 H)

MS (CI) for $C_{36}H_{29}N_5O_5$ m/z 612 (MH$^+$), 568, 460

Part B

Palladium hydroxide (0.776 g of 20% on carbon) was added to a solution of the material from Part A in methanol. The mixture was hydrogenated at 45 psi (3.2 Kg/cm$^2$) for 2.5 hours. The reaction mixture was filtered to remove catalyst and the filter cake was thoroughly washed with methanol. The filtrate was concentrated under reduced pressure to provide a glassy solid. This material was triturated with diethyl ether and hexane containing a small amount of toluene. The resulting powder was isolated by filtration and dried at 78° C. overnight in a vacuum oven. This material was further purified by column chromatography eluting with 9/1 dichloromethane/methanol with a few drops of ammonium hydroxide to provide 25 mg of 1-[2-(3-pyridin-2-ylpropoxy)ethyl]-1H-imidazo[4,5-c]quinolin-4-amine as a solid, m.p. 138–140° C.

Analysis. Calculated for $C_{20}H_{21}N_5O \cdot (H_2O)_{1/5}$: %C, 68.43; %H, 6.15; %N, 19.95. Found: %C, 68.47; %H, 5.95; %N, 19.63

$^1$H NMR (300 MHz, DMSO-d6) δ 8.41 (d, J=4.4 Hz, 1 H), 8.16 (s, 1 H), 8.10 (d, J=7.7 Hz, 1 H), 7.63 (d, J=8.4 Hz, 1 H), 7.54 (dt, J=9.7, 1.7 Hz, 1 H), 7.43 (t, J=7.3 Hz, 1 H), 7.24 (t, J=7.5 Hz, 1 H), 7.13 (t, J=5.5 Hz, 1 H), 6.93 (d, J=7.6 Hz, 1 H), 6.59 (s, 2 H), 4.77 (t, J=5.1 Hz, 2 H), 3.82 (t, J=5.5 Hz, 2 H), 3.34 (t, J=6.3 Hz, 2 H), 2.57 (t, J=7.3 Hz, 2 H), 1.75 (m, 2 H)

IR (KBr) 3361, 3302, 3188, 1638, 1526, 1119, 751 cm$^{-1}$

HRMS (EI) calcd for $C_{20}H_{21}N_5O$ (M$^+$) 347.1746, found 347.1747.

EXAMPLE 7

1-{2-[3-(1,3-Thiazol-2-yl)propoxy]ethyl}-1H-imidazo[4,5-c]quinolin-4-amine

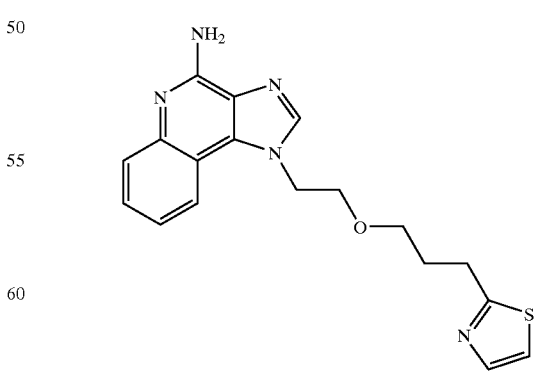

Part A

Under a nitrogen atmosphere N,N-(Bisbenzyloxycarbonyl)-1-[2-(2-propynyloxy)ethyl]-1H- imidazo[4,5-c]quinolin-4-amine (3.25 g, 6.08 mmol), anhydrous N,N-dimethylformamide (15 mL), triethylamine (2.2 mL, 15.8 mmol) and 2-bromothiazole (0.6 mL, 6.69 mmol) were combined and heated to 80° C. Copper (I) iodide (0.046 g) and dichlorobis(triphenylphosphine)palladium (II) (0.085 g) were added. After 2 hours the reaction was stopped and the solvent was removed. The crude product was purified by column chromatography eluting with 8/2 ethyl acetate/hexane to provide ~2 g of a mixture of mono and di benzyloxycarbonyl protected 1-(2-{[3-(1,3-thiazol-2-yl)prop-2-ynyl]oxy}ethyl)-1H-imidazo[4,5-c]quinolin-4-amine.

$^1$H NMR (300 MHz, DMSO-d6) δ 8.47–8.50 (m, 1 H), 8.44 (s, 1 H), 8.11 (m, 1 H), 7.89 (d, J=3.2 Hz, 1 H), 7.85 (d, J=3.3 Hz, 1 H), 7.31–7.77 (m, 2 H), 7.23–7.28 (m, 6 H), 7.14–7.17 (m, 4 H), 5.20 (s, 4 H), 5.00 (t, J=5.0 Hz, 2 H), 4.52 (s, 2 H), 4.09 (t, J=5.5 Hz, 2 H)

MS (CI) for $C_{24}H_{27}N_5O_5S$ m/z 618 (MH$^+$), 475, 466

Part B

Palladium hydroxide (~2 g of 20% on carbon) was added to a solution of the material from Part A in methanol. The mixture was hydrogenated at 45 psi (3.2 Kg/cm$^2$) for 3 hours. More catalyst (0.3 g) was added twice and the hydrogenation was continued for a total of ~25 hours. The reaction mixture was filtered to remove the catalyst. The filtrate was concentrated under reduced pressure to provide 1.3 g of mono benzyloxycarbonyl protected 1-{2-[3-(1,3-thiazol-2-yl)propoxy]ethyl}-1H-imidazo[4,5-c]quinolin-4-amine. This material was combined with methanol (5 mL) and sodium methoxide (25 mL of 25% in methanol). The resulting mixture was stirred for 3 days. The reaction mixture was concentrated under reduced pressure and then purified by column chromatography. The resulting material was triturated with diethyl ether and dried to provide 0.28 g of 1-{2-[3-(1,3-thiazol-2-yl)propoxy]ethyl}-1H-imidazo[4,5-c]quinolin-4-amine as a solid, m.p. 134–135° C.

Analysis. Calculated for $C_{18}H_{19}N_5OS$: %C, 61.17; %H, 5.42; %N, 19.81. Found: %C, 61.20; %H, 5.23; N, %19.51

$^1$H NMR (300 MHz, DMSO-d6) δ 8.16 (s, 1 H), 8.10 (d, J=8.4 Hz, 1 H), 7.63 (m, 2 H), 7.51 (d, J=3.3 Hz, 1 H), 7.43 (t, J=7.1 Hz, 1 H), 7.23 (t, J=8.0 Hz, 1 H), 6.58 (s, 2 H), 4.79 (t, J=4.7 Hz, 2 H), 3.84 (t, J=4.8 Hz, 2 H), 3.4 (t, J=6.0 Hz, 2 H), 2.86 (t, J=7.8 Hz, 2 H), 1.83 (m, 2 H)

IR(KBr) 3458, 3358, 3295, 3191, 1640, 1538, 1121, 752 cm$^{-1}$

HRMS (EI) calcd for $C_{18}H_{19}N_5OS$ (M$^+$) 353.1310, found 353.1308.

EXAMPLE 8

1-[2-(3-Pyridin-3-ylpropoxy)ethyl]-1H-imidazo[4,5-c]quinolin-4-amine Bis(trifluoroacetate)

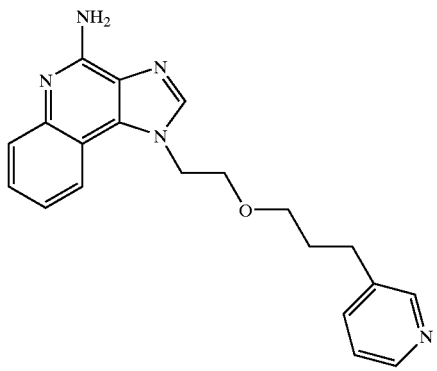

Part A

Under a nitrogen atmosphere N,N-(bis tert-butyoxycabonyl)-1-[2-(2-propynyloxy)ethyl]-1H-imidazo[4,5-c]quinolin-4-amine (1.75 g, 3.75 mmol), 3-iodopyridine (0.85 g, 4.13 mmol), triethylamine (1.4 mL) and acetonitrile (15 mL) were combined and then heated to 60° C. Copper (I) iodide (0.03 g, 0.15 mmol) and dichlorobis (triphenylphosphine)palladium (II) (0.05 g, 0.075 mmol) were added. The reaction was complete after 30 minutes. The solvents were removed under reduced pressure. The crude product was purified by column chromatography (silica gel eluting first with dichloromethane and then with 98/2 dichloromethane/methanol) to provide 1.26 g of a mixture of di-BOC protected and unprotected 1-{2-[(3-pyridin-3-ylprop-2-ynyl)oxy]ethyl}-1H-imidazo[4,5-c]quinolin-4-amine.

$^1$H NMR (300 MHz, DMSO-d6) δ 8.54 (bs, 1 H), 8.44–8.48 (m, 2 H), 8.4 (s, 1 H), 8.06 (m, 1 H), 7.69–7.73 (m, 2 H), 7.54 (d, J=7.6 Hz, 1 H), 7.35 (m, 1 H), 4.99 (t, J=4.8 Hz, 2 H), 4.40 (s, 2 H), 4.09 (t, J=5.0 Hz, 2 H), 1.31 (s, 18 H),

MS (CI) for $C_{30}H_{33}N_5O_5$ m/z 544 (MH$^+$), 444, 344

Part B

A solution of the material from Part A in methanol was combined with catalyst (0.7 g of 10% palladium on carbon) and the mixture was hydrogenated at 45 psi (3.2 Kg/cm$^2$) for 2 hours. The catalyst was removed by filtration and the filtrate was concentrated under reduced pressure to provide 0.67 g of a mixture of di-BOC protected and unprotected 1-[2-(3-pyridin-3-ylpropoxy)ethyl]-1H-imidazo[4,5-c]quinolin-4-amine.

$^1$H NMR (300 MHz, DMSO-d6) δ 8.50 (d, J=7.3 Hz, 1 H), 8.39–8.486 (m, 2 H), 8.29 (s, 1 H), 8.07 (d, J=8.4 Hz, 1 H), 7.71–7.75 (m, 2 H), 7.46 (d,J=8.5 Hz, 1 H), 7.31 (m, 1 H), 4.94 (t, J=4.6 Hz, 2 H), 3.88 (t, J=5.0 Hz, 2 H), 3.32 (t, J=5.9 Hz, 2 H), 2.38 (t, J=7.5 Hz, 2 H), 1.63 (m, 2 H), 1.30 (s, 18 H),

MS (CI) for $C_{30}H_{37}N_5O_5$ m/z 548 (MH$^+$), 448, 348

Part C

Under a nitrogen atmosphere the material from Part B was combined with anhydrous dichloromethane (5 mL) and trifluoroacetic acid (5 mL). The reaction mixture was stirred at ambient temperature for 1 hr. The solvents were removed under reduced pressure. The residue was triturated with diethyl ether, isolated by filtration and then dried in a vacuum oven to provide a tan solid. This material was recrystallized first from isopropyl alcohol and then from dichloromethane/methanol to provide 0.40 g of 1-[2-(3-pyridin-3-ylpropoxy)ethyl]-1H-imidazo[4,5-c]quinolin-4-amine bis(trifluoroacetate), m.p. 134–136° C.

Analysis. Calculated for $C_{20}H_{21}N_5O.(C_2HF_3O_2)_2.(H_2O)_{1/2}$: %C, 50.08; %H, 4.23; %N, 12.03. Found: %C, 49.87; %H, 3.82; %N, 12.16

$^1$H NMR (300 MHz, DMSO-d6) δ 9.00–9.25 (bs, 2 H), 8.50 (s, 2 H), 8.37 (d, J=7.7 Hz, 1 H), 7.82 (d, J=7.4 Hz, 1 H), 7.73–7.75 (m, 2 H), 7.55–7.58 (m, 2 H), 4.90 (t, J=4.9 Hz, 2 H), 3.86 (t, J=4.8 Hz, 2 H), 3.35 (t, J=6.1 Hz, 2 H), 2.49 (t, J=7.0 Hz, 2 H), 1.67 (m, 2 H)

IR (KBr) 3421, 3212, 2885, 1699, 1199, 1120, 720 cm$^{-1}$

HRMS (EI) calcd for $C_{20}H_{21}N_5O$ (M$^+$) 347.1746, found 347.1743.

EXAMPLE 9

1-[2-(3-Pyrimidin-5-ylpropoxy)ethyl]-1H-imidazo[4,5-c]quinolin-4-amine

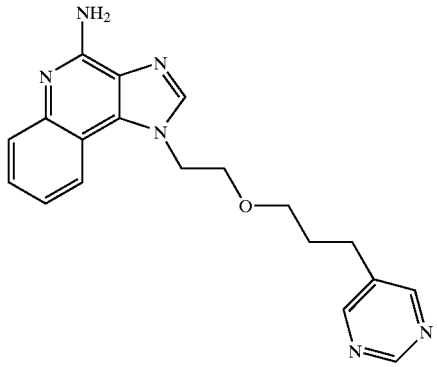

Part A

Using the general method of Example 8 Part A, except that the reaction temperature was raised to 80° C., N,N-(bis tert-butyoxycabonyl)-1-[-(2-propynyloxy)ethyl]-1H-imidazo[4,5-c]quinolin-4-amine (2.5 g, 5.36 mmol) was coupled with 5-bromopyrimidine (0.94 g, 5.89 mmol) to provide 1.59 g of N,N-(bis tert-butoxycarbonyl)-1-{2-[(3-pyrimidin-5-ylprop-2-ynyl)oxy]ethyl}-1H-imidazo[4,5-c]quinolin-4-amine.

$^1$H NMR (300 MHz, DMSO-d6) δ 9.19 (s, 1 H), 8.64 (s, 2 H), 8.44–8.47 (m, 1 H), 8.40 (s, 1 H), 8.02–8.06 (m, 1 H), 7.68–7.72 (m, 2 H), 4.99 (t, J=5.0 Hz, 2 H), 4.43 (s, 2 H), 4.10 (t, J=5.2 Hz, 2 H), 1.32 (s, 18 H)

MS (CI) for $C_{29}H_{32}N_6O_5$ m/z 545 (MH$^+$), 445, 345

Part B

A methanol solution of the material from Part A was combined with catalyst (5% platinum on carbon, palladium hydroxide and 10% palladium on carbon were used in succession) and hydrogenated to provide 0.60 g of N,N-(bis tert-butoxycarbonyl)-1-[2-(3-pyrimidin-5-ylpropoxy)ethyl]-1H-imidazo[4,5-c]quinolin-4-amine.

$^1$H NMR (300 MHz, DMSO-d6) δ 8.98 (s, 1 H), 8.48–8.52 (m, 1 H), 8.45 (s, 2 H), 8.40 (s, 1 H), 8.06–8.09 (m, 1 H), 7.70–7.74 (m, 2 H), 4.94 (t, J=5.1 Hz, 2 H), 3.89 (t, J=5.0 Hz, 2 H), 3.34 (m, 2 H), 2.34 (t, J=7.3 Hz, 2 H), 1.64 (m, 2 H), 1.29 (s, 18 H)

MS (CI) for $C_{29}H_{36}N_6O_5$ m/z 549 (MH$^+$), 449, 349

Part C

Using the general method of Example 8 Part C, the material from Part B was hydrolyzed to provide 0.14 g of 1-[2-(3-pyrimidin-5-ylpropoxy)ethyl]-1H-imidazo[4,5-c]quinolin-4-amine, m.p. 159–161° C.

Analysis. Calculated for $C_{19}H_{20}N_6O·(C_2HF_3O_2)_{1/10}·(H_2O)_{1/4}$: %C, 63.27; %H, 5.70; %N, 23.06. Found: %C, 63.47; %H, 5.35; %N, 22.88

$^1$H NMR (300 MHz, DMSO-d6) δ 8.98 (s, 1 H), 8.48 (s, 2 H), 8.19 (s, 1 H), 8.15 (d, J=8.0 Hz, 1 H), 7.63 (d, J=8.6 Hz, 1 H), 7.46 (t, J=6.0 Hz, 1 H), 7.28 (t, J=8.4 Hz, 1 H), 6.79 (s, 2 H), 4.81 (t, J=4.8 Hz, 2 H), 3.84 (t, J=5.1 Hz, 2 H), 3.35 (t, J=6.0 Hz, 2 H), 2.43 (t, J=7.4 Hz, 2 H), 1.69 (m, 2 H)

IR (KBr) 3310, 3132, 1647, 1582, 1531, 1403, 1117 cm$^{-1}$

HRMS (EI) calcd for $C_{19}H_{20}N_6O$ (M$^+$) 348.1699, found 348.1695

EXAMPLE 10

1-{2-[(1-Benzyl-1H-1,2,3-triazol-4-yl)methoxy]ethyl}-1H-imidazo[4,5-c]quinoline-4-amine hydrochloride

1-{2-[(1-Benzyl-1H-1,2,3-triazol-5-yl)methoxy]ethyl}-1H-imidazo[4,5-c]quinoline-4-amine hydrochloride

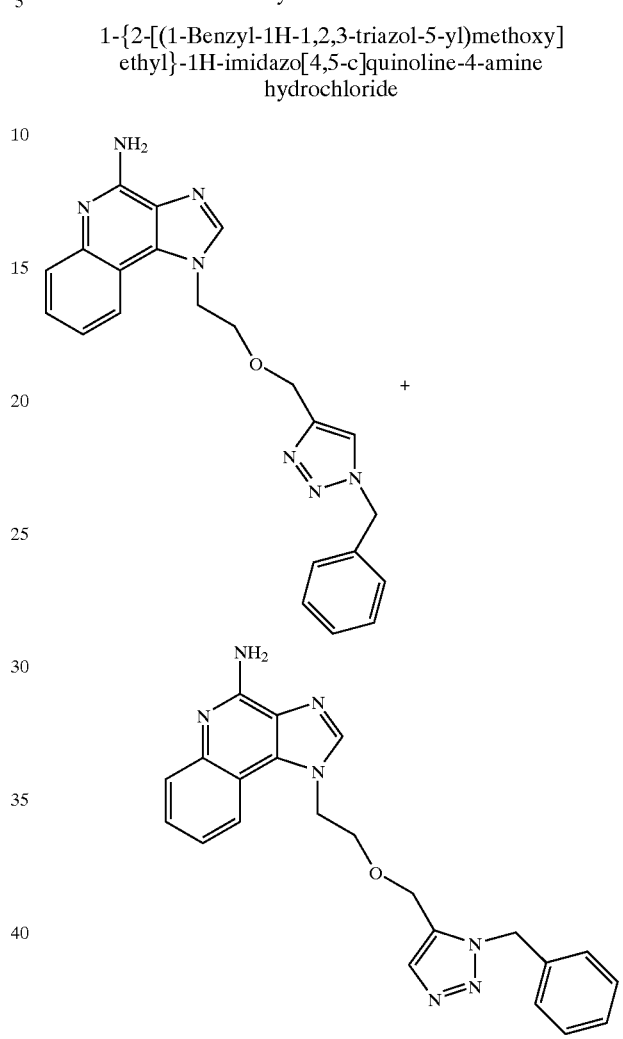

Part A

N,N-(Bis benzyloxycarbonyl)-1-[2-(2-propynyloxy)ethyl]-1H-imidazo[4,5-c]quinolin-4-amine (1.5 g, 2.81 mmol), anhydrous toluene (30 mL) and benzyl azide (1.3 mL, 9.12 mmol) were combined and heated in an oil bath at 100° C. for 28 hours. The reaction mixture was concentrated under reduced pressure to provide crude product as a brown oil.

Part B

Sodium methoxide (2.19 mL of 25% in methanol, 9.52 mmol) was added to a mixture of the material from Part A and methanol (20 mL). The reaction mixture was allowed to stir at ambient temperature overnight and then it was concentrated under reduced pressure to provide a dark oil. The oil was purified by column chromatography eluting with 5% methanol in dichloromethane to provide a light yellow oil. The oil was treated with 1.0 M hydrogen chloride to provide a pink solid. This solid was recrystallized twice from acetonitrile and the resulting product was dried in a vacuum oven at 80° C. for 2 hours to provide 0.12 g of a mixture of the regio isomers of the desired product i.e. a mixture containing both 1-{2-[(1-benzyl-1H-1,2,3-triazol-4-yl)methoxy]ethyl}-

1H-imidazo[4,5-c]quinoline-4-amine hydrochloride and 1-{2-[(1-benzyl-1H-1,2,3-triazol-5-yl)methoxy]ethyl}-1H-imidazo[4,5-c]quinoline-4-amine hydrochloride, as a light pink crystalline solid, m.p. 209–211° C.

Analysis: Calculated for $C_{22}H_{21}N_7O \cdot 0.951$ HCl $\cdot 0.615$ $H_2O$: %C, 59.35; %H, 5.25; %N, 22.02; Found: %C, 59.46; %H, 5.16; %N, 22.05.

$^1$H-NMR (300 MHz, DMSO-d6) δ 9.00 (br s, 2 H), 8.46 (s, 1 H), 8.28 (d, J=7.8 Hz, 1 H), 7.98 (s, 1 H), 7.83 (br d, J=7.8 Hz, 1 H), 7.71 (br t, J=7.8 Hz, 1 H), 7.50 (br t, J=7.7 Hz, 1 H) 7.20–7.40 (m, 5 H), 5.52 (s, 1.88 H), 5.39 (s, 0.12 H), 4.88 (t, J=4.9 Hz, 2 H), 4.52 (s, 2 H), 3.95 (t, J=4.9 Hz, 1.88 H), 3.87 (t, J=5.1 Hz, 0.12 H)

IR (KBr) 3152, 2638, 1672, 1605, 1126 cm$^{-1}$

HRMS (EI) calcd for $C_{22}H_{21}N_7O$ (M$^+$) 399.1808, found 399.1802.

EXAMPLE 11

1-[2-({1-[(Phenylsulfanyl)methyl]-1H-1,2,3-triazol-4-yl}methoxy)ethyl]-1H-imidazo[4,5-c]quinoline-4-amine 1-[2-({1-[(Phenylsulfanyl)methyl]-1H-1,2,3-triazol-5-yl}methoxy)ethyl]-1H-imidazo[4,5-c]quinoline-4-amine

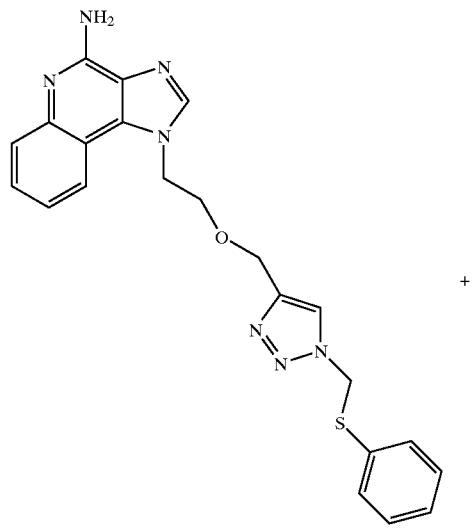

+

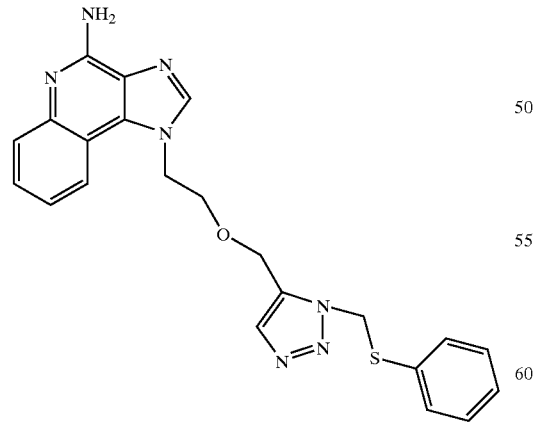

Part A

Under a nitrogen atmosphere, anhydrous toluene (20 mL), N,N-(bis tert-butoxycarbonyl)-1-[2-(2-propynyloxy)ethyl]-1H-imidazo[4,5-c]quinolin-4-amine (1.0 g, 2.1 mmol) and azidomethyl phenylsulfide (0.61 mL, 4.3 mmol) were combined and heated at reflux for 72 hours. The reaction mixture was allowed to cool to ambient temperature and then it was concentrated under reduced pressure to provide a brown oil. This material was purified by column chromatography eluting with 80/20 ethyl acetate/hexane to provide 0.95 g of product as a clear oil.

MS (CI) for $C_{32}H_{37}N_7O_5S$ m/z 632 (MH+), 532, 458, 432

Part B

A solution of the material from Part A in anhydrous dichloromethane (15 mL) was added to a mixture of trifluoroacetic acid (7.4 mL) and anhydrous dichloromethane (6 mL) which had been chilled to 0° C. The reaction mixture was kept in an ice bath for 2 hours and then allowed to warm to ambient temperature. After 6 hours the reaction mixture was washed with 20% sodium hydroxide. The aqueous fraction was extracted with dichloromethane. The organic fractions were combined, washed with water, dried over magnesium sulfate, filtered and then concentrated under reduced pressure to provide a green oil. The oil was purified by column chromatography eluting with 5% methanol in dichloromethane to provide a green crystalline solid. This material was recrystallized from isopropanol to provide 0.12 g of a mixture of the regio isomers of the desired product i.e. a mixture containing both 1-[2-({1-[(phenylsulfanyl)methyl]-1H-1,2,3-triazol-4-yl}methoxy)ethyl]-1H-imidazo[4,5-c]quinoline-4-amine and 1-[2-({1-[(phenylsulfanyl)methyl]-1H-1,2,3-triazol-5-yl}methoxy)ethyl]-1H-imidazo[4,5-c]quinoline-4-amine, as an off-white solid, m.p. 182–184° C.

Analysis: Calculated for $C_{22}H_{21}N_7OS$: %C, 61.24; %H, 4.91; %N, 22.72; Found: %C, 60.94; %H, 4.94; %N, 22.38.

$^1$H-NMR (300 MHz, DMSO-d6) δ 8.00–8.20 (m, 2 H), 7.87 (s, 0.8 H), 7.60–7.65 (m, 1 H), 7.52 (s, 0.2 H), 7.40–7.50 (m, 1 H), 7.20–7.40 (m, 6 H), 6.65 (s, 2 H), 5.87 (s, 1.6 H), 5.65 (s, 0.4 H), 4.83 (br t, J=4.6 Hz, 0.4 H), 4.78 (br t, J=4.9 Hz, 1.6 H), 4.49 (s, 1.6 H), 4.49 (s, 1.6 H), 4.42 (s, 0.4 H), 3.80–3.90 (m, 2H)

IR (KBr) 3322, 3205, 1643, 1527, 1095 cm$^{-1}$

HRMS (EI) calcd for $C_{22}H_{21}N_7OS$ (M$^+$) 431.1528, found 431.1522.

EXAMPLE 12

1-[2-(Benzo[b]furan-2-ylmethoxy)ethyl]-1H-imidazo[4,5-c]quinolin-4-amine

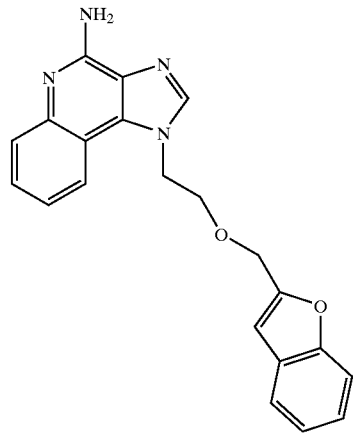

Part A

Benzyltrimethylammonium chloride (0.436 g) and propargyl bromide (6.07 mL of 80%) were added with stirring to a mixture of dichloromethane (185 mL) and aqueous sodium hydroxide (60 mL of 50%). 2-(1H-Imidazo[4,5-c]quinolin-1-yl)ethanol (10.0 g, 46.9 mmol) was added to the resulting solution. The reaction mixture was stirred at ambient temperature for 21 hours at which time analysis by HPLC showed that starting material remained. An additional equivalent of propargyl bromide was added and the reaction mixture was stirred for an additional 46 hours. Water was added to the reaction mixture and the layers were separated. The aqueous fraction was extracted with dichloromethane. The organic fractions were combined, washed with water and with brine, dried over magnesium sulfate and then concentrated under reduced pressure to provide a dark brown solid. This material was purified by flash chromatography (silica gel eluting with 5% methanol in dichloromethane) to provide 7.0 g of 1-[2-propynyloxy) ethyl]-1H-imidazo[4,5-c]quinoline as a brownish solid.

Part B

Under a nitrogen atmosphere, 1-[2-(propynyloxy)ethyl]-1H-imidazo[4,5-c]quinoline (1.0 g, 4.21 mmol), triethylamine (1.53 mL, 10.96 mmol) and anhydrous acetonitrile (20 mL) were combined and then heated to 60° C. 2-Iodophenol (1.02 g, 4.63 mmol), copper (I) iodide (0.08 g) and dichlorobis(triphenylphosphine)palladium(II) (0.148 g) were added. After 4 hours analysis by TLC (5% methanol in dichloromethane) indicated that the reaction was complete. The reaction mixture was filtered through a layer of Celite® filter aid to remove the catalysts. The filtrate was concentrated under reduced pressure to provide an oil. This material was purified by flash chromatography (silica gel eluting with 3% methanol in dichloromethane) to provide 0.91 g of 1-[2-(benzo[b]furan-2-ylmethoxy)ethyl]-1H-imidazo[4,5-c]quinoline as a yellow oil.

Part C

3-Chloroperoxybenzoic acid (0.65 g) was added in portions over a period of 5 minutes to a solution of the material from Part B in chloroform (15 mL). The progress of the reaction was monitored by TLC. More 3-chloroperoxybenzoic acid (2×0.2 g) was added. After 1.5 hr the reaction mixture was washed twice with aqueous sodium bicarbonate, back extracted with chloroform, washed with brine and then concentrated under reduced pressure to provide 1-[2-(benzo[b]furan-2-ylmethoxy) ethyl]-1H-imidazo[4,5-c]quinoline-5N-oxide. The material was stored under nitrogen at a reduced temperature over the weekend.

Part D

Under a nitrogen atmosphere, trichloroacetyl isocyanate (0.60 g, 3.18 mmol) was slowly added via a syringe to a solution of the N-oxide from Part C in dichloromethane (15 mL). The volatiles were removed under reduced pressure to provide 2,2,2-trichloro-{1-[2-(benzo[b]furan-2-ylmethoxy) ethyl]-1H-imidazo[4,5-c]quinolin-4-yl}acetamide as a tan solid. This material was dissolved in methanol (15 mL). Sodium methoxide (2.04 mL, 9.01 mmol) was added and the resulting solution was allowed to stir for 48 hours. A white precipitate was isolated by filtration and then recrystallized from acetonitrile to provide 0.22 g of 1-[2-(benzo[b]furan-2-ylmethoxy)ethyl]-1H-imidazo[4,5-c]quinolin-4-amine as off-white needles, m.p. 201–203° C.

Analysis: Calculated for $C_{21}H_{18}N_4O_2$: %C, 70.38; %H, 5.06; %N, 15.63; Found: %C, 70.36; %H, 4.80; %N 15.51.

$^1$H-NMR (300 MHz, DMSO-d6) δ 8.18 (s, 1H), 8.06 (d, J=7.8 Hz, 1H), 7.49–7.62 (m, 3H), 7.42 (m, 1H), 7.16–7.31 (m, 3H), 6.76 (s, 1H), 6.58 (br s, 2H), 4.83 (t, J=5.4 Hz, 2H), 4.61 (s, 2H), 3.97 (t, J=5.1 Hz, 2H)

IR (KBr) 3455, 3069, 1583, 1530, 1397, 1254, 1088

HRMS (EI) calcd for $C_{21}H_{18}N_4O_2$ (M$^+$) 358.1430, found 358.1428.

EXAMPLE 13

1-[2-(Pyridin-3-ylmethoxy)ethyl]-1H-imidazo[4,5-c] quinolin-4-amine Hydrochloride

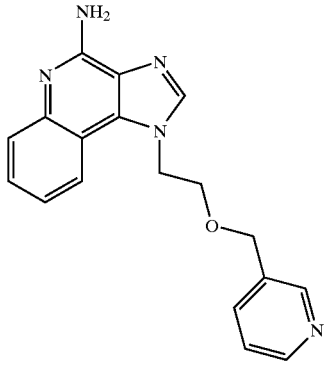

Part A

Under a nitrogen atmosphere, sodium hydride (16.88 g of 60% in mineral oil, 422 mmol) was added in portions to a solution of 2-(1H-imidazo[4,5-c]quinolin-1-yl)ethanol (60.0 g, 281 mmol) in anhydrous N,N-dimethylformamide (600 mL). The alkoxide was allowed to stir for about 1.5 hours. Benzyl bromide (50.2 mL, 422 mmol) was slowly added over a period of about 30 minutes. The reaction mixture was allowed to stir at ambient temperature overnight. Solvent was removed under reduced pressure. The residue was taken up in ethyl acetate, washed several times with water, washed with brine, dried over magnesium sulfate and then concentrated under reduced pressure to provide 1-[2-(benzyloxy) ethyl]-1H-imidazo[4,5-c]quinoline as a dark oil.

$^1$H-NMR (300 MHz, DMSO-d6) δ 9.22 (s, 1H), 8.42 (s, 1H), 8.40 (s, 1H), 8.17 (m, 1H), 7.69 (m, 2H), 7.10–7.22 (m, 5H), 4.95 (t, J=5.1 Hz, 2H), 4.45 (s, 2H), 3.93 (t, J=5.1 Hz, 2H)

MS (CI) for $C_{19}H_{17}N_3O$ m/z 304 (MH$^+$), 214

Part B

3-Chloroperoxybenzoic acid (69.36 g of 77% maximum) was added in portions over a period of 15 minutes to a solution of 1-[2-(benzyloxy)ethyl]-1H-imidazo[4,5-c] quinoline (85.36 g, 281 mmol) in chloroform (800 mL). After 1 hour analysis by TLC (10% methanol in dichloromethane) showed that the reaction was complete. The reaction mixture was washed with saturated sodium bicarbonate (twice), washed with brine, dried over magnesium sulfate and then concentrated under reduced pressure to provide a solid. The solid was slurried with diethyl ether and then isolated by filtration to provide 1-[2-(benzyloxy) ethyl]-1H-imidazo[4,5-c]quinoline-5N-oxide as a dark yellow solid.

Part C

Phosphorous oxychloride (12.84 mL, 138 mmol) was slowly added to a mixture of 1-[2-(benzyloxy)ethyl]-1H-imidazo[4,5-c]quinoline-5N-oxide (40.0 g, 125 mmol) and anhydrous toluene (600 mL). The reaction mixture was allowed to stir for about 30 minutes and then the volatiles were removed under reduced pressure. The resulting red oil was dissolved in dichloromethane, washed twice with saturated sodium bicarbonate, and then concentrated under reduced pressure. An attempt to recrystallize the residue from ethyl acetate resulted in a gum. The material was taken up in ethyl acetate (500 mL) and then combined with triethylamine (25.34 g, 250 mmol). The solution was chilled in an ice bath and the precipitate was isolated by filtration. The material changed back into an oil shortly after filtration. The oil was taken up in dichloromethane, combined with the filtrate and then concentrated under reduced pressure to provide an oil. This material was partitioned between dichloromethane and 15% sodium hydroxide. The organic fraction was washed with brine, dried over magnesium sulfate and then concentrated under reduced pressure to provide an oil. This oil was further purified by flash chromatography (silica gel eluting first with dichloromethane, then with 2% methanol in dichloromethane and then with 5% methanol in dichloromethane) to provide ~21 g of 1-[2-(benzyloxy)ethyl]-4-chloro-1H-imidazo[4,5-c]quinoline.

$^1$H-NMR (300 MHz, DMSO-d6) δ 8.47 (s, 1H), 8.42 (dd, J=8.3, 1.5 Hz, 1H), 8.08 (dd, J=8.3, 1.5 Hz, 1H), 7.72 (m, 2H), 7.04–7.17 (m, 5H), 4.96 (t, J=5.1 Hz, 2H), 4.44 (s, 2H), 3.92 (t, J=5.1 Hz, 2H)

MS (CI) for $C_{19}H_{16}ClN_3O$ m/z 338 (MH$^+$), 309, 248, 214

Part D

Phenol (6.21 g, 66 mmol) was added in portions to a chilled suspension of sodium hydride (2.79 g of 60% in mineral oil, 69.7 mmol) in diglyme (25 mL). When bubbling had subsided, a solution of the material from Part C in diglyme (10 mL) was added in a single portion. The resulting solution was heated to 110° C. and stirred overnight. Analysis by TLC (3% methanol in dichloromethane) indicated that the reaction was complete. The solution was cooled to 0° C. and a brown precipitate formed. The diglyme was decanted off. The solid was slurried with hexane and then isolated by filtration. The solid was then slurried with water, isolated by filtration and dried in an oven overnight. The solid was recrystallized from isopropanol to provide 19.3 g of 1-[2-(benzyloxy)ethyl]-4-phenoxy-1H-imidazo[4,5-c]quinoline as a solid.

$^1$H-NMR (300 MHz, DMSO-d6) δ 8.39 (s, 1H), 8.32 (dd, J=8.3, 1.5 Hz, 1H), 7.69 (dd, J=8.3, 1.5 Hz, 1H), 7.46–7.59 (m, 4H), 7.12–7.33 (m, 8H), 4.93 (t, J=5.1 Hz, 2H), 4.47 (s, 2H), 3.94 (t, J=5.1 Hz, 2H)

MS (CI) for $C_{25}H_{21}N_3O_2$ m/z 396 (MH$^+$), 306, 288

Part E

Under a nitrogen atmosphere, triflic acid (29.0 g) was added dropwise to a solution of 1-[2-(benzyloxy)ethyl]-4-phenoxy-1H-imidazo[4,5-c]quinoline (7.65 g) in anhydrous dichloromethane (200 mL). When analysis by TLC (5% methanol in dichloromethane) indicated that the reaction was complete, the reaction mixture was concentrated under reduced pressure to provide an oil. This material was dissolved in ethyl acetate and then combined with triethylamine (10 eq.). The solution was diluted with additional ethyl acetate, washed with water, washed with brine, dried over magnesium sulfate and then concentrated under reduced pressure. The residue was recrystallized from ethyl acetate to provide ~4.8 g of 2-(4-phenoxy-1H-imidazo[4,5-c]quinolin-1-yl)ethanol as a white fluffy solid.

$^1$H-NMR (300 MHz, DMSO-d6) δ 8.34 (m, 1H), 8.32 (m, 1H), 7.70 (m, 1H), 7.46–7.60 (m, 4H), 7.25–7.31 (m, 3H), 5.06 (t, J=5.4 Hz, 11H), 4.76 (t, J=5.4 Hz, 2H), 3.90 (g, J=5.4 Hz, 2H)

Part F 3-(Bromomethyl)pyridine hydrobromide (0.638 g, 2.52 mmol) was added in a single portion with stirring to a solution containing 2-(4-phenoxy-1H-imidazo[4,5-c]quinolin-1-yl)ethanol (0.7 g, 2.29 mmol), benzyltrimethylammonium chloride (0.03 g), sodium hydroxide (28 mL of 50%) and dichloromethane (28 mL). After 3 hours analysis by TLC (5% methanol in dichloromethane) indicated that the reaction was complete. The reaction mixture was diluted with water (100 mL) and dichloromethane (100 mL). The layers were separated and the aqueous fraction was extracted with dichloromethane (100 mL). The organic fractions were combined, washed with brine, dried over magnesium sulfate and then concentrated under reduced pressure to provide a dark yellow solid. This material was purified by flash chromatography (silica gel eluting with 5% methanol in dichloromethane) to provide 0.74 g of 4-phenoxy-1-[2-(pyridin-3-ylmethoxy)ethyl]-1H-imidazo[4,5-c]quinoline as a bright yellow solid.

$^1$H-NMR (300 MHz, DMSO-d6) 8.42 (dd, J=4.9, 2.0 Hz, 1H), 8.38 (s, 2H), 8.33 (dd, J=8.3, 1.5 Hz, 1H), 7.70 (dd, J=8.3, 2.0 Hz, 1H), 7.46–7.59 (m, 5H), 7.22–7.33 (m, 4H), 4.96 (t, J=4.9 Hz, 2H), 4.52 (s, 2H), 3.98 (t, J=4.9 Hz, 2H)

MS (CI) for $C_{24}H_{20}N_4O_2$ m/z 397 (MH$^+$), 306, 288, 212, 110

Part G

4-Phenoxy-1-[2-(pyridin-3-ylmethoxy)ethyl]-1H-imidazo[4,5-c]quinoline (0.67 g, 1.69 mmol) and ammonium acetate (1.30 g, 16.9 mmol) were combined and heated to 150° C. After 5 hours analysis by TLC (10% methanol in dichloromethane) showed starting material. More ammonium acetate (5 g) was added. After 1 hour TLC indicated that the reaction was complete. The reaction mixture was allowed to cool to ambient temperature overnight. The resulting brown oil was combined with water (100 mL) and made basic (pH 9) with sodium bicarbonate. The product was extracted into dichloromethane (2×100 mL). The extracts were combined, washed with brine, dried over magnesium sulfate and then concentrated under reduced pressure to provide an off-white gummy solid. This material was purified by flash chromatography (silica gel eluting with 10% methanol in dichloromethane) to provide 0.40 g of a gummy white solid. This material was dissolved in methanol (10 mL). Hydrogen chloride/diethyl ether (5 eq) was added dropwise and the mixture was allowed to stir for 1 hour. The resulting precipitate was isolated by filtration, rinsed with diethyl ether and dried in a vacuum oven to provide 0.358 g of 1-[2-(pyridin-3-ylmethoxy)ethyl]-1H-imidazo[4,5-c]quinolin-4-amine hydrochloride as a light yellow solid, m.p. 229–231° C.

Analysis: Calculated for $C_{18}H_{17}N_5O \cdot 2.75$ HCl$\cdot 0.4$ H$_2$O: %C, 50.62; %H, 4.85; %N, 16.40; Found: %C, 50.44; %H, 4.96; %N, 16.19.

$^1$H-NMR (300 MHz, DMSO-d6) δ 8.78 (d, J=5.4 Hz, 1H), 8.71 (s, 1H), 8.56 (s, 1H), 8.34 (d, J=8.3 Hz, 1H), 8.26 (d, J=7.8 Hz, 1H), 7.90 (dd, J=7.8, 5.9 Hz, 1H), 7.84 (d, J=8.3 Hz, 1H), 7.72 (t, J=7.8 Hz, 1H), 7.54 (t, J=7.8 Hz, 1H), 4.98 (t, J=4.9 Hz, 2H), 4.69 (s, 2H), 4.04 (t, J=4.9 Hz, 2H)

MS (CI) for $C_{18}H_{17}N_5O \cdot HCl_{(11/4)} \cdot H_2O_{(2/5)}$ m/z 321 (MH$^+$), 229.

EXAMPLE 14

1-[2-(Pyridin-2-ylmethoxy)ethyl]-1H-imidazo[4,5-c]quinolin-4-amine

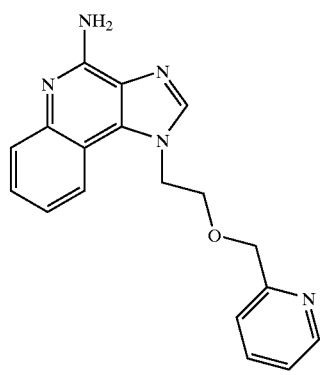

Part A

Using the general method of Example 13 Part F, 2-(4-phenoxy-1H-imidazo[4,5-c]quinolin-1-yl)ethanol (0.9 g, 2.95 mmol) was reacted with 2-picolyl chloride hydrogen chloride (0.53 g, 3.24 mmol) and the product purified to provide 0.65 g of 4-phenoxy-1-[2-(pyridin-2-ylmethoxy)ethyl]-1H-imidazo[4,5-c]quinoline.

¹H-NMR (300 MHz, DMSO-d6) 8.41 (m, 2H), 8.34 (dd, J=8.3, 1.5 Hz, 1H), 7.70 (dd, J=8.3, 1.5 Hz, 2H), 7.46–7.66 (m, 5H), 7.18–7.33 (m, 4H), 7.30 (d, J=7.8 Hz, 1H), 4.98 (t, J=4.9 Hz, 2H), 4.55 (s, 2H), 4.04 (t, J=4.9 Hz, 2H)

Part B

The material from Part A and ammonium acetate were combined and heated to 150° C. After 5 hours analysis by TLC (10% methanol in dichloromethane) indicated that the reaction was complete. The reaction mixture was allowed to cool to ambient temperature, then it was combined with water (100 mL) and made basic (pH 9) with sodium bicarbonate. The resulting white precipitate was isolated by filtration and then slurried with diethyl ether. The resulting white solid was isolated by filtration and then recrystallized from acetonitrile to provide 0.18 g of 1-[2-(pyridin-2-ylmethoxy)ethyl]-1H-imidazo[4,5-c]quinolin-4-amine as a white solid, m.p. 196–198° C.

Analysis: Calculated for $C_{18}H_{17}N_5O$: %C, 67.70; %H, 5.37; %N, 21.93; Found: %C, 67.86; %H, 5.31; %N, 22.13.

¹H-NMR (300 MHz, DMSO-d6) δ 8.43 (d, J=4.9 Hz, 2H), 8.20 (s, 1H), 8.09 (d, J=6.8 Hz, 1H), 7.63 (dt, J=8.3, 1.5 Hz, 2H), 7.43 (dt, J=8.3, 1.5 Hz, 1H), 7.19–7.24 (m, 2H), 7.12 (d, J=7.8 Hz, 1H), 6.53 (br s, 2H), 4.87 (t, J=5.1 Hz, 2H), 4.54 (s, 2H), 3.99 (t, J=5.1 Hz, 2H)

MS (CI) for $C_{18}H_{17}N_5O$ m/z 320 (MH⁺), 229, 211.

EXAMPLE 15

1-[2-(Pyridin-4-ylmethoxy)ethyl]-1H-imidazo[4,5-c]quinolin-4-amine

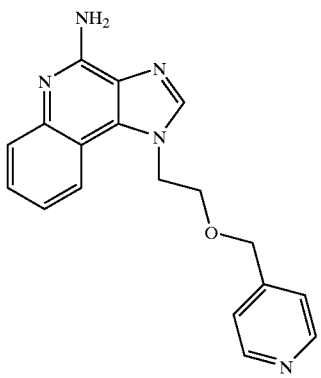

Part A

Using the general method of Example 13 Part F, 2-(4-phenoxy-1H-imidazo[4,5-c]quinolin-1-yl)ethanol (1.1 g, 3.61 mmol) was reacted with 4-picolyl chloride hydrogen chloride (0.649 g, 3.96 mmol) and the product purified to provide ~0.3 g of 4-phenoxy-1-[2-(pyridin-4-ylmethoxy)ethyl]-1H-imidazo[4,5-c]quinoline.

¹H-NMR (300 MHz, DMSO-d6) δ 8.41 (s, 1H), 8.39 (s, 1H), 8.34 (dd, J=7.8, 1.5 Hz, 2H), 7.70 (dd, J=7.8, 1.5 Hz, 1H), 7.46–7.60 (m, 4H), 7.25–7.33 (m, 3H), 7.10 (d, J=5.9 Hz, 2H), 5.00 (t, J=4.9 Hz, 2H), 4.53 (s, 2H), 4.00 (t, J=4.9 Hz, 2H)

MS (CI) for $C_{24}H_{20}N_4O_2$ m/z 397 (MH⁺), 306, 288, 212, 110

Part B

Using the general method of Example 14 Part B, 4-phenoxy-1-[2-(pyridin-4-ylmethoxy)ethyl]-1H-imidazo[4,5-c]quinoline (0.25 g) was aminated to provide 0.14 g of 1-[2-(pyridin-4-ylmethoxy)ethyl]-1H-imidazo[4,5-c]quinolin-4-amine as a solid, m.p. 159–161° C.

Analysis: Calculated for $C_{18}H_{17}N_5O$: %C, 67.70; %H, 5.37; %N, 21.93; Found: %C, 67.37; %H, 5.31; %N, 22.49.

¹H-NMR (300 MHz, DMSO-d6) δ 8.40 (dd, J=4.4, 1.5 Hz, 2H), 8.20 (s, 1H), 8.09 (d, J=8.3 Hz, 1H), 7.62 (d, J=8.3 Hz, 1H), 7.43 (m, 1H), 7.21 (m, 1H), 7.10 (d, J=5.4 Hz, 1H), 6.54 (br s, 2H), 4.87 (t, J=5.1 Hz, 2H), 4.51 (s, 2H), 3.94 (t, J=5.1 Hz, 2H)

MS (CI) for $C_{18}H_{17}N_5O$ m/z 320 (MH⁺), 229, 136

EXAMPLE 16

1-{2-[(3,5-Dimethylisoxazol-4-yl)methoxy]ethyl }-1H-imidazo[4,5-c]quinolin-4-amine

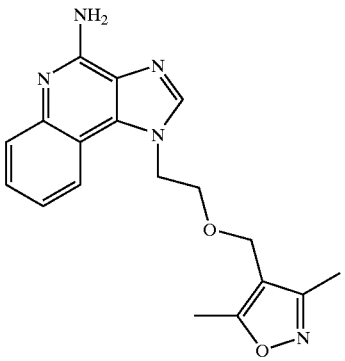

Part A

Using the general method of Example 13 Part F, 2-(4-phenoxy-1H-imidazo[4,5-c]quinolin-1-yl)ethanol (0.82 g, 2.69 mmol) was reacted with 4-(chloromethyl)-3,5-dimethylisoxazole (0.43 g, 2.95 mmol) and purified to provide 0.59 g of 1-{2-[(3,5-dimethylisoxazol-4-yl)methoxy]ethyl}-4-phenoxy-1H-imidazo[4,5-c]quinoline as a white foamy solid.

¹H-NMR (300 MHz, DMSO-d6) δ 8.29–8.32 (m, 2H), 7.70 (dd, J=7.8, 1.5 Hz, 1H), 7.46–7.60 (m, 4H), 7.25–7.32 (m, 3H) 4.89 (t, J=5.1 Hz, 2H), 4.24 (s, 2H), 3.89 (t, J=4.9 Hz, 2H), 2.16 (s, 3H), 1.93 (s, 3H)

MS (CI) for $C_{24}H_{22}N_4O_3$ m/z 415 (MH⁺), 306, 212, 112

Part B

Using the general method of Example 14 Part B, the material from Part A was aminated to provide 0.39 g of 1-{2-[(3,5-dimethylisoxazol-4-yl)methoxy]ethyl}-1H-imidazo[4,5-c]quinolin-4-amine as a white solid, m.p. 213–215° C.

Analysis: Calculated for $C_{18}H_{19}N_5O_2$: %C, 64.08; %H, 5.68; %N, 20.76; Found: %C, 64.02; %H, 5.53; %N, 21.01.

¹H-NMR (300 MHz, DMSO-d6) δ 8.12 (s, 1H), 8.05 (dd, J=8.3, 1.0 Hz, 1H), 7.61 (dd, J=8.3, 1.0 Hz, 1H), 7.43 (m, 1H), 7.21 (m, 1H), 6.52 (br s, 2H), 4.79 (t, J=5.1 Hz, 2H), 4.23 (s, 2H), 3.85 (t, J=5.1 Hz, 2H), 2.20 (s, 3H), 1.97 (s, 3H)

MS (CI) for $C_{18}H_{19}N_5O_2$ m/z 338 (MH⁺), 229, 112

EXAMPLE 17
1-(2-{[3-(Pyrimidin-2-yl)-2-propynyl]oxy}ethyl)-1H-imidazo[4,5-c]quinolin-4-amine trifluoroacetate

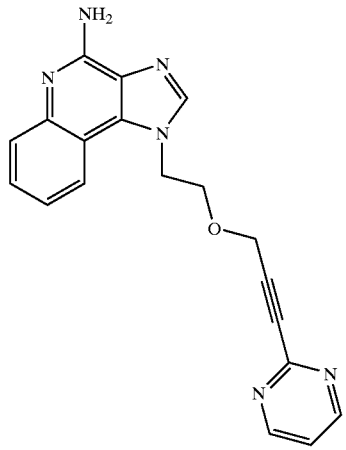

Under a nitrogen atmosphere, 1-[2-(2-propynyloxy)ethyl]-1H-imidazo[4,5-c]quinolin-4-amine (1.0 g, 3.7 mmol), triethylamine (1.0 g, 9.7 mmol) and anhydrous N,N-dimethylformamide (20 mL) were combined. The resulting solution was heated to 65° C. Copper (I) iodide (0.07 g, 0.4 mmol), dichlorobis(triphenylphosphine)palladium(II) (0.13 g, 0.2 mmol) and 2-bromopyrimidine (0.65 g, 4.1 mmol) were added and the reaction mixture was stirred at 65° C. overnight. The N,N-dimethylformamide was removed under reduced pressure to provide crude product as a tar. This tar was purified first by column chromatography (silica gel eluting with dichloromethane) and then by semi-preparative HPLC using Method A to provide 0.05 g of 1-(2-{[3-(pyrimidin-2-yl)-2-propynyl]oxy}ethyl)-1H-imidazo[4,5-c]quinolin-4-amine trifluoroacetate as a spongy white solid, m.p. 214–215° C.

Analysis: Calculated for $C_{19}H_{16}N_6O \cdot 1.5\ C_2HF_3O_2 \cdot 0.3\ H_2O$: %C, 50.67; %H, 3.51; %N, 16.12; Found: %C, 50.67; %H, 3.11; %N, 16.14.

$^1$H-NMR (300 MHz; DMSO-$d_6$) δ (ppm) 9.169(s, 1H), 8.646(s, 2H), 8.497(s, 1H), 8.328(d,J=8.3 Hz, 1H), 7.773(d, J=6.9 Hz, 1H), 7.703(t,J=6.7 Hz, 1H), 7.558(t,J=7.2 Hz, 1H), 4.942(t,J=4.8 Hz, 2H), 4.447(s, 2H), 4.073(t,J=4.9 Hz, 2H).

EXAMPLE 18
1-(2-{[3-(Pyrid-4-yl)-2-propynyl]oxy}ethyl)-1H-imidazo[4,5-c]quinolin-4-amine bis(trifluoroacetate)

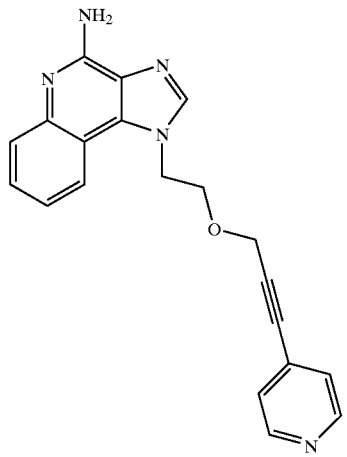

Under a nitrogen atmosphere, 1-[2-(2-propynyloxy)ethyl]-1H-imidazo[4,5-c]quinolin-4-amine (0.5 g, 1.9 mmol), triethylamine (0.5 g, 4.9 mmol), copper (I) iodide (0.036 g, 0.2 mmol), 4-bromopyridine (0.51 g, 2.6 mmol) and acetonitrile (20 mL) were combined and stirred at ambient temperature.

Dichlorobis(triphenylphosphine)palladium(II) (0.066 g, 0.1 mmol) was added. The reaction mixture was heated at reflux overnight. The acetonitrile was removed under reduced pressure. The residue was taken up in dichloromethane and methanol and then put through a basic alumina column. The fractions were combined and concentrated under reduced pressure. The residue was triturated with acetonitrile. The resulting solid was isolated by filtration and then purified by semi-preparative HPLC using Method A to provide 0.1 g of 1-(2-{[3-(pyrid-4-yl)-2-propynyl]oxy}ethyl)-1H-imidazo[4,5-c]quinolin-4-amine bis(trifluoroacetate) as a gray fluffy solid, m.p. 135° C. (dec.).

Analysis: Calculated for $C_{20}H_{17}N_5O \cdot 2.0\ C_2HF_3O_2 \cdot 0.5\ H_2O$: %C, 49.66; %H, 3.47; %N, 12.06; Found: %C, 49.59; %H, 3.51; %N, 12.22.

$^1$H-NMR (300 MHz; DMSO-$d_6$) δ (ppm) 9.063(bs,2H), 8.551(d,J=5.2 Hz, 2H), 8.498(s, 1H), 8.335(d,J=7.7 Hz, 1H), 7.795(d,J=6.9 Hz, 1H), 7.727(t,J=8.3 Hz, 1H), 7.564(t,J=8.3 Hz, 1H), 7.139(d,J=5.7 Hz, 2H), 4.942(t,J=4.8 Hz, 2H), 4.427(s, 2H), 4.056(t, J=4.8 Hz, 2H).

EXAMPLE 19
1-(2-{[3-(Fur-3-yl)-2-propynyl]oxy}ethyl)-1H-imidazo[4,5-c]quinolin-4-amine trifluoroacetate

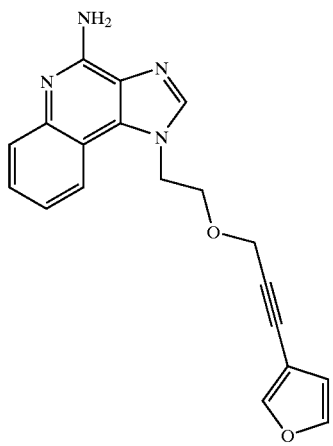

Under a nitrogen atmosphere, 1-[2-(2-propynyloxy)ethyl]-1H-imidazo[4,5-c]quinolin-4-amine (0.5 g, 1.9 mmol), triethylamine (0.5 g, 4.9 mmol), copper (I) iodide (0.036 g, 0.2 mmol), 3-bromofuran (0.38 g, 2.6 mmol) and anhydrous N,N-dimethylfonnamide (20 mL) were combined and stirred at ambient temperature. Dichlorobis(triphenylphosphine)palladium(II) (0.066 g, 0.1 mmol) was added. The reaction mixture was heated at 80° C. overnight. The reaction mixture was allowed to cool to ambient temperature and then it was diluted with dichloromethane. The resulting fine brown precipitate was removed by filtration. The filtrate was concentrated under reduced pressure. The residue was dissolved into a minimum amount of N,N- dimethylformamide and put through a silica gel column. The appropriate fractions were combined and concentrated under reduced pressure. The residue was purified by semi-preparative HPLC using Method A to provide 0.1 g of 1-(2-{[3-(fur-3-yl)-2-propynyl]oxy}ethyl)-1H-imidazo[4,5-c]quinolin-4-amine trifluoroacetate as a fluffy ivory solid, m.p. 160–162° C.

Analysis: Calculated for $C_{19}H_{16}N_4O_2 \cdot C_2HF_3O_2 \cdot 0.25$ $H_2O$: %C, 55.94; %H, 3.91; %N, 12.42; Found: %C, 55.57; %H, 3.43; %N, 12.45.

$^1$H-NMR (300 MHz; DMSO-$d_6$) δ (ppm) 8.859(bs,2H), 8.473(s, 1H), 8.32(d,J=8.3 Hz, 1H), 7.849(s, 1H), 7.813(d, J=7.3 Hz, 1H), 7.714(t,J=8.5 Hz, 1H), 7.697(d,J=2 Hz, 1H), 7.551(t,J=6.8 Hz, 1H), 6.409(d,J=1.9 Hz, 1H), 4.919(t,J=5.5 Hz, 2H), 4.337(s, 2H), 4.002(t, J=4.8 Hz, 2H).

EXAMPLE 20

4-{3-[2-(4-Amino-1H-imidazo[4,5-c]quinolin-1-yl) ethoxy]-propyn-1-yl}thiophen-2-ylcarboxaldehyde trifluoroacetate

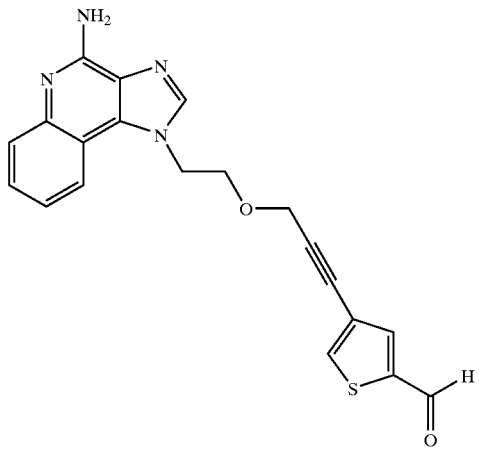

Using the general method of Example 20, 1-[2-(2-propynyloxy)ethyl]-1H-imidazo[4,5-c]quinolin-4-amine (0.5 g, 1.9 mmol) was reacted with 3-bromo-2-thiophenecarboxaldehyde (0.5 g, 2.6 mmol) and the crude product purified by semi-preparative HPLC using Method A to provide 0.13 g of 4-{3-[2-(4-amino-1H-imidazo[4,5-c]quinolin-1-yl)ethoxy]-propyn-1-yl}-thiophen-2-ylcarboxaldehyde trifluoroacetate as a fluffy ivory solid, m.p. 195° C.

Analysis: Calculated for $C_{20}H_{16}N_4O_2S \cdot C_2HF_3O_2$: %C, 53.88; %H, 3.49; %N, 11.42; Found: %C, 54.16; %H, 3.21; %N, 11.36.

$^1$H-NMR (300 MHz; DMSO-$d_6$) δ (ppm) 9.874(s, 1H), 8.972(bs,2H), 8.483(s, 1H), 8.322(d,J=7.9 Hz, 1H), 8.076(s, 1H), 7.771(d,J=8.3 Hz, 1H), 7.736(s, 1H), 7.71(t,J=8.4 Hz, 1H), 7.555(t,J=6.9 Hz, 1H), 4.928(t,J=5.3 Hz, 2H), 4.371(s, 2H), 4.043(t, J=4.8 Hz, 2H).

EXAMPLE 21

1-(2-{[3-(Pyrid-2-yl)-2-propynyl]oxy}ethyl)-1H-imidazo[4,5-c]quinolin-4-amine trifluoroacetate

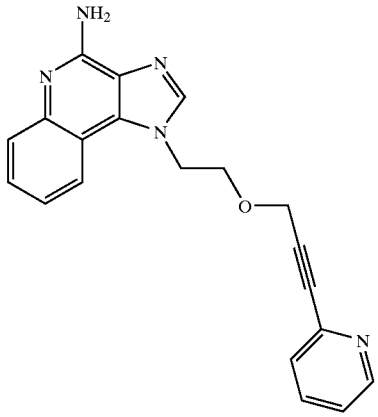

Using the general method of Example 19, 1-[2-(2-propynyloxy)ethyl]-1H-imidazo[4,5-c]quinolin-4-amine (0.5 g, 1.9 mmol) was reacted with 2-bromopyridine (0.51 g, 2.6 mmol) and the crude product purified by semi-preparative HPLC using Method A to provide 0.1 g of 1-(2-{[3-(pyrid-2-yl)-2-propynyl]oxy}ethyl)-1H-imidazo[4,5-c]quinolin-4-amine trifluoroacetate as a gray fluffy solid, m.p. 129–131° C.

Analysis: Calculated for $C_{20}H_{17}N_5O \cdot 1.75 \, C_2HF_3O_2 \cdot 0.25$ $H_2O$: %C, 51.56; %H, 3.55; %N, 12.80; Found: %C, 51.80; %H, 3.20; %N, 13.11.

$^1$H-NMR (300 MHz; DMSO-$d_6$) δ (ppm) 9.013(bs,2H), 8.516(s, 1H), 8.495(s, 1H), 8.331(d,J=8.2 Hz, 1H), 7.75(m, 3H), 7.553(t,J=8.2 Hz, 1H), 7.375(dd,J=7.8;4.9 Hz, 1H), 7.23(d,J=7.8 Hz, 1H), 4.944(t,J=5.4 Hz, 2H), 4.418(s, 2H), 4.059(t,J=4.8 Hz, 2H).

EXAMPLES 22–26

The compounds in the table below were prepared according to the synthetic method of Reaction Scheme I above using the following general method.

The 4-amino-1H-imidazo[4,5-c]quinolin-1-yl alcohol (25 mg) was placed in a 2 dram (7.4 mL) vial. Sodium hydride (1.2 eq of 60% in mineral oil) and N,N-dimethylformamide (1 mL) were added. The vial was placed on a sonicator for about 15 to 30 minutes at ambient temperature to allow the alkoxide to form. The halide (1.2 eq) was added and the vial was placed back on the sonicator for about 15 to 120 minutes at ambient temperature. The reaction mixture was analyzed by LC/MS to confirm the formation of the desired product. The reaction mixture was purified by semi-preparative HPLC. The semi-prep HPLC fractions were analyzed by LC-APCI/MS and the appropriate fractions were combined and lyophilized to provide the trifluoroacetate salt of the desired product, which was confirmed by accurate mass and $^1$H NMR spectroscopy. The table below shows the structure of the free base, the theoretical mass (TM), and the measured mass (MM) or nominal mass (NM).

| Example # | Structure of the Free Base | Purification Method | Mass Measurement (Da.) |
|---|---|---|---|
| 22 | | A | TM = 326.1743<br>MM = 326.1739 |
| 23 | | A | TM = 392.1597<br>MM = 392.1584 |
| 24 | | A | TM = 450.1281<br>MM = 450.1285 |
| 25 | | A | TM = 422.0968<br>MM = 422.0966 |

| Example # | Structure of the Free Base | Purification Method | Mass Measurement (Da.) |
|---|---|---|---|
| 26 | 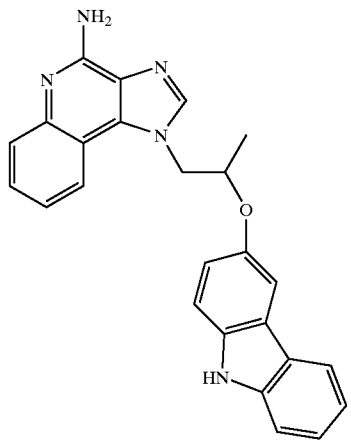 | A | TM = 364<br>NM[M + H]$^{+1}$ = 365 |

EXAMPLE 27

1-{2-Methyl-1-[(pyrid-2-yloxy)methyl]propyl}-1H-imidazo[4,5-c]quinoline-4-amine trifluoroacetate

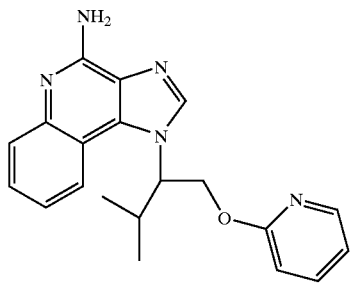

Using the general method of Examples 22–26 above, 2-(4-amino-1H-imidazo[4,5-c]quinolin-1-yl)-3-methylbutan-1-ol was reacted with 2-(trifluoromethylsulfonyloxy)pyridine and the crude product purified via semi-preparative HPLC using Method A to provide 1-{2-methyl-1-[(pyrid-2-yloxy)methyl]propyl}-1H-imidazo[4,5-c]quinoline-4-amine as the trifluoroacetate salt. TM=347.1746, MM=347.1740

EXAMPLE 28

1-{1-[(pyrid-2-yloxy)methyl]propyl}-1H-imidazo[4,5-c]quinoline-4-amine trifluoroacetate

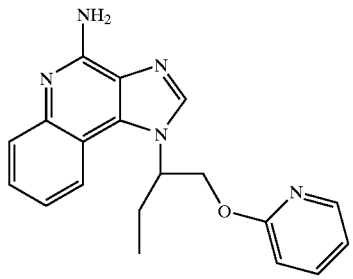

Using the general method of Examples 22–26 above 2-(4-amino-1H-imidazo[4,5-c]quinolin-1-yl)-3-methylbutan-1-ol was reacted with 2-(trifluoromethyl-sulfonyloxy)pyridine and the crude product purified via semi-preparative HPLC using Method B to provide 1-{1-[(pyrid-2-yloxy)methyl]propyl}-1H-imidazo[4,5-c]quinoline-4-amine as the trifluoroacetate salt. TM=333.1590, MM=333.1598

EXAMPLE 29

1-[2-(9H-carbazol-3-yloxy)propyl]-1H-imidazo[4,5-c]quinolin-4-amine trifluoroacetate

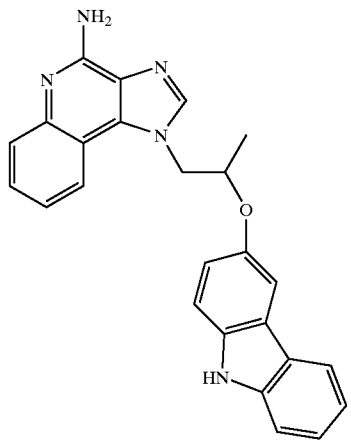

A 1 mL portion of a solution prepared by dissolving 0.5 g of 1-(4-amino-1H-imidazo[4,5-c]quinolin-1-yl)propan-2-ol in N,N-dimethylfornamide (20 mL) was added to a 2 dram (7.4 mL) glass vial containing 2-hydroxycarbazole (38 mg, 2 eq.). Triphenylphosphine (54 mg, 2 eq.) dissolved in N,N-dimethylformamide (1 mL) was added to the vial. The resulting slurry was sonicated to dissolve the phenol. Diethyl azidocarboxylate (36 mg, 2 eq.) was added neat. The reaction mixture was sonicated for about 30 minutes and then shaken overnight at ambient temperature. The solvent was removed and the residue was purified by semi-preparative HPLC using Method A. The compound was provided as the trifluoroacetate salt. TM=407, NM[M+H]$^+{}_1$=408.

EXAMPLE 30

1-{2-[(3-thien-2-ylprop-2-ynyl)oxy]ethyl}-1H-imidazo[4,5-c]quinolin-4-amine

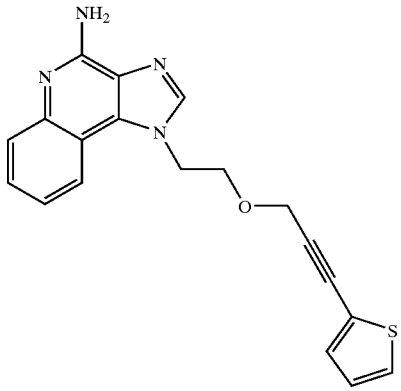

Part A

Using the general method of Example 1 Part B, 2-(1H-imidazo[4,5-c]quinolin-1-yl)ethyl(2-propynyl)ether was oxidized to provide 67.5 g of 1-[2-(2-propynyloxy)ethyl]-1H-imidazo[4,5-c]quinoline-5N-oxide as a tan solid.

MS (CI) for $C_{15}H_{14}N_3O_2$ m/z 268 (MH$^+$), 252, 214.

Part B

A dried round bottom flask was charged with a stir bar, 1-[2-(2-propynyloxy)ethyl]-1H-imidazo[4,5-c]quinioline-5N-oxde (57.5 g, 215.1 mmol), anhydrous toluene (200 mL) and anhydrous dimethyl formamide (400 mL) under a nitrogen atmosphere. Phosphorus oxychloride (23 mL, 247.4 mmol) was added dropwise over 20 minutes to this mixture leading to a modest exothermn (~40° C.). The reaction was judged complete after 1.25 hours at ambient temperature. The volatiles were removed under reduced pressure and the resulting solid was partitioned between chloroform and 10% aqueous sodium carbonate. The aqueous layer was extracted with chloroform; the organic fractions were combined, dried with anhydrous magnesium sulfate, filtered and concentrated under reduced pressure. The resulting brown solid was dried at 60° C., under vacuum, for 4 hours to obtain 36.6 g of 4-chloro-1-[2-(prop-2-ynyloxy)ethyl]-1H-imidazo[4,5-c]quinoline as a powder.

MS (CI) for $C_{15}H_{12}ClN_3O$ m/z 286 (MH$^+$), 246, 204.

Part C

A dried round bottom flask was charged with a stir bar, sodium hydride (8.15 g, 203.9 mmol) and anhydrous 2-methoxyethyl ether (diglyme, 100 mL) while under a nitrogen atmosphere and at ambient temperature. Phenol (20.7 g, 220.2 mmol) was added in several portions as a solid and the resulting solution stirred under a nitrogen atmosphere until gas evolution ceased. 4-chloro-1-[2-(prop-2-ynyloxy)ethyl]-1H-imidazo[4,5-c]quinoline (46.6 g, 163.1 mmol) was added neat and the solution was heated to 110° C. After 15.5 hours, a preformed solution of sodium phenoxide (phenol 5 g, 53.1 mmol and sodium hydride 1.91 g, 47.8 mmol) in diglyme (20 mL) was added to the reaction solution and heating was increased to 165° C. The reaction was judged complete after 1 hour at 165° C. After cooling to less than 70° C., the volatiles were removed under reduced pressure and the resulting brown solid was partitioned between chloroform and saturated aqueous sodium carbonate. The aqueous fraction was extracted with chloroform; the combined organic fractions were dried with anhydrous magnesium sulfate, filtered and then concentrated under reduced pressure to provide a brown solid. The solid was recrystallized from acetonitrile with a small amount of dimethyl formamide to provide 25 g of 4-phenoxy-1-[2-(prop-2-ynyloxy)ethyl]-1H-imidazo[4,5-c]quinoline as a crystalline solid.

MS (CI) for $C_{21}H_{17}N_3O_2$ m/z 344 (MH$^+$), 306, 288.

Part D

Using the general method of Example 3 Part A, 4-phenoxy-1-[2-(prop-2-ynyloxy)ethyl]-1H-imidazo[4,5-c]quinoline (10 g, 29.4 mmol) was reacted with 2-iodothiophene (3.6 mL, 32.3 mmol). The glassy solid obtained from purification by chromatography over silica gel (98/2 dichloromethane/methanol) was triturated with ether to provide 5.3 g of 4-phenoxy-1-{2-[(3-thien-3-ylprop-2-ynyl)oxy]ethyl}-1H-imidazo[4,5-c]quinoline as a gray powder.

MS (CI) for $C_{25}H_{19}N_3O_2S$ m/z 426 (MH$^+$), 306, 288.

Part E

4-Phenoxy-1-{2-[(3-thien-3-ylprop-2-ynyl)oxy]ethyl}-1H-imidazo[4,5-c]quinoline (3.2 g, 7.52 mmol) and ammonium acetate (32 g, 415 mmol) were melted together in a dried round bottom heated to 150° C. under a nitrogen atmosphere. After 2 hrs additional ammonium acetate (10 g, 129 mmol) was added. The reaction was judged complete after a total of 4 hours. The melted solids were cooled to ambient temperature and basified with 1N aqueous potassium hydroxide to a pH of 13. The aqueous mixture was extracted with dichloromethane (3x); the combined organic fractions were washed with brine, dried over anhydrous magnesium sulfate, filtered and then concentrated under reduced pressure. The resulting solid was purified by chromatography over silica gel (98/2 dichloromethane/methanol), then triturated with ether to provide 0.812 g of 1-{2-[(3-thien-2-ylprop-2-ynyl)oxy]ethyl}-1H-imidazo[4,5-c]quinolin-4-amine as a white powder, m.p. 148–150° C.

Analysis. Calculated for $C_{19}H_{16}N_4OS$: %C, 65.50; %H, 4.63; %N, 16.08. Found: %C, 65.42; %H, 4.65; %N, 16.11

$^1$H NMR (300 MHz, DMSO) δ 8.16 (s, 1 H), 8.11 (d, J=6.8 Hz, 1 H), 7.60 (m, 2 H), 7.43 (t, J=6.8 Hz, 1 H), 7.20–7.25 (m, 2 H), 7.04 (dd, J=4.9, 3.9 Hz, 1 H), 6.58 (s, 2 H), 4.84 (t, J=5.4, 2 H), 4.41 (s, 2 H), 3.99 (t, J=5.4, 2 H)

MS (CI) for $C_{19}H_{16}N_4OS$ m/z 349 (MH$^+$), 229, 185.

EXAMPLE 31

1-{2-[(1-methyl-1H-indol-2-yl)methoxy]ethyl}-1H-imidazo[4,5-c]quinolin-4-amine

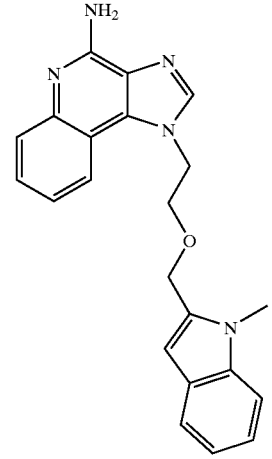

Part A

Using the general method of Example 30 Part D, 4-phenoxy-1-[2-(prop-2-ynyloxy)ethyl]-1H-imidazo[4,5-c]quinoline (3.16 g, 9.20 mmol) was reacted with 2-iodo-N,N-dimethylaniline (2.5 g, 10.1 mmol) to provide a 1.0 g of 1-{2-[(1-methyl-1H-indol-2-yl)methoxy]ethyl}-4-phenoxy-1H-imidazo[4,5-c]quinoline as a pale yellow crystalline solid.

MS (CI) for $C_{28}H_{24}N_4O_2$ m/z 449 (MH$^+$), 306, 186.

Part B

1-{2-[(1-Methyl-1H-indol-2-yl)methoxy]ethyl}-4-phenoxy-1H-imidazo[4,5-c]quinoline (0.78 g, 1.74 mmol) was partially converted to the desired product by exposure to ammonia, (7% in methanol, 20 mL) for 52 hours at 160° C. in a bomb. The volatiles were removed under reduced pressure and the material was reacted with more ammonia (7% in methanol, 20 mL) for 80 hours at 160° C. to completely consume the starting material. The solid was removed by filtration and the filtrate was concentrated under reduced vacuum. The resulting material was purified by chromatography over silica gel (9/1 dichloromethane/methanol). The resulting solid was recrystallized from dimethyl formamide to provide 0.121 g of 1-{2-[(1-methyl-1H-indol-2-yl)methoxy]ethyl}-1H-imidazo[4,5-c]quinolin-4-amine as white, flat crystals, m.p. 243–245° C.

Analysis. Calculated for $C_{22}H_{21}N_5O \cdot (C_3H_7ON)_{0.20}$: %C, 70.50; %H, 5.81; %N, 18.75. Found: %C, 70.72; %H, 5.70; %N, 18.36

$^1$H NMR (300 MHz, DMSO) δ 8.13 (s, 1 H), 8.05 (d, J=8.3 Hz, 1 H), 7.60 (d, J=9.3, 1 H), 7.36–7.47 (m, 3 H), 7.10–7.20 (m, 2 H), 6.98 (t, J=7.3 Hz, 1 H), 6.58 (brs, 2 H), 6.36 (s, 1 H), 4.82 (t, J=4.9, 2 H), 4.64 (s, 2 H), 3.92 (t, J=4.9, 2 H), 3.52 (s, 3 H)

MS (CI) for $C_{22}H_{21}N_5O$ m/z 372 (MH$^+$), 229, 144.

EXAMPLE 32

1-[2-(3-thien-2-ylpropoxy)ethyl]-1H-imidazo[4,5-c]quinolin-4-amine

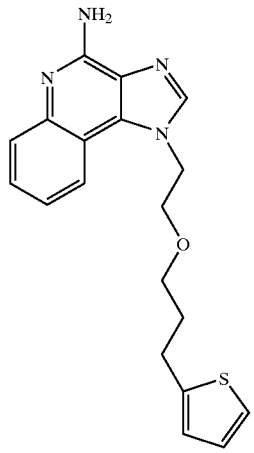

Part A

A dried round bottom flask was charged with a stir bar, 2-(1H-imidazo[4,5-c]quinolin-1-yl)ethyl (2-propynyl)ether (11.78 g, 46.88 mmol), anhydrous triethylamine (14 mL, 121.9 mmol), 2-iodothiophene (5.7 mL, 51.57 mmol) and anhydrous dimethyl formamide(130 mL) under a nitrogen atmosphere and heated to 80° C. After 5 minutes dichlorobis(triphenylphosphine)palladium(II) (0.658 g, 0.937 mol) and copper(I) iodide (0.357 g, 1.875 mmol) were added neat to the solution. The reaction was judged complete after 50 minutes. The volatiles were removed under reduced pressure and the resulting solid partitioned between dichloromethane and 0.5N aqueous potassium hydroxide. The aqueous fraction was extracted with dichloromethane (3×); the combined organic fractions were dried with anhydrous magnesium sulfate, filtered and concentrated under reduced pressure to provide a brown solid. The glassy solid obtained from purification by chromatography over silica gel (98/2 dichloromethane/methanol) was triturated with ether to provide 9.5 g of 1-{2-[(3-thien-2-ylprop-2-ynyl)oxy]ethyl}-1H-imidazo[4,5-c]quinolin as a tan solid.

MS (CI) for $C_{19}H_{15}N_3OS$ m/z 334 (MH$^+$), 290, 214.

Part B

Using the general method of Example 3 Part B, 1-{2-[(3-thien-2-ylprop-2-ynyl)oxy]ethyl}-1H-imidazo[4,5-c]quinoline (9.5 g, 28.49 mmol) was reduced with palladium on carbon (10%, 1 g) in methanol (25 mL) to provide 9.1 g of 1-[2-(3-thien-2-ylpropoxy)ethyl]-1H-imidazo[4,5-c]quinoline as a brown oil.

MS (CI) for $C_{19}H_{19}N_3OS$ m/z 338 (MH$^+$), 214.

Part C

Using the general method of Example 1 Part B, 1-[2-(3-thien-2-ylpropoxy)ethyl]-1H-imidazo[4,5-c]quinoline was oxidized to provide 4.4 g of 1-[2-(3-thien-2-ylpropoxy)ethyl]-1H-imidazo[4,5-c]quinoline-5N-oxide as an unpurified tan solid.

MS (CI) for $C_{19}H_{19}N_3O_2S$ m/z 354 (MH$^+$), 338, 214.

Part D

Using the general method of Example 1 Part C, 1-[2-(3-thien-2-ylpropoxy)ethyl]-1H-imidazo[4,5-c]quinoline-5N-oxide (4.4 g, 12.45 mmol) was reacted with trichloroacetyl isocyanate (1.8 mL, 14.9 mmol) to provide 2,2,2-trichloro-N-{1-[2-(3-thien-2-ylpropoxy)ethyl]-1H-imidazo[4,5-c]quinolin-4-yl}acetamide as an unpurified glassy solid.

Part E

A dried round bottom flask was charged with a stir bar, 2,2,2-trichloro-N-{1-[2-(3-thien-2-ylpropoxy)ethyl]-1H-imidazo[4,5-c]quinolin-4-yl}acetamide and sodium methoxide (25% in methanol, 11 mL, 49.8 mmol) at ambient temperature. The reaction was judged complete after 30 hours. The volatiles were removed under reduced pressure. The resulting oil was purified with chromatography over silica gel (95/5 dichloromethane/methanol), semi-preparative HPLC using method A, and recrystallization from ethyl acetate/hexane to provide 43 mg of 1-[2-(3-thien-2-ylpropoxy)ethyl]-1H-imidazo[4,5-c]quinolin-4-amine as a white crystalline solid. m.p. 130.1–131.6° C.

Analysis. Calculated for $C_{19}H_{20}N_4OS \cdot (H_2O)_{0.30}$: %C, 63.77; %H, 5.80; %N, 15.66. Found: %C, 63.84; %H, 5.79; %N, 15.57

$^1$H NMR (300 MHz, DMSO) δ 8.16 (s, 1 H), 8.12 (d, J=8.3 Hz, 1 H), 7.62 (d, J=8.3 Hz, 1 H), 7.43 (t, J=7.3 Hz, 1 H), 7.20–7.26 (m, 2 H), 6.84 (dd, J=4.9, 3.4 Hz, 1 H), 6.62 (d, J=2.4 Hz, 1 H), 6.58 (s, 2 H), 4.79 (t, J=5.4 Hz, 2 H), 3.83 (t, J=5.4 Hz, 2 H), 3.35 (t, J=6.4, 2 H), 2.64 (t, J=7.8 Hz, 2 H), 1.69 (p, J=6.8, 6.3 Hz, 2 H).

MS (CI) for $C_{19}H_{20}N_4OS$ m/z 353 (MH$^+$), 211, 185.

EXAMPLE 33

1-[2-(3-Pyridin-3-ylpropoxy)ethyl]-1H-imidazo[4,5-c]quinolin-4-amine

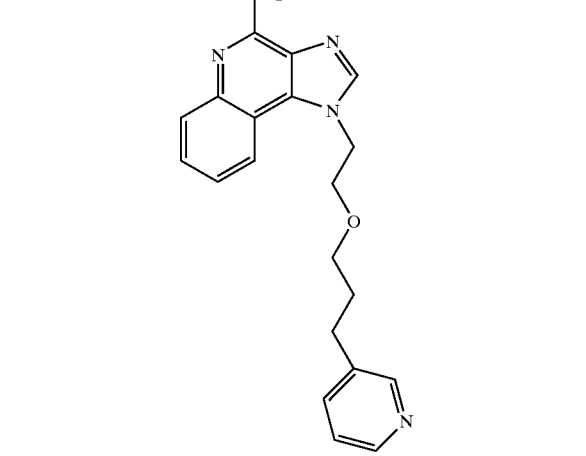

Part A

Under a nitrogen atmosphere, a solution of 2-aminobenzoic acid (100.0 g, 0.73 mol) in acetic anhydride (400 ml, 4.2 mol) was heated to reflux for 2 hours. The reaction was cooled to room temperature and the solvent was removed in vacuo. The residue was dissolved in glacial acetic acid (500 ml) and NaN$_3$ (49.77 g, 0.77 mol) was added. The mixture was stirred overnight at room temperature followed by concentration of the acetic acid in vacuo. The residue was dissolved in 10% NaOH (500 ml) solution and heated to reflux for 3.5 hours. The reaction was cooled to room temperature and then poured over a mixture of ice water (2 L) and HCl (150 ml). A white solid precipitated and was collected by vacuum filtration. The solid was dried in vacuo to yield 130.5 g of 2-(5-methyl-1H-tetrazol-1-yl) benzoic acid.

$^1$H NMR (300 MHz, DMSO-d$_6$) δ 8.12 (d, J=7.2 Hz, 1H), 7.91–7.78 (m, 2H), 7.72 (d, J=7.4 Hz, 1H), 2.37 (s, 3H);

MS (CI) m/e 205 (MH$^+$), 162 (M−N$_3$).

Part B

Under a nitrogen atmosphere, 2-(5-methyl-1H-tetrazol-1-yl)benzoic acid (89.7 g, 0.44 mol) was dissolved in acetone (1 L) and cesium carbonate (214.7 g, 0.66 mol) was added with vigorous stirring. Ethyl iodide (70.3 ml, 0.88 mol) was added dropwise and the reaction was heated to reflux for 4 hours. The reaction was cooled to room temperature and filtered. The acetone was removed in vacuo to yield a yellow solid which was dissolved in dichloromethane (800 ml) and washed with saturated sodium bicarbonate (200 ml). The organic fraction was dried (Na$_2$SO$_4$), filtered, and concentrated to yield 92.7 g of ethyl 2-(5-methyl-1H-tetrazol-1-yl) benzoate as a light yellow solid.

$^1$H NMR (300 MHz, DMSO-d$_6$) δ 8.14 (d, J=7.8 Hz, 1H), 7.89 (m, 2H), 7.79 (d, J=7.9 Hz, 1H), 4.08 (q, J=7.4 Hz, 2H), 2.40 (s, 3H), 1.04 (t, J=6.9 Hz, 3H);

MS (CI) m/e 233 (MH$^+$), 159.

Part C

Under a nitrogen atmosphere, ethyl 2-(5-methyl-1H-tetrazol-1-yl)benzoate (92.7 g, 0.34 mol) was dissolved in N,N-dimethylformamide (600 ml) and the solution was chilled in an ice water bath. Potassium ethoxide (67.2 g, 0.80 mol) was added slowly to the solution. After a few minutes, the ice water bath was removed and the reaction was stirred at room temperature for 3 hours. The reaction was treated with 100 ml of water and approximately 300–400 ml of solvent was removed in vacuo. The remainder of the reaction was poured over a solution of glacial acetic acid (125 ml) in ice water (2 L). A precipitate formed and the mixture was diluted with additional water (3 L). The solid was collected by vacuum filtration to yield 63.25 g of tetrazolo[1,5-a]quinolin-5-ol as a yellow solid.

$^1$H-NMR (300 MHz, DMSO-d$_6$) δ 8.54 (d, J=8.4 Hz, 1H), 8.27 (d, J=8.1 Hz, 1H), 7.99 (t, J=7.4 Hz, 1H), 7.80 (t, J=7.2 Hz, 1H), 7.04 (s, 1H);

MS (CI) m/e 187 (MH$^+$), 159.

Part D

Tetrazolo[1,5-a]quinolin-5-ol (63.25 g, 0.34 mol) was added to glacial acetic acid (630 ml) to form a thick off white suspension. The mixture was vigorously stirred while nitric acid (23.6 ml, 0.37 mol, 70% solution) was slowly added. The reaction was then heated from 25 to 80° C. over a period of 15 minutes. A yellow precipitate formed and the reaction was maintained at 80° C. for 5 minutes. The mixture was slowly cooled to 0° C. The solid was collected by filtration and then dried in vacuo to yield 60.0 g of 4-nitro-tetrazolo [1,5-a]quinolin-5-ol as a yellow solid.

$^1$H-NMR (300 MHz, DMSO-d$_6$) δ 8.35 (d, J=3.9 Hz, 1H),; 8.32 (d, J=3.2 Hz, 1H), 7.90 (t, J=7.3 Hz, 1H), 7.68 (t, J=8.2 Hz, 1H);

MS (CI) m/e 232 (MH$^+$), 204.

Part E

Under a nitrogen atmosphere, POCl$_3$ (16.42 ml, 0.17 mol) was slowly added to a chilled (0° C.) flask containing N,N-dimethylformamide (100 ml). The resulting solution was slowly warmed to room temperature and then added dropwise to a suspension of 4-nitro-tetrazolo[1,5-a] quinolin-5-ol in N,N-dimethylformamide (300 ml). The reaction was heated to 100° C. for 30 minutes. The orange/red solution was quenched by pouring over 1 liter of ice water. A yellow precipitate formed and was collected by filtration, redissolved in chloroform (approx. 750 ml), dried (Na$_2$SO$_4$), filtered, and concentrated in vacuo to yield 33.74 g of 5-chloro-4-nitrotetrazolo[1,5-a]quinoline as a yellow solid.

$^1$H NMR (300 MHz, DMSO-d$_6$) δ 8.78 (d, J=8.2 Hz, 1H),; 8.57 (d, J=8.3 Hz, 1H), 8.29–8.22 (m, 1H), 8.09–8.03 (m, 1H);

MS (CI) m/e 250 (MH$^+$).

Part F

5-Chloro-4-nitrotetrazolo[1,5-a]quinoline (28.86 g, 0.11 mol), dichloromethane (600 ml), and triethylamine (21.14 ml, 0.11 mol) were combined and the resulting solution was chilled to 0° C. 2-(3-Pyridin-3-ylpropoxy)ethylamine (22.9 g, 0.13 mol) was added dropwise. The reaction was allowed to slowly warm to room temperature, then stirred at room temperature for 1 hour and finally at reflux for 2 hours. The reaction was cooled to room temperature and then quenched with water (200 ml). The phases were separated and the aqueous layer was extracted with dichloromethane (3×50 ml). The combined organic fractions were washed with brine (100 ml), dried (Na$_2$SO$_4$), filtered and concentrated to yield a yellow solid. The solid was slurried in ethanol (150 ml) and filtered to provide 34.3 g of 4-nitro-N-[2-(3-pyridin-3-ylpropoxy)ethyl]tetrazolo[1,5-a]quinolin-5-amine.

$^1$H NMR (300 MHz, DMSO-d$_6$) δ 10.27 (bs, 1H), 8.69 (d, J=8.3 Hz, 1H), 8.54 (d, J=8.3 Hz, 1H), 8.37 (bs, 2H), 8.08 (t, J=7.7 Hz, 1H), 7.81 (t, J=7.2 Hz, 1H), 7.57 (d, J=7.3 Hz, 1H), 7.27 (dd, J=7.9, 5.0 Hz, 1H), 3.92 (m, 2H), 3.71 (t, J=5.4 Hz, 2H), 3.47 (t, J=6.0 Hz, 2H), 2.62 (t, J=7.4 Hz, 2H), 1.82 (m, 2H);

MS (CI) m/e 394 (MH$^+$), 366.

Part G

4-Nitro-N-[2-(3-pyridin-3-ylpropoxy)ethyl]tetrazolo[1,5-a]quinolin-5-amine (34.3 g, 87.2 mmol) was added to a 3 liter stainless steel pressure flask containing ethanol (1.25 L, absolute). Platinum on carbon (3.00 g, 5% w/w) was added and the flask was placed on a Parr hydrogenation apparatus. The reaction was shaken under 45 psi (3.15 Kg/cm$^2$) of hydrogen for 24 hours. The catalyst was removed by filtration through Celite™ and the Celite pad was washed with several portions of ethanol. The filtrate was concentrated in vacuo to provide 30.8 g of N$^5$-[2-(3-pyridin-3-ylpropoxy) ethyl]tetrazolo[1,5-a]quinoline-4,5-diamine as an orange/red oil. MS (CI) m/e 364 (MH$^+$), 336.

Part H

Triethyl orthoformate (21.1 ml, 127 mmol) was added to a solution of N$^5$-[2-(3-pyridin-3-ylpropoxy)ethyl]tetrazolo [1,5-a]quinoline-4,5-diamine (30.8 g, 84.7 mmol) in 1,2-dichloroethane (750 ml) and the reaction was heated to reflux for 3 hours. The reaction was cooled to room temperature and diluted with saturated sodium bicarbonate (200 ml). The phases were separated and the aqueous layer was extracted with dichloromethane (3×75 ml). The combined organic fractions were washed with brine (200 ml), dried (Na$_2$SO$_4$) and concentrated to provide an orange solid. The solid was triturated with diethyl ether and then filtered to yield 28.7 g of 6-[2-(3-pyridin-3-ylpropoxy)ethyl]-6H-imidazo[4,5-c]tetrazolo[1,5-a]quinoline as a tan/orange solid.

$^1$H-NMR (300 MHz, CDCl$_3$) δ 8.71 (dd, J=8.1, 1.3 Hz, 1H), 8.38 (dd, J=4.8, 1.5 Hz, 1H), 8.30 (d, J=2.1 Hz, 1H), 8.20 (d, J'7.7 Hz, 1H), 8.07 (s, 1H), 7.73 (m, 2H), 7.32 (dt, J=7.8, 1.9 Hz, 1H), 7.13 (dd, J=7.7, 4.8 Hz, 1H), 4.81 (t, J=5.1 Hz, 2H), 3.9 (t, J=5.1 Hz, 2H), 3.42 (t, J=6.2 Hz, 2H), 2.52 (t, J=7.5 Hz, 2H), 1.82–1.74 (m, 2H);

MS (CI) m/e 374 (MH+).

Part I

Triphenylphosphine (27.0 g, 115 mmol) was added to a solution of 6-[2-(3-pyridin-3-ylpropoxy)ethyl]-6H-imidazo[4,5-c]tetrazolo[1,5-a]quinoline (28.7 g, 76.9 mmol) in 1,2-dichlorobenzene (1 L). The reaction was heated at reflux temperature overnight. The dark red solution was cooled to room temperature and treated with 1N HCl (225 ml). A tan precipitate formed. The resulting mixture was concentrated in vacuo to yield a dark red/brown solid. This material was treated with 500 ml water and vigorously stirred. Excess triphenylphosphine and triphenylphosphine oxide formed as precipitates and were removed by vacuum filtration. The solid was washed with several portions of water followed by a final wash with dilute HCl (1:5, 1N HCl:water). The red/brown filtrate was collected, washed with ether (3×150 ml), and treated with 10% NaOH solution until the pH reached 12. The crude product formed as a tan precipitate and was collected by filtration. Purification of the crude material was accomplished by treatment (2×) with activated charcoal (Darco-G60) in refluxing methanol. The charcoal was removed by filtration. The desired product formed as a precipitate during concentration of the filtrate.

The solid was collected by vacuum filtration washed with diethyl ether, and dried under vacuum to provide 17 g of 1-[2-(3-pyridin-3-ylpropoxy)ethyl]-1H-imidazo[4,5-c]quinolin-4-amine as a tan solid, m.p. 125.0–128.0° C.

$^1$H NMR (300 MHz, DMSO-d$_6$) δ 8.33 (d, J=4.8 Hz, 1H), 8.24 (s, 1H), 8.18 (s, 1H), 8.13 (d, J=7.7 Hz, 1H), 7.63 (d, J=8.4 Hz, 1H), 7.45 (t, J=6.8 Hz, 1H), 7.33–7.21 (m, 2H), 7.16 (dd, J=7.7, 4.8 Hz, 1H), 6.62 (s, 2H), 4.80 (t, J=4.8 Hz, 2H), 3.82 (t, J=4.9 Hz, 2H), 3.30 (t, J=6.3 Hz, 2H), 2.39 (t, J=7.3 Hz, 2H), 1.64 (m, 2H);

MS (CI) m/e 348 (MH+);

Anal calcd for $C_{20}H_{21}N_5O$*0.08 $H_2O$: C, 68.89; H, 6.11; N, 20.09. Found: C, 68.49; H, 5.95; N, 20.08.

EXAMPLE 34

2-Methyl-1-[2-(3-pyridin-3-ylpropoxy)ethyl]-1H-imidazo[4,5-c]quinoline-4-amine

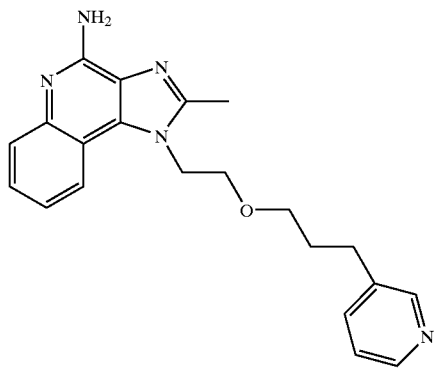

Part A

Under an atmosphere of nitrogen, $N^5$-[2-(3-pyridin-3-ylpropoxy)ethyl]tetrazolo[1,5-a]quinoline-4,5-diamine (0.70 g, 1.92 mmol) was dissolved in 1,2-dichloroethane (15 ml). Triethyl orthoacetate (0.53 ml, 2.88 mmol) was added via syringe and the reaction was heated to reflux for 3 hours. Analysis by thin layer chromatography (95/5 chloroform/methanol) showed complete consumption of the diamine. The reaction was quenched by the addition of water (15 ml). The phases were separated and the aqueous fraction was extracted with dichloromethane (3×10 ml). The combined organic fractions were washed with brine (15 ml), dried ($Na_2SO_4$), filtered and concentrated in vacuo to yield 0.73 g of 5-methyl-6-[2-(3-pyridin-3-ylpropoxy)ethyl]-6H-imidazo[4,5-c]tetrazolo[1,5-a]quinoline as a red oil. This material was used without further purification.

MS (CI) m/e 388 (M+H).

Part B

Under an atmosphere of nitrogen, 5-methyl-6-[2-(3-pyridin-3-ylpropoxy)ethyl]-6H-imidazo[4,5-c]tetrazolo[1,5-a]quinoline (0.73 g, 1.89 mmol) and triphenylphosphine (0.64 g, 2.84 mmol) were dissolved in 1,2-dichlorobenzene (15 ml). The reaction was heated at reflux for 18 hours. After cooling to ambient temperature, the solvent was removed in vacuo. The resulting residue was treated with 1N HCl/water (30 ml) and vigorous stirring produced an off white suspension. The solid was removed by filtration leaving a yellow filtrate. The filtrate was treated with 10% sodium hydroxide/water until pH 11 was reached. The filtrate was extracted with dichloromethane (3×25 ml). The combined organic fractions were washed with brine (25 ml), dried ($Na_2SO_4$), filtered and concentrated in vaeuo to yield an orange oil. The oil was dissolved in a minimum amount of dichloromethane and diluted with ether to produce a precipitate. The solid was recrystallized from n-propyl acetate to yield 0.16 g of 2-methyl-1-[2-(3-pyridin-3-ylpropoxy)ethyl]-1H-imidazo[4,5-c]quinoline-4-amine as a tan solid, m.p. 145.0–146.0.

$^1$H NMR (300 MHz, CDCl$_3$) δ 8.40 (d, J=4.9 Hz, 1H), 8.34 (d, J=2.0 Hz, 1H), 7.93 (d, J=7.4 Hz, 1H), 7.84 (d, J=8.4 Hz, 1H), 7.52 (t, J=7.2 Hz, 1H), 7.31 (t, J=6.6 Hz, 1H), 7.22 (d, J=7.8 Hz, 1H), 7.09 (dd, J=4.8, 7.8 Hz, 1H), 5.46 (bs, 2H), 4.67 (t, J=5.3 Hz, 2H), 3.90 (t, J=5.3 Hz, 2H), 3.34 (t, J=6.2 Hz, 2H), 2.70 (s, 3H), 2.52 (t, J=8.0 Hz, 2H), 1.76 (m, 2H);

MS (CI) m/e 362 (M+H),;

Anal calcd for $C_{21}H_{23}N_5O$: C, 69.78; H, 6.41; N, 19.38. Found: C, 69.40; H, 6.38; N, 19.00.

EXAMPLE 35

2-Butyl-1-[2-(3-pyridin-3-ylpropoxy)ethyl]-1H-imidazo[4,5-c]quinoline-4-amine

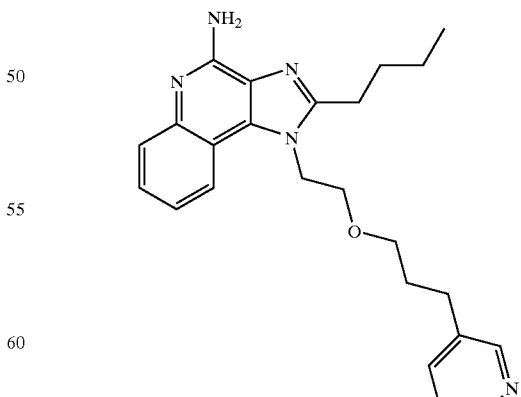

Part A

Under an atmosphere of nitrogen, $N^5$-[2-(3-pyridin-3-ylpropoxy)ethyl]tetrazolo[1,5-a]quinoline-4,5-diamine (2.48 g, 6.82 mmol) was dissolved in toluene (40 ml). Trimethyl orthovalerate (1.29 ml, 7.51 mmol) was added via syringe. A catalytic amount of pyridine hydrochloride was added to the reaction and the flask was fitted with a Dean-Stark trap. The reaction was heated to reflux and the volatiles were collected in the trap. After 4 hours, the reaction was cooled to room temperature and quenched by the addition of water (30 ml). The phases were separated and the aqueous phase was extracted with ethyl acetate (3×15 ml). The combined organic fractions were washed with brine (25 ml), dried ($Na_2SO_4$), filtered and concentrated in vacuo to provide a red/brown oil. The material was purified by flash column chromatography (silica gel, 2/1 to 95/5 ethyl acetate/hexane gradient) to yield 1.98 g of 2-butyl-6-[2-(3-pyridin-3-ylpropoxy)ethyl]-6H-imidazo[4,5-c]tetrazolo[1,5-a]quinoline as an orange oil.

$^1$H NMR (300 MHz, DMSO-$d_6$) δ 8.53 (d, J=8.2 Hz, 1 H), 8.41 (d, J=7.9 Hz, 1 H), 8.37 (d, J=5.0 Hz, 1 H), 8.31 (d, J=1.9 Hz, 1 H), 7.84 (d, J=7.2 Hz, 1 H), 7.75 (t, J=7.5 Hz, 1 H), 7.48 (d, J=7.9 Hz, 1 H), 7.23 (dd, J=7.8, 4.9 Hz, 1 H), 3.63 (t, J=5.0 Hz, 2 H), 3.56 (t, J=4.9 Hz, 2 H), 3.36 (t, J=6.3 Hz, 2 H), 2.51 (m, 2H), 2.12 (t, J=7.7 Hz, 2 H), 1.73 (pentet, J=7.4 Hz, 2 H), 1.45 (pentet, J=7.7 Hz, 2 H), 1.12 (m, 2 H), 0.68 (t, J=7.4 Hz, 3 H);

MS (CI) m/e 430 (M+H).

Part B

2-Butyl-6-[2-(3-pyridin-3-ylpropoxy)ethyl]-6H-imidazo[4,5-c]tetrazolo[1,5-a]quinoline (1.98 g, 4.61 mmol) was treated following the general procedure described in Example 35. Recrystallization from isopropyl alcohol gave 1.09 g of 2-butyl-1-[2-(3-pyridin-3-ylpropoxy)ethyl]-1H-imidazo[4,5-c]quinoline-4-amine as a beige solid.

$^1$H NMR (300 MHz, DMSO-$d_6$) δ 8.33 (d, J=4.3 Hz, 1 H), 8.24 (s, 1 H), 8.08 (d, J=8.7 Hz, 1 H), 7.61 (d, J=8.0 Hz, 1 H), 7.41 (t, J=7.7 Hz, 1 H), 7.30–7.20 (m, 2 H), 7.15 (dd, J=7.4, 4.8 Hz, 1 H), 6.44 (bs, 2 H), 4.74 (t, J=5.4 Hz, 2 H), 3.82 (t, J=5.3 Hz, 2 H), 3.27 (t, J=5.9 Hz, 2 H), 2.97 (t, J=7.4 Hz, 2 H), 2.41 (t, J=7.5 Hz, 2 H), 1.84 (pentet, J=7.4 Hz, 2 H), 1.64 (pentet, J=7.2 Hz, 2 H), 1.46 (m, 2 H), 0.95 (t, J=7.3 Hz, 3 H);

MS (CI) m/e 404 (M+H);

Anal calcd for $C_{24}H_{29}N_5O$: C, 71.44; H, 7.24; N, 17.36. Found: C, 71.23; H, 6.98; N, 17.05.

EXAMPLE 36

2-(2-Methoxyethyl)-1-[2-(3-pyridin-3-ylpropoxy) ethyl]-1H-imidazo[4,5-c]quinolin-4-amine

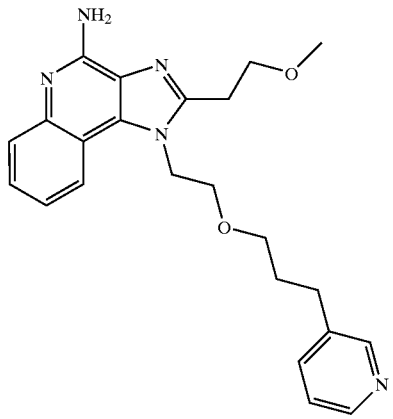

Part A

Under a nitrogen atmosphere, N5-[2-(3-pyridin-3-ylpropoxy)ethyl]tetraazolo[1,5-a]quinoline-4,5-diamine (2.48 g, 6.82 mmol), 1,2-dichloroethane (30 ml), and triethylamine (1.14 ml, 8.2 mmol) were combined and the resulting solution was chilled in an ice water bath. 3-methoxypropionyl chloride (0.92 g, 7.5 mmol) was added dropwise to the solution. The cooling bath was removed and the reaction was stirred for an additional 18 hours. The solution was quenched by the addition of water (30 ml). The phases were separated and the aqueous phase was extracted with dichloromethane (2×15 ml). The combined organic fractions were washed with brine (20 ml), dried ($Na_2SO_4$), filtered and concentrated to yield 3.16 g of an orange syrup. LCMS analysis of the crude product showed a mixture of mono- and di-acylated product. The material was used without further purification.

Part B

Under a nitrogen atmosphere, the product from part A (3.16 g), toluene (40 ml), and pyridine hydrochloride (50 mg, 0.4 mmol) were combined and the resulting mixture was heated at reflux temperature for 4 hours. The volatiles were collected in a Dean-Stark trap. The reaction was cooled to ambient temperature and then diluted with water (30 ml). The phases were separated and the aqueous phase was extracted with dichloromethane (3×20 ml). The combined organic extracts were washed with brine (20 ml), dried ($Na_2SO_4$), filtered and concentrated to yield an orange foam. The material was purified by column chromatography (silica gel, 99:1 $CHCl_3$:MeOH gradient to 9:1) and then recrystallized from 2-propanol to yield 0.35 g of 5-(2-methoxyethyl)-6-[2-(3-pyridin-3-ylpropoxy)ethyl]-6H-imidazo[4,5-c]tetraazolo[1,5-a]quinoline as a beige solid.

Part C 5-(2-methoxyethyl)-6-[2-(3-pyridin-3-ylpropoxy)ethyl]-6H-imidazo[4,5-c]tetraazolo[1,5-a]quinoline (0.35 g, 0.80 mmol) was treated with triphenylphosphine (0.28 g, 1.20 mmol) using the general procedure described in Part B of example 35. The crude product was crystallized from ether to yield 90 mg of 2-(2-methoxyethyl)-1-[2-(3-pyridin-3-ylpropoxy)ethyl]-1H-imidazo[4,5-c]quinolin-4-amine as off-white crystals.

$^1$H NMR (300 MHz, $CDCl_3$) δ 8.39 (dd, J=4.8, 1.5 Hz, 1 H), 8.33 (d, J=1.8 Hz, 1 H), 7.94 (d, J=7.4 Hz, 1 H), 7.83 (d, J=8.3 Hz, 1 H), 7.52–7.47 (m, 1 H), 7.32–7.21 (m, 2 H), 7.09 (dd, J=7.0, 4.8 Hz, 1 H), 5.59 (bs, 2 H), 4.74 (t, J=5.4 Hz, 2 H), 3.90 (t, J=6.6 Hz, 2 H), 3.87 (t, J=5.4 Hz, 2 H), 3.38 (s, 3 H), 3.33 (t, J=6.1 Hz, 2 H), 3.28 (t, J=6.6 Hz, 2 H), 2.51 (t, J=7.4 Hz, 2 H), 1.81–1.71 (m, 2 H);

$^{13}$C NMR (75 MHz, $CDCl_3$) δ 152.4, 151.6, 150.2, 147.8, 145.2, 137.1, 136.2, 133.7, 127.7, 127.4, 123.6, 122.5, 120.0, 115.9, 71.2, 70.6, 69.6, 59.4, 46.1, 31.1, 29.6, 28.7;

MS(CI) m/e 406.2242 calcd for (406.2243 $C_{23}H_{28}N_5O_2$, M+H).

EXAMPLE 37

2-methyl-1-[2-(3-pyridin-3-ylpropoxy)ethyl]-6,7,8,9-tetrahydro-1H-imidazo[4,5-c]quinolin-4-amine

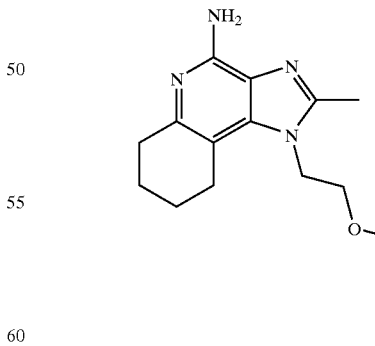

Part A

A 200 mL round bottom flask was charged with 3-nitro-5,6,7,8-tetrahydroquinoline-2,4-diol (10 g, 0.048 mol.) and phosphorous oxychloride (100 mL, 1.07 mol., 22 equivalents). The reaction mixture was heated to 80° C. and maintained, with stirring for six hours. The reaction was quenched by slowly adding the reaction mixture to water (1500 mL). The reaction mixture was extracted with dichloromethane (4×100 mL). The dichloromethane fractions were combined, dried over magnesium sulfate and concentrated to provide 2,4-dichloro-3-nitro-5,6,7,8-tetrahydroquinoline as a tan solid (10.6 g, 91%). m.p. 63–64° C. TLC (10% MeOH/CH2CL2, Rf=0.84).

Part B

A 200 ml round bottom flask was charged with 2,4-dichloro-3-nitro-5,6,7,8-tetrahydroquinoline (10 g, 0.04 mol), triethylamine (6.1 g, 0.06 mol, 1.5 equivalents) and anhydrous N,N-dimethylformamide (100 mL). To this solution was added 2-(3-pyridin-3-ylpropoxy)ethanamine (7.3 g, 0.04 mol). The reaction mixture was heated to 55° C. and maintained overnight with stirring. The reaction was quenched by pouring into water (1000 mL). The reaction mixture was then extracted with a 1:1 solution of hexane/ethyl acetate (4×200 mL). The organics were combined, washed with brine (300 mL) and concentrated to provide 2-chloro-3-nitro-N-[2-(3-pyridin-3-ylpropoxy)ethyl]-5,6,7,8-tetrahydroquinolin-4-amine as an orange syrup (14.8 g, 94%). TLC (10% MeOH/CH2CL2, Rf=0.84).

Part C

A 200 mL round bottom flask was charged with 60% sodium hydride (2.5 g, 0.06 mol, 1.7 equivalents) and washed with hexane (50 mL). A solution of phenol (5.7 g, 0.06 mol, 1.6 equivalents) in diglyme (25 mL) was then slowly added to the sodium hydride. The reaction was maintained with stirring at room temperature for 1.5 hours. To the phenol anion solution was slowly added a solution of 2-chloro-3-nitro-N-[2-(3-pyridin-3-ylpropoxy)ethyl]-5,6,7,8-tetrahydroquinolin-4-amine (14.8 g, 0.04 mol) in diglyme (25 mL). The stirred reaction mixture was heated to 60° C. and maintained overnight. The reaction was quenched by pouring onto ice (1000 mL). The product oiled out of solution. The mixture was extracted with dichloromethane (4×100 mL). The combined extracts were concentrated to dryness. The residue was taken up in 1:1 hexane/ethyl acetate (250 mL) and washed with water (2×50 mL). The organic layer was concentrated to dryness. The residue was found to contain excess phenol. The phenol was removed by taking the residue up in diethyl ether (500 mL) and stirring over 10% sodium hydroxide (250 mL) overnight. The layers were separated. The ether layer was concentrated to provide 3-nitro-2-phenoxy-N-[2-(3-pyridin-3-ylpropoxy)ethyl]-5,6,7,8-tetrahydroquinolin-4-amine as a pale orange syrup (12.0 g, 71%). TLC=(10% MeOH/CH2Cl2, Rf=0.58).

Part D

A 500 mL Parr bottle was charged with a solution of 3-nitro-2-phenoxy-N-[2-(3-pyridin-3-ylpropoxy)ethyl]-5,6,7,8-tetrahydroquinolin-4-amine in toluene (150 mL) and 5% Pt/C catalyst (1.1 g), placed on Parr apparatus and charged with hydrogen (~54 psi, 3.8 Kg/cm²). The reaction was allowed to shake for 4 hours, at which time the reaction was monitored by HPLC. The reaction was not complete. An additional 1.0 g 5% Pt/C catalyst was added to the Parr bottle, it was recharged with hydrogen and shaken overnight. The reaction was then complete. The mixture was filtered through Celite and washed with toluene (500 mL). The filtrate was concentrated to provide 2-phenoxy-N⁴-[2-(3-pyridin-3-ylpropoxy)ethyl]-5,6,7,8-tetrahydroquinoline-3,4-diamine as a yellow syrup (8.2 g, 74%). TLC (10% MeOH/CH2Cl2, Rf=0.48). Mass-spec M+1=419.2

Part E

A 200 ml round bottom flask was charged with 2-phenoxy-N4-[2-(3-pyridin-3-ylpropoxy)ethyl]-5,6,7,8-tetrahydroquinoline-3,4-diamine (4.1 g, 0.0098 mol.) and pyridine (40 mL) at room temperature. To this solution was slowly added acetyl chloride (0.8 g, 0.011 mol., 1.1 equivalents). The reaction was maintained with stirring at room temperature. After two hours the reaction was monitored and found to only contain the amide intermediate. The reaction mixture was then heated to reflux and maintained overnight. The reaction mixture was concentrated to provide a dark amber syrup. The syrup was taken up in ethyl acetate (300 mL) and washed with water (2×100 mL). The ethyl acetate layer was concentrated to provide 2-methyl-4-phenoxy-1-[2-(3-pyridin-3-ylpropoxy)ethyl]-6,7,8,9-tetrahydro-1H-imidazo[4,5-c]quinoline as an orange syrup (3.8 g, 88%). TLC (10%MeOH/CH2Cl2, Rf=0.34). Mass-spec M+1=443.2

Part F

A 200 ml round bottom flask was charged with 2-methyl-4-phenoxy-1-[2-(3-pyridin-3-ylpropoxy)ethyl]-6,7,8,9-tetrahydro-1H-imidazo[4,5-c]quinoline (3.7 g, 0.0084 mol.) and ammonium acetate (37 g, 0.48 mol, 57 equivalents) and then heated to 150° C. Within 20 minutes the reaction mixture was homogeneous. The reaction mixture was maintained with stirring at 150° C. overnight. The reaction was monitored after 24 hours and found to be incomplete. The reaction mixture was maintained over the weekend. The reaction mixture was cooled and then taken up in 1N HCl (250 mL) and washed with diethyl ether (200 mL). The aqueous layer was then adjusted to pH 11 with sodium hydroxide and extracted with dichloromethane (3×100 mL). The combined organics were concentrated to provide an orange syrup. The syrup was purified by column chromatography (10% MeOH/CH2Cl2). The appropriate fractions were combined and concentrated to provide a pale orange syrup. The syrup was found to be a mixture of the desired product and N-acetylated product. The mixture was treated with refluxing 1N HCl for 1 hour. The mixture was cooled, adjusted to pH 11 and then extracted with dichloromethane. The organics were concentrated to dryness. The residue was purified by column chromatography to provide 2-methyl-1-[2-(3-pyridin-3-ylpropoxy)ethyl]-6,7,8,9-tetrahydro-1H-imidazo[4,5-c]quinolin-4-amine as a pale gold solid (0.07 g, 2%). TLC (10% MeOH/CH2Cl2 Rf=0.05). m.p. 140–141° C.

Cytokine Induction in Human Cells

An in vitro human blood cell system is used to assess cytokine induction. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMCs) are separated from whole blood by density gradient centrifugation using Histopaque®-1077. The PBMCs are washed twice with Hank's Balanced Salts Solution and then are suspended at 3–4×10⁶ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells Incubation The solution of test compound is added at 60 μM to the first well containing RPMI complete and serial 3 fold dilutions are made in the wells. The PBMC suspension is then added to the wells in an equal volume, bringing the test compound concentrations to the desired range (0.12 to 30 μM). The final concentration of PBMC suspension is 1.5–2× $10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 5–10 minutes at 1000 rpm (~200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) and for tumor necrosis factor (α) by ELISA.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF)concentration is determined using ELISA kits available from Genzyme, Cambridge, Mass.; R&D Systems, Minneapolis, Minn.; or Pharmingen, San Diego, Calif. Results are expressed in pg/mL.

The table below lists the lowest concentration found to induce interferon and the lowest concentration found to induce tumor necrosis factor for each compound. A "*" indicates that no induction was seen at any of the concentrations; generally the highest tested concentration was 10 or 30 μM.

| Example Number | Cytokine Induction in Human Cells | |
|---|---|---|
| | Lowest Effective Concentration (μM) | |
| | Interferon | Tumor Necrosis Factor |
| 1 | 0.12 | 3.33 |
| 2 | 0.37 | 10 |
| 3 | 0.04 | * |
| 4 | 3.33 | * |
| 5 | 0.04 | 0.37 |
| 6 | 0.12 | 1.11 |
| 7 | 0.37 | * |
| 8 | 0.04 | 0.12 |
| 9 | 0.12 | 3.33 |
| 10 | 1.11 | 1.11 |
| 11 | 1.11 | 0.04 |
| 12 | 1.11 | * |
| 13 | 0.37 | 1.11 |
| 14 | 0.12 | 0.37 |
| 15 | 1.11 | 3.33 |
| 16 | 3.33 | 10 |
| 17 | 0.37 | 0.37 |
| 18 | 0.37 | 10 |
| 19 | 0.12 | 3.33 |
| 20 | 0.12 | 3.33 |
| 21 | 1.11 | 10 |
| 22 | 1.11 | 10 |
| 23 | 1.11 | * |
| 24 | * | * |
| 25 | 10 | * |
| 26 | 1.11 | * |
| 27 | 1.11 | * |
| 29 | 1.11 | * |
| 30 | 0.37 | 3.33 |

-continued

| Example Number | Cytokine Induction in Human Cells | |
|---|---|---|
| | Lowest Effective Concentration (μM) | |
| | Interferon | Tumor Necrosis Factor |
| 31 | 3.33 | 3.33 |
| 32 | 0.01 | 1.11 |
| 33 | 0.04 | 0.12 |
| 34 | 0.01 | 0.04 |
| 35 | 0.01 | 0.12 |

What is claimed is:

1. A compound of the formula (I):

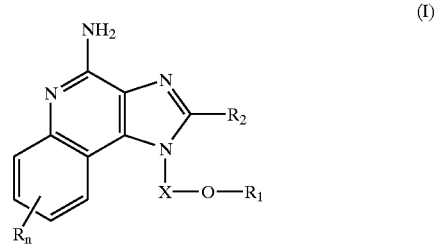

wherein:

X is —CHR$_3$—, —CHR$_3$-alkyl-, or —CHR$_3$-alkenyl-;

R$_1$ is selected from the group consisting of:
-heteroaryl;
-heterocyclyl;
—R$_4$-heteroaryl; and
—R$_4$-heterocyclyl;

R$_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;

R$_4$ is alkyl or alkenyl, which may be interrupted by one or more —O— groups;

each R$_3$ is independently H or C$_{1-10}$ alkyl;

each Y is independently —O— or —S(O)$_{0-2}$—;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

2. A compound or salt of claim 1 wherein $R_1$ is —(CH$_2$)$_{0-3}$-heteroaryl.

3. A compound or salt of claim 2 wherein the heteroaryl is selected from the group consisting of 2-pyridyl, 3-pyridyl, 4-pyridyl, 2-thiazolyl, 2-pyrimidinyl, 4-pyrimidinyl, 4-triazolyl, 2-benzofuranyl, 2-indolyl, 3-carbazolyl, 2-furanyl, 4-isoquinolinyl, 4-isoxazolyl, and 4-pyrazolyl.

4. A compound or salt of claim 1 wherein X is —CH(alkyl)(alkyl)-wherein the alkyl groups can be the same or different.

5. A compound or salt of claim 1 wherein X is —CH$_2$—CH$_2$—.

6. A compound or salt of claim 1 wherein X is —CH(C$_2$H$_5$)(CH$_2$)—.

7. A compound or salt of claim 1 wherein $R_2$ is H.

8. A compound or salt of claim 1 wherein $R_2$ is alkyl.

9. A compound or salt of claim 1 wherein $R_2$ is -alkyl-O-alkyl.

10. A compound of the formula (II)

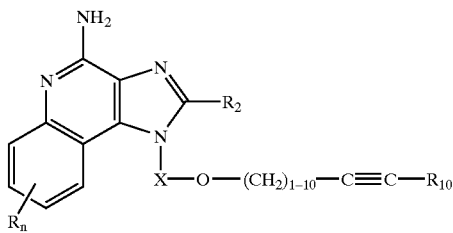

(II)

wherein:
X is —CHR$_3$—, —CHR$_3$-alkyl-, or —CHR$_3$-alkenyl-;
$R_{10}$ is selected from the group consisting of heteroaryl and heterocyclyl;
$R_2$ is selected from the group consisting of:
  -hydrogen;
  -alkyl;
  -alkenyl;
  -aryl;
  -heteroaryl;
  -heterocyclyl;
  -alkyl-Y-alkyl;
  -alkyl-Y-alkenyl;
  -alkyl-Y-aryl; and
  -alkyl or alkenyl substituted by one or more substituents selected from the group consisting of:
    —OH;
    -halogen;
    —N(R$_3$)$_2$;
    —CO—N(R$_3$)$_2$;
    —CO—C$_{1-10}$ alkyl;
    —CO—O—C$_{1-10}$ alkyl;
    —N$_3$;
    -aryl;
    -heteroaryl;
    -heterocyclyl;
    —CO-aryl; and
    —CO-heteroaryl;
n is 0 to 4;
each R$_3$ is independently H or C$_{1-10}$ alkyl;
each Y is independently —O— or —S(O)$_{0-2}$—; and
each R present is independently selected from the group consisting of C$_{1-10}$ alkyl, C$_{1-10}$ alkoxy, hydroxy, halogen and trifluoromethyl;
or a pharmaceutically acceptable salt thereof.

11. A compound or salt of claim 10 wherein $R_{10}$ is selected from the group consisting of heteroaryl and substituted heteroaryl.

12. A compound of claim 11 wherein the heteroaryl is selected from the group consisting of 2-pyridyl, 3-pyridyl, 4-pyridyl, 2-thiazolyl, 4-pyrazolyl, 3-furanyl, 2-thienyl, and 2-pyrimidinyl.

13. A compound or salt of claim 10 wherein X is —CH(alkyl)(alkyl)-, wherein the alkyl groups can be the same or different.

14. A compound or salt of claim 10 wherein X is —CH$_2$—CH$_2$—.

15. A compound or salt of claim 10 wherein X is —CH(C$_2$H$_5$)(CH$_2$)—.

16. A compound or salt of claim 10 wherein $R_2$ is H, alkyl, or alkyl-O-alkyl.

17. A compound selected from the group consisting of:
  1-(2-{[3-(isoquinolin-4-yl)-2-propynyl]oxy}ethyl)-1H-imidazo[4,5-c]quinolin-4-amine;
  1-(2-{[3-(1,3-thiazol-2-yl)-2-propynyl]oxy}ethyl)-1H-imidazo[4,5-c]quinolin-4-amine;
  1-{2-[3-(1H-4-pyrazolyl)propoxy]ethyl}-1H-imidazo[4,5-c]quinolin-4-amine;
  1-[2-(3-pyrimidin-2-ylpropoxy)ethyl]-1H-imidazo[4,5-c]quinolin-4-amine;
  1-[2-(3-pyridin-4-ylpropoxy)ethyl]-1H-imidazo[4,5-c]quinolin-4-amine;
  1-[2-(3-pyridin-2-ylpropoxy)ethyl]-1H-imidazo[4,5-c]quinolin-4-amine;
  1-{2-[3-(1,3-thiazol-2-yl)propoxy]ethyl }-1H-imidazo[4,5-c]quinolin-4-amine;
  1-[2-(3-pyridin-3-ylpropoxy)ethyl]-1H-imidazo[4,5-c]quinolin4-amine;
  1-[2-(3-pyrimidin-5-ylpropoxy)ethyl]-1H-imidazo[4,5-c]quinolin-4-amine;
  1-{2-[(1-benzyl-1H-1,2,3-triazol-4-yl)methoxy]ethyl}-1H-imidazo[4,5-c]quinoline-4-amine;
  1-{2-[(1-benzyl-1H-1,2,3-triazol-5-yl)methoxy]ethyl}-1H-imidazo[4,5-c]quinoline-4-amine;
  1-[2-({1-[(phenylsfanyl)methyl]-1H-1,2,3-triazol-4-yl}methoxy)ethyl]-1H-imidazo[4,5-c]quinoline-4-amine;
  1-[2-({1-[(phenylsulfanyl)methyl]-1H-1,2,3-triazol-5-yl}methoxy)ethyl]-1H-imidazo[4,5-c]quinoline-4-amine;
  1-[2-(benzo[b]furan-2-ylmethoxy)ethyl]-1H-imidazo[4,5-c]quinolin-4-amine;
  1-[2-(pyridin-3-ylmethoxy)ethyl]-1H-imidazo[4,5-c]quinolin-4-amine;
  1-[2-(pyridin-2-ylmethoxy)ethyl]-1H-imidazo[4,5-c]quinolin-4-amine;
  1-[2-(pyridin-4-ylmethoxy)ethyl]-1H-imidazo[4,5-c]quinolin-4-amine;
  1-{2-[(3,5-dimethylisoxazol-4-yl)methoxy]ethyl}-1H-imidazo[4,5-c]quinolin-4-amine;
  1-(2-{[3-(pyrimidin-2-yl)-2-propynyl]oxy}ethyl)-1H-imidazo[4,5-c]quinolin-4-amine;
  1-(2-{[3-(pyrid-4-yl)-2-propynyl]oxy}ethyl)-1H-imidazo[4,5-c]quinolin-4-amine;
  1-(2-{[3-(fur-3-yl)-2-propynyl]oxy}ethyl)-1H-imidazo[4,5-c]quinolin-4-amine;
  4-{3-[2-(4-amino-1H-imidazo[4,5-c]quinolin-1-yl)ethoxy]-propyn-1-yl}thiophen-2-ylcarboxaldehyde;

1-(2-{[3-(pyrid-2-yl)-2-propynyl]oxy}ethyl)-1H-imidazo[4,5-c]quinolin-4-amine;

1-{2-methyl-1-[(pyrid-2-yloxy)methyl]propyl}-1H-imidazo[4,5-c]quinoline-4-amine;

1-{1-[(pyrid-2-yloxy)methyl]propyl}-1H-imidazo[4,5-c]quinoline-4-amine;

1-[2-(9H-carbazol-3-yloxy)propyl]-1H-imidazo[4,5-c]quinolin-4-amine;

1-{2-[(3-thien-2-ylprop-2-ynyl)oxy]ethyl}-1H-imidazo[4,5-c]quinolin-4-amine;

1-{2-[(1-methyl-1H-indol-2-yl)methoxy]ethyl}-1H-imidazo[4,5-c]quinolin-4-amine;

1-[2-(3-thien-2-ylpropoxy)ethyl]-1H-imidazo[4,5-c]quinolin-4-amine;

2-methyl-1-[2-(3-pyridin-3-ylpropoxy)ethyl]-1H-imidazo[4,5-c]quinoline-4-amine;

2-butyl-1-[2-(3-pyridin-3-ylpropoxy)ethyl]-1H-imidazo[4,5-c]quinoline-4-amine;

1-[2-(tetrahydrofuran-2-ylmethoxy)propyl]-1H-imidazo[4,5-c]quinolin-4-amine;

1-{2-[(5-chloro-1-benzothien-3-yl)methoxy]propyl}-1H-imidazo[4,5-c]quinolin-4-amine;

1-{2-[(3-nitropyridin-2-yl)oxy]propyl}-1H-imidazo[4,5-c]quinolin-4-amine;

1-(2-methyl-1-{[(3-nitropyridin-2-yl)oxy]methyl}propyl)-1H-imidazo[4,5-c]quinolin-4-amine;

1-(1-{[(5-chloro-1-benzothien-3-yl)methoxy]methyl}-2-methylpropyl)-1H-imidazo[4,5-c]quinolin-4-amine;

2-(2-methoxyethyl)-1-[2-(3-pyridin-3-ylpropoxy)ethyl]-1H-imidazo[4,5-c]quinolin-4-amine; and 2-methyl-1-[2-(3-pyridin-3-ylpropoxy)ethyl]-6,7,8,9-tetrahydro-1H-imidazo[4,5-c]quinolin-4-amine;

or a pharmaceutically acceptable salt thereof.

18. A compound of the formula (III)

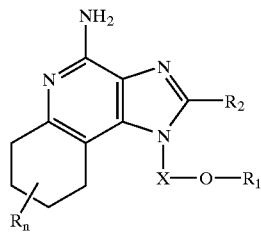

(III)

wherein:

X is —CHR$_3$—, —CHR$_3$-alkyl-, or —CHR$_3$-alkenyl-;

R$_1$ is selected from the group consisting of:
-heteroaryl;
-heterocyclyl;
—R$_4$-heteroaryl; and
—R$_4$-heterocyclyl;

R$_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;

R$_4$ is alkyl or alkenyl, which may be interrupted by one or more —O— groups;

each R$_3$ is independently H or C$_{1-10}$ alkyl;

each Y is independently —O— or —S(O)$_{0-2}$—;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

19. A compound or salt of claim 18 wherein R$_2$ is H or alkyl.

20. A compound or salt of claim 18 wherein R$_2$ is -alkyl-O-alkyl.

21. A compound of the formula (IV):

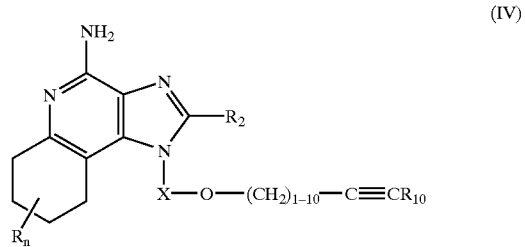

(IV)

wherein:

X is —CHR$_3$—, —CHR$_3$-alkyl-, or —CHR$_3$-alkenyl-;

R$_{10}$ is selected from the group consisting of heteroaryl and heterocyclyl;

R$_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;

each $R_3$ is independently H or $C_{1-10}$ alkyl;

each Y is independently —O— or —S(O)$_{0-2}$—;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

22. A pharmaceutical composition comprising a therapeutically effective amount of a compound or salt of claim 1 and a pharmaceutically acceptable carrier.

23. A pharmaceutical composition comprising a therapeutically effective amount of a compound or salt of claim 10 and a pharmaceutically acceptable carrier.

24. A pharmaceutical composition comprising a therapeutically effective amount of a compound or salt of claim 17 and a pharmaceutically acceptable carrier.

25. A method of inducing cytokine biosynthesis in an animal comprising administering a therapeutically effective amount of a compound or salt of claim 1 to the animal.

26. The method of claim 25 wherein the cytokine is IFN-α.

27. A method of inducing cytokine biosynthesis in an animal comprising administering a therapeutically effective amount of a compound or salt of claim 10 to the animal.

28. The method of claim 27 wherein the cytokine is IFN-α.

29. A method of treating a viral disease in an animal in need thereof comprising administering to the animal a therapeutically effective amount of a compound of claim 1 that induces cytokine biosynthesis.

30. A method of treating a viral disease in an animal in need thereof comprising administering to the animal a therapeutically effective amount of a compound of claim 10 that induces cytokine biosynthesis.

31. A method of inducing cytokine biosynthesis in an animal comprising administering a theraputically effective amount of a compound or salt of claim 17 to the animal.

32. The method of claim 31 wherein the cytokine is IFN-α.

33. A method of treating a viral disease in an animal in need thereof comprising administering to the animal a therapeutically effective amount of a compound of claim 17 that induces cytokine biosynthesis.

34. A compound of the formula (V):

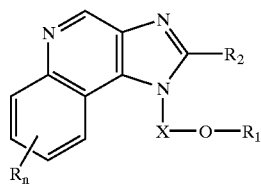

(V)

wherein:

X is —CHR$_3$—, —CHR$_3$-alkyl-, or —CHR$_3$-alkenyl-;

R$_1$ is selected from the group consisting of:
  -heteroaryl;
  -heterocyclyl;
  —R$_4$-heteroaryl;
  —R$_4$-heterocyclyl; and
  —(CH$_2$)$_{1-10}$—C≡C—R$_{10}$;

R$_2$ is selected from the group consisting of:
  -hydrogen;
  -alkyl;
  -alkenyl;
  -aryl;
  -heteroaryl;
  -heterocyclyl;
  -alkyl-Y-alkyl;
  -alkyl-Y-alkenyl;
  -alkyl-Y-aryl; and
  -alkyl or alkenyl substituted by one or more substituents selected from the group consisting of:
    —OH;
    -halogen;
    —N(R$_3$)$_2$;
    —CO—N(R$_3$)$_2$;
    —CO—C$_{1-10}$ alkyl;
    —CO—O—C$_{1-10}$ alkyl;
    —N$_3$;
    -aryl;
    -heteroaryl;
    -heterocyclyl;
    —CO-aryl; and
    —CO-heteroaryl;

R$_4$ is alkyl or alkenyl, which may be interrupted by one or more —O— groups;

each R$_3$ is independently H or $C_{1-10}$ alkyl;

R$_{10}$ is heteroaryl or heterocyclyl;

each Y is independently —O— or —S(O)$_{0-2}$—;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

35. A compound of the formula (VI):

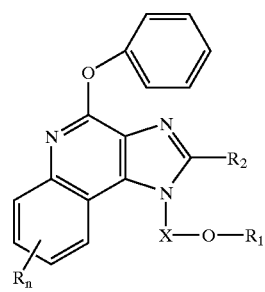

(VI)

wherein:

X is —CHR$_3$—, —CHR$_3$-alkyl-, or —CHR$_3$-alkenyl-;

R$_1$ is selected from the group consisting of:
  -heteroaryl;
  -heterocyclyl;
  —R$_4$-heteroaryl;
  —R$_4$-heterocyclyl; and
  —(CH$_2$)$_{1-10}$—C≡C—R$_{10}$;

R$_2$ is selected from the group consisting of:
  -hydrogen;
  -alkyl;
  -alkenyl;
  -aryl;
  -heteroaryl;
  -heterocyclyl;
  -alkyl-Y-alkyl;
  -alkyl-Y-alkenyl;
  -alkyl-Y-aryl; and
  -alkyl or alkenyl substituted by one or more substituents selected from the group consisting of:

—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;

R$_4$ is alkyl or alkenyl, which may be interrupted by one or more —O— groups;

each R$_3$ is independently H or C$_{1-10}$ alkyl;

R$_{10}$ is heteroaryl or heterocyclyl;

each Y is independently —O— or —S(O)$_{0-2}$—;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

36. A compound of the formula (VIII):

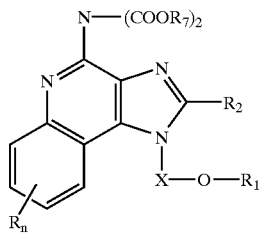

(VIII)

wherein:

X is —CHR$_3$—, —CHR$_3$-alkyl-, or —CHR$_3$-alkenyl-;

R$_1$ is selected from the group consisting of:
-heteroaryl;
-heterocyclyl;
—R$_4$-heteroaryl; and
—R$_4$-heterocyclyl;

R$_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;

R$_4$ is alkyl or alkenyl, which may be interrupted by one or more —O— groups;

each R$_3$ is independently H or C$_{1-10}$ alkyl;

each Y is independently —O— or —S(O)$_{0-2}$—;

n is 0 to 4;

each R present is independently selected from the group consisting of C$_{1-10}$ alkyl, C$_{1-10}$ alkoxy, hydroxy, halogen and trifluoromethyl; and R$_7$ is tert-butyl or benzyl;

or a pharmaceutically acceptable salt thereof.

37. A compound of the formula (IX)

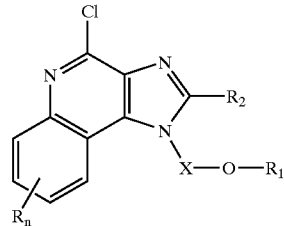

(IX)

wherein:

X is —CHR$_3$—, —CHR$_3$-alkyl-, or —CHR$_3$-alkenyl-;

R$_1$ is selected from the group consisting of:
-heteroaryl;
-heterocyclyl;
—R$_4$-heteroaryl; and
—R$_4$-heterocyclyl;

R$_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N(R$_3$)$_2$;
—CO—N(R$_3$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;

R$_4$ is alkyl or alkenyl, which may be interrupted by one or more —O— groups;

each R$_3$ is independently H or C$_{1-10}$ alkyl;

each Y is independently —O— or —S(O)$_{0-2}$—;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

38. A pharmaceutical composition comprising a therapeutically effective amount of a compound or salt of claim 18 and a pharmaceutically acceptable carrier.

39. A method of inducing cytokine biosynthesis in an animal comprising administering a therapeutically effective amount of a compound or salt of claim 18 to the animal.

40. The method of claim 39 wherein the cytokine is IFN-α.

41. A method of treating a viral disease in an animal in need thereof comprising administering to the animal a therapeutically effective amount of a compound of claim 18 that induces cytokine biosynthesis.

42. A pharmaceutical composition comprising a therapeutically effective amount of a compound or salt of claim 21 and a pharmaceutically acceptable carrier.

43. A method of inducing cytokine biosynthesis in an animal comprising administering a therapeutically effective amount of a compound or salt of claim 21 to the animal.

44. The method of claim 43 wherein the cytokine is IFN-α.

45. A method of treating a viral disease in an animal in need thereof comprising administering to the animal a therapeutically effective amount of a compound of claim 21 that induces cytokine biosynthesis.

46. A compound of the formula (VII):

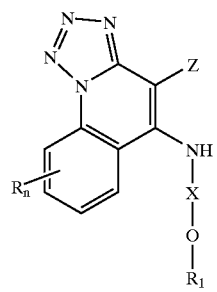

(VII)

wherein:

Z is NH$_2$ or NO$_2$;

X is —CHR$_3$—, —CHR$_3$-alkyl-, or —CHR$_3$-alkenyl-;

R$_1$ is selected from the group consisting of:
- -heteroaryl;
- -heterocyclyl;
- —R$_4$-heteroaryl; and
- —R$_4$-heterocyclyl;

R$_4$ is alkyl or alkenyl, which may be interrupted by one or more —O— groups;

each R$_3$ is independently H or C$_{1-10}$ alkyl;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

47. A compound of the formula (XLIV):

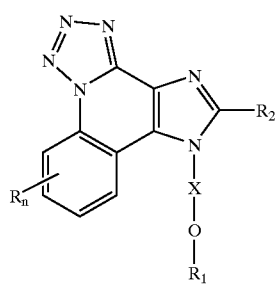

(XLIV)

wherein:

X is —CHR$_3$—, —CHR$_3$-alkyl-, or —CHR$_3$-alkenyl-;

R$_1$ is selected from the group consisting of:
- -heteroaryl;
- -heterocyclyl;
- —R$_4$-heteroaryl; and
- —R$_4$-heterocyclyl;

R$_2$ is selected from the group consisting of:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from the group consisting of:
  - —OH;
  - -halogen;
  - —N(R$_3$)$_2$;
  - —CO—N(R$_3$)$_2$;
  - —CO—C$_{1-10}$ alkyl;
  - —CO—O—C$_{1-10}$ alkyl;
  - —N$_3$;
  - -aryl;
  - -heteroaryl;
  - -heterocyclyl;
  - —CO-aryl; and
  - —CO-heteroaryl;

R$_4$ is alkyl or alkenyl, which may be interrupted by one or more —O— groups;

each R$_3$ is independently H or C$_{1-10}$ alkyl;

each Y is independently —O— or —S(O)$_{0-2}$—;

n is 0 to 4; and each R present is independently selected from the group consisting of C$_{1-10}$ alkyl, C$_{1-10}$ alkoxy, hydroxy, halogen and trifluoromethyl;

or a pharmaceutically acceptable salt thereof.

48. The method according to claim 25 wherein the animal has a viral disease.

49. The method according to claim 25 wherein the animal has a neoplastic disease.

50. The method according to claim 27 wherein the animal has a viral disease.

51. The method according to claim 27 wherein the animal has a neoplastic disease.

52. The method according to claim 31 wherein the animal has a viral disease.

53. The method according to claim 31 wherein the animal has a neoplastic disease.

54. The method according to claim 39 wherein the animal has a viral disease.

55. The method according to claim 39 wherein the animal has a neoplastic disease.

56. The method according to claim 43 wherein the animal has a viral disease.

57. The method according to claim 43 wherein the animal has a neoplastic disease.

* * * * *

UNITED STATES PATENT AND TRADEMARK OFFICE
CERTIFICATE OF CORRECTION

PATENT NO. : 6,664,260 B2
DATED : December 16, 2003
INVENTOR(S) : Charles, Leslie J.

It is certified that error appears in the above-identified patent and that said Letters Patent is hereby corrected as shown below:

<u>Title page,</u>
Item [56], References Cited, OTHER PUBLICATIONS, "Bachman et al." reference, please delete "`18" and insert -- 15 --, therefore.

<u>Column 1,</u>
Line 23, please delete "system." and insert in place thereof -- system, --.

<u>Column 3,</u>
Line 20, please delete "-S(O)O$_{0-2}$-" and insert - - -S(O)$_{0-2}$- --, therefore.

<u>Column 5,</u>
Line 35, please delete "groups" and insert in place thereof -- group --.

<u>Column 8,</u>
Line 10, please delete delete "benzyltrimethlammonium" and insert -- benzyltrimethyl-ammonium --, therefore.

<u>Column 13,</u>
Formula XXVI, (Reaction Scheme V), below "X" delete "OH" and insert -- O --, therefore.
Formula XXXI, (Reaction Scheme V), below "X" delete "OH" and insert -- O --, therefore.

<u>Column 15,</u>
Formula XXVI, (Reaction Scheme VI), below "X" delete "OH" and insert -- O --, therefore.

<u>Column 16,</u>
Line 10, before "reacted" delete "is".

<u>Column 17,</u>
Line 13, please delete "quinolin4-amine" and insert -- quinolin-4-amine --, therefore.
Formula XXXV, please delete "-O" (attached to N$^+$) and insert in place thereof -- —O$^-$ --,

UNITED STATES PATENT AND TRADEMARK OFFICE
CERTIFICATE OF CORRECTION

PATENT NO. : 6,664,260 B2
DATED : December 16, 2003
INVENTOR(S) : Charles, Leslie J.

It is certified that error appears in the above-identified patent and that said Letters Patent is hereby corrected as shown below:

Column 22,
Formula XLVIII, please delete "-O" (attached to $N^+$) and insert in place thereof
-- —$O^-$ --.

Column 25,
About line 29, please delete "$R_{10}$," and insert in place thereof -- $R_{10}$; --.

Column 26,
Line 18, please delete "$CHR_3$ - alkenyl-" and insert in place thereof -- -$CHR_3$ - Alkenyl- --.

Column 28,
Lines 31 & 32, below "-hydrogen," insert -- -alkyl--.

Column 33,
Line 2, please delete "rometbane" and insert in place thereof -- romethane --.

Column 35,
Lines 46-47, delete "(1,is *tert*-butoxycarbonyl)" and insert
-- (bis *tert*-butoxycarbonyl) --, therefore.
Line 50, please delete "MS(C)" and insert -- MS(CI) --, therefore.
Line 54, please delete "0.97" and insert -- 0.11 --, therefore.

Column 36,
Line 27, please delete "Dicblorobis" and insert -- Dichlorobis --, therefore.

Column 37,
Lines 5-6, please delete "1-{2-[3-(1H-pyrazo-4-1-yl)" and insert -- 1-{2-[3-(1*H*-pyrazo-4-yl) --, therefore.
Line 8, please delete "$C_{18}H_2N_6O \cdot (CF_3CO_2H)_{,0\ 15}$" and insert
-- $C_{18}H_{20}N_6O \cdot (CF_3CO_2H)_{0.15}$ -- therefore.

UNITED STATES PATENT AND TRADEMARK OFFICE
CERTIFICATE OF CORRECTION

PATENT NO.   : 6,664,260 B2
DATED        : December 16, 2003
INVENTOR(S)  : Charles, Leslie J.

It is certified that error appears in the above-identified patent and that said Letters Patent is hereby corrected as shown below:

<u>Column 43,</u>
Line 25, please delete "[-(2-propynyloxy)ethyl]" and insert
-- [2-(2-propynyloxy)ethyl] --, therefore.

<u>Column 46,</u>
Line 37, please delete "4.49 (s, 1.6 H)," before "4.42".

<u>Column 49,</u>
Line 54, please delete "(t, $J$ = 5.4 Hz, 11H)" and insert -- (t, $J$= 5.4 Hz, 1H) -- therefore.
Lines 54-55, please delete "(g, $J$ = 5.4 Hz, 2H)" and insert -- (q, $J$ = 5.4 Hz, 2H) therefore.
Line 61, please delete "(0.03 g)" and insert -- (~0.03 g) --, therefore.

<u>Column 53,</u>
Line 30, please delete "dimethylfornamide" and insert -- dimethylformamide -- therefore.

<u>Column 54,</u>
Line 58, please delete "dimethylfonnamide" and insert -- dimethylformamide -- therefore.

<u>Column 60,</u>
Line 55, please delete "dimethylfornamide" and insert -- dimethylformamide -- therefore.

<u>Column 61,</u>
Line 29, please delete "quinioline" and insert -- quinoline --, therefore.
Line 34, please delete "exothermn" and insert -- exotherm --, therefore <u>Column 62,</u>
Line 22, please delete "13" and insert -- ~13 --, therefore.

<u>Column 63,</u>
Line 66, please delete "quinolin" and insert -- quinoline --, therefore.

UNITED STATES PATENT AND TRADEMARK OFFICE
CERTIFICATE OF CORRECTION

PATENT NO. : 6,664,260 B2
DATED : December 16, 2003
INVENTOR(S) : Charles, Leslie J.

It is certified that error appears in the above-identified patent and that said Letters Patent is hereby corrected as shown below:

Column 67,
Line 1, please delete "(d, J'7.7 Hz, 1H)" and insert -- (d, J=7.7 Hz, 1H) -- therefore.
Line 3, please delete " 3.9" and insert -- 3.96 --, therefore.

Column 68,
Line 5, delete "dichioromethane" and insert -- dichloromethane --, therefore.
Line 26, please delete "vaeuo" and insert -- *vacuo* --, therefore.

Column 72,
Line 67, please insert -- . -- after "wells",

Column 76,
Line 35, please delete "quinolin4-amine" and insert -- quinolin-4-amine --, therefore.
Line 42, please delete "phenylsfanyl" and insert -- phenylsulfanyl -- therefor.

Column 79,
Line 37, please delete "theraputically" and insert -- therapeutically -- therefore.

Signed and Sealed this

Third Day of August, 2004

JON W. DUDAS
*Acting Director of the United States Patent and Trademark Office*